(12) United States Patent
Meng et al.

(10) Patent No.: US 7,078,431 B2
(45) Date of Patent: Jul. 18, 2006

(54) 1,3-BIS-(SUBSTITUTED-PHENYL)-2-PROPEN-1-ONES AND THEIR USE TO TREAT VCAM-1 MEDIATED DISORDERS

(75) Inventors: Charles Q. Meng, Alpharetta, GA (US); Liming Ni, Duluth, GA (US); James A. Sikorski, Alpharetta, GA (US); Lee K. Hoong, Suwanee, GA (US)

(73) Assignee: Atherogenics, Inc., Alpharetta, GA (US)

( * ) Notice: Subject to any disclaimer, the term of this patent is extended or adjusted under 35 U.S.C. 154(b) by 60 days.

(21) Appl. No.: 10/443,470

(22) Filed: May 21, 2003

(65) Prior Publication Data

US 2003/0236298 A1 Dec. 25, 2003

Related U.S. Application Data

(63) Continuation of application No. 09/886,348, filed on Jun. 20, 2001, now Pat. No. 6,608,101.
(60) Provisional application No. 60/255,934, filed on Dec. 15, 2000, and provisional application No. 60/212,769, filed on Jun. 20, 2000.

(51) Int. Cl.
*A61K 31/38* (2006.01)
*A61K 31/36* (2006.01)
*A61K 31/435* (2006.01)
*C07D 409/00* (2006.01)
*C07C 49/213* (2006.01)

(52) U.S. Cl. ............... 514/438; 514/444; 514/464; 514/342; 514/277; 514/678; 514/679; 549/78; 549/58; 549/444; 549/60; 546/280.4; 546/340; 568/308; 568/325

(58) Field of Classification Search ............... 549/78, 549/58, 444, 60; 514/444, 438, 464, 342, 514/277, 678, 679; 546/340, 280.4; 568/308, 568/325
See application file for complete search history.

(56) References Cited

U.S. PATENT DOCUMENTS

| | | | |
|---|---|---|---|
| 3,862,176 A | 1/1975 | Fauran et al. | |
| 4,085,135 A | 4/1978 | Kyogoku et al. | |
| 4,855,438 A | 8/1989 | Kaulen et al. | |
| 4,904,697 A | 2/1990 | Sunkara et al. | |
| 5,155,250 A | 10/1992 | Parker et al. | |
| 5,217,999 A | 6/1993 | Levitzki et al. | |
| 5,380,747 A | 1/1995 | Medford et al. | |
| 5,608,095 A | 3/1997 | Parker et al. | |
| 5,744,614 A | 4/1998 | Merkle et al. | |
| 5,750,351 A | 5/1998 | Medford et al. | |
| 5,773,209 A | 6/1998 | Medford et al. | |
| 5,773,231 A | 6/1998 | Medford et al. | |
| 5,783,596 A | 7/1998 | Medford et al. | |
| 5,792,787 A | 8/1998 | Medford et al. | |
| 5,807,884 A | 9/1998 | Medford et al. | |
| 5,808,137 A | 9/1998 | Bombardelli et al. | |
| 5,811,449 A | 9/1998 | Medford et al. | |
| 5,821,260 A | 10/1998 | Medford et al. | |
| 5,846,959 A | 12/1998 | Medford et al. | |
| 5,877,203 A | 3/1999 | Medford et al. | |
| 5,951,541 A | 9/1999 | Simpson et al. | |
| 6,046,212 A * | 4/2000 | Zwaagstra et al. | 514/311 |
| 6,423,740 B1 | 7/2002 | Bombardelli et al. | |
| 6,562,851 B1 * | 5/2003 | Clark et al. | 514/375 |
| 6,566,095 B1 * | 5/2003 | Markham et al. | 435/69.1 |
| 6,579,882 B1 * | 6/2003 | Stewart et al. | 514/260.1 |
| 6,583,139 B1 * | 6/2003 | Thorsett et al. | 514/227.5 |
| 6,596,687 B1 * | 7/2003 | Lin et al. | 514/2 |
| 6,608,069 B1 * | 8/2003 | Daluge et al. | 514/263.22 |
| 6,617,352 B1 * | 9/2003 | Somers | 514/543 |
| 6,624,196 B1 * | 9/2003 | Purchase et al. | 514/567 |

FOREIGN PATENT DOCUMENTS

| | | |
|---|---|---|
| EP | 0 307 762 | 3/1989 |
| FR | 2175634 | 10/1973 |
| GB | 1408754 | 10/1975 |
| JP | 63010720 | 1/1988 |
| JP | 4-217621 | 8/1992 |
| JP | 6-092950 | 4/1994 |
| JP | 6-116206 | 4/1994 |
| JP | 7-330814 | 12/1995 |
| WO | WO 95/15760 | 6/1995 |
| WO | WO 96/20936 | 7/1996 |
| WO | WO 97/12613 | 4/1997 |
| WO | WO 98/23581 | 6/1998 |
| WO | WO 98/51289 | 11/1998 |
| WO | WO 99/0014 | 1/1999 |
| WO | WO 98/51662 | 11/1999 |
| WO | WO 00/47554 | 8/2000 |

OTHER PUBLICATIONS

Abraham, W., et al., "Blockade of Late–phase Airway Responses and Airway Hyperresponsiveness in Allergic Sheep with a Small–molecule Peptide Inhibitor of VLA–4," *Am. J. Respir. Crit. Care Med.*, (1997), 156, 696–703.

(Continued)

*Primary Examiner*—Deborah C. Lambkin
(74) *Attorney, Agent, or Firm*—Sherry M. Knowles, Esq.; King & Spalding LLP

(57) ABSTRACT

It has been discovered certain 1,3-bis-(substituted-phenyl)-2-propen-1-ones, including compounds of formula (I) inhibit the expression of VCAM-1, and thus can be used to treat a patient with a disorder mediated by VCAM-1. Examples of inflammatory disorders that are mediated by VCAM-1 include, but are not limited to arthritis, asthma, dermatitis, cystic fibrosis, post transplantation late and chronic solid organ rejection, multiple sclerosis, systemic lupus erythematosis, inflammatory bowel diseases, autoimmune diabetes, diabetic retinopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

73 Claims, 9 Drawing Sheets

OTHER PUBLICATIONS

Albertini, et al., "Increase in Serum Levels of Adhesion Glycoprpteins in NIDDM Effect of Intensive Insulin Treatment," *Diabetologia*, (1996), 39, A240.

Bakhite, E., et al., "Synthesis and Application of Some New Oxazole Derivatives as Antimicrobial Agents," J. Chem. Tech. *Biotech.*, (1992), 55, 157–161.

Baraczka, K., et al., "A Study Of Increased Levels Of Soluble Vasular Cell Adhesion Molecule–1 (sVCAM–1) In The Cerebrospinal Fluid Of Patients With Multiple Sclerosis And systemic Lupus Erythematosus," *Acta. Neurol. Scand.*, (1999), 99, 95–99.

Belmont, et al., "Up–Regulation of Endothelial Cell Adhesion Molecules Characterizes Disease Activity in Systemic Lupus Erythematosus," *Arthritis & Rheumatism*,(1994), 37(3), 376–383.

Boratynska, M., et al., :Soluble cell adhesion molecules in chronic renal graft rejection, *Pol. Arch. Med. Wewn*, (1998), 100, 410–410.

Bousquet, et al., "Eosinophilic Inflammation in Asthma" *N. Engl. J. Med.*, (1990), 323(15), .

Braunstahl, G.J., et al., "Nasal allergen provocation induces adhesion molecule expression and tissue eosinophilia in upper and lower airways," *J. Allergy Clin. Immunol.*, (2001), 107, 469–476.

Calliste et al., "Chalcones: Structural Requirements for Antioxidant, Estrogenic and Antiproliferative Activities," *Anticancer Research*, (2001), 21, 3949–3956.

Cheng et al., "Broussochalcone A, a potent antioxidant and effective suppressor of inducible nitric oxide synthase in lipoplysaccharide–activated macrophages," *Biochemical Pharmacology*, (2001), 61, 939–946.

Cosimi, et al., "In Vivo Effects of Monoclonal Antibody to ICAM–1 (CD54) in Nonhuman Primates with Renal Allografts," *J. Immunol.*, (1990), 144(12), 4604–4612.

Dimmock, et al., "Bioactivities of Chalcones," *Current Medicinal Chemistry*, (1999), 6, 1125–1149.

Dimmock et al., "Cytotoxic Activities of Mannich Bases of Chalcones and Related Compounds," *J. Med. Chem.*, (1998), 41, 7, 1014–1026.

Dinkova–Kostova, et al., "Potency of Michael reaction acceptors as inducers of enzymes that protect against carcinogenesis depends on their reactivity with sulfhydryl groups," *Proc. Natl. Acad. Sci. U.S.A.*, (Mar. 13, 2001), 98(6), 3404–3409.

Elovaara, et al., "Adhesion Moleules in Multiple Sclerosis," *Arch. Neurol.*, (2000), 57, 546–551.

Enghofer, et al., "Vasular Cell Adhesion Molecule 1 Mediates Islet Lymphocyte Adhesion in Diabetic Insulitls in Mice," *Diabetologia*, (1996), 39, A97.

Frigerio, S.,et al., "Cerebrospinal fluid thrombomodulin and sVCAM–1 in different clinical stages of multiple sclerosis patients, " *Neuroimmunol.*, (1998), 87, 88–93.

Furuzawa–Carballeda, et al., "Interleukin–8, interleukin–10, intercellular Adhesion Molecule–1 and Vascular Cell Adhesion Molecule–1 Expression Levels are Higher in Synovial Tissue for Patients with Rheumatoid Arthritis than in Osteoarthritis," *Scand. J. Immunol.*, (1999), 50,215–222.

Goeke, et al., "Elevation of Soluble VCAM–1 in the Serum of Patients with Inflammatory Bowel Disease," *Gastroenterology*, (1994), 106, A689.

Goggins, et al., "Serum VCAM–1 reflects the grade of intestinal inflammation in patients with Crohn's disease," *Gastroenterology*, (1995), 108, A825.

Göke, et al., "Elevated serum concentrations of soluble selectin and immunoglobulin type adhesion molecules in patients with inflammatory bowel disease," *J. Gasterokenterol.*, (1997), 32, 480–486.

Gordon, et al., "Adhesion Molecule Expression in Inflammatory Bowel Disease (IBD) Patients Treated with Natalizumab (Antegrentm), a Humanized Antibody to A2 Integrin" *Gastroenterology*, (2000), 118 (No. 4, Suppl 2), A344.

Gosset, P., et al., "Expression of E–Selection, ICAM–1 and VCAM–1 on Bronchial Biopsies from Allergic an Non–Allergic Patients," *Int. Arch. Allergy Immunol.*, (1995), 106, 69–77.

Groves, R.E., et al., "Vascular cell adhesion molecule–1: Expression in normal and diseased skin and regulation in vivo by interferon gamma," *J. Am. Acad. Dermatol.*, (1993), 29, 67–72.

Grünbaum et al., "Nucleophilic Attacks on Carbon–Carbon Double Bonds. Part X. Nucleophile–catalysed *cis–trans* Isomerisation of *cis*–4–Nitrochalcone and of Diethyl Maleate in 95% Ethanol," *J. Chem. Soc.*, (1996), Section B, 1133–1137.

Hacken, N.H., et al., "Vascular cell adhesion molecules in nocturnal asthma: a possible role for VCAM–1 in ongoing airway wall inflammation," *Clin. Exp. Allergy*, (1998), 29, 1518–1525.

Hart, et al., "Coronary Endothelial Cell VCAM–1 Expression is Enhanced in the Diabetic Mouse Heart," *FASEB J.*, (1997), 11(3), A340.

Herencia, et al., "Synthesis and Anti–inflammatory activity of chalcone derivatives," *Synthesis and Anti–flammatory Activity of Chalcone Derivatives, Bioorganic & Medical Chemistry Letters*, (1998), 8, 1169–1174.

Herencia et al., "Novel anti–inflammatory chalcone derivatives inhibit the induction of nitric oxide synthase and cyclooxygenase–2 in mouse peritoneal macrophages," *FEBS Letters*, (1999), 453, 129–134.

Hsieh, et al., "Synthesis and Anti–inflammatory Effect of Chalcones,z" *J. Pharm. Pharmacol.*, (2000), 52, 163–171.

Ikeda, y., et al., "Relationship between lupus nephritis activity and the serum level of soluble VCAM–1," *Lupus*, (1998), 7, 347–354.

Issekeutz, et al., "T Lymphocyte Migration to Arthritic Joints and Dermal Inflammation in the Rat: Differing Migration Patterns and the Involvement of VLA–4," *Clinical Immunol. Immunopathol.*, (1991), 61, 436–447.

Jones, et al., "Adhesion molecules in inflammatory bowel disease," *Gut*, (1995), 36, 724–730.

Jones, S.M., et al., "VCAM–1 expression on endothelium in lesions from cutaneous lupus erythematosus is increased compared with systemic and localized scleroderma," *British J. Dermatol.*, (1996), 135, 678–686.

Kallmann., et al., "Cytokine–induced modulation of cellular adhesion to human cerebral endothelial cells is mediated by soluble vascular cell adhesion molecule–1,"*Brain*, (2000), 123, 687–697.

Kaplanski, G., et al., "Increased soluble vascular cell adhesion molecule 1 concentration in patients with primary or systemic lupus erythematosus–related antiphospholipid syndrome," *Arthritis & Rheumatism*, (2000), 43(1), 55–64.

Kitani, A., et al., "Soluble VCAM–1 induces Chemotaxis of Jurkat and Synovial Fluid T Cells Bearing High Affinity Very Late Antigen–4," *U. Immun.*, (1996), 161, 4931–4938.

Koga, M., et al., "Relationship Between Circulating Vascular Cell Adhesion Molecule–1 and Microvascular Complications in Type 2 Diabetes Mellitus," *Diabet. Med.*, (1998), 15(98), 661–667.

Koizumi, A., et al., "Elevation of serum soluble vascular cell adhesion molecule–1 (sVCAM–1) levels in bronchial asthma," Clin. Exo. Immunol., (1995), 101, 468–73.

Kolopp–Sarda, M.N., et al., "Longitudinal Study of Rheumatoid Arthritis Patients Discloses Sustained Elevated Serum Level of Soluble CD016 (V–CAM)," *Clin. and Exp. Rheumatol.*, (2001), 29, 165–70.

Koskinen, P.K., et al., "Adhesion Molecule P–Selecting and Vascular Cell Adhesion Molecule–1 in Enhanced heard Allograft Arteriosclerosis in the Rat," *Circulation*, (1997), 95(1), 191–196.

Lai, K.N., et al., "Upregulation of Adhesion molecule Expression on Endothelial Cells by Anti–DNA Autoantibodies in Systemic Lupus Erythematosus," *Clin Immunol Immunopathol*, (1996), 81(3), 229–238.

Lee et al., "2', 5'–Dihydroxychalcone down–regulates endothelial connexin43 gap junctions and affects MAP kinase activation," *Toxicology*, (2002), 179, 51–60.

Lee, S.J. et al., "Adhesion molecule expression and regulation on cells of the central nervous system," *J. Neuroimmunol.*, (1998), 98, 77–78.

LI, P., et al., "NF–KB Regulations VCAM–1 Expression on Fibroblast–Like Synoviocytes," *J. Immunol.*, (2000), 164, 5990–7.

Lin et al., "Novel Antiplatelet Constituents from Formosan Moraceous Plants," *J. Nat. Prod.*, 1996, 59(9), 834–838.

Liu et al., "Antimalarial Alkoxylated and Hydrocylated Chalones: Structure–Activity Relationship Analysis," *J. Med. Chem.*, 2001, 44(25), 4443–4452.

Loftus, et al., "Colonic Expression of Cell Adhesion Molecules Correlates with Clinical and Histologic Severity in Ulcerative Colitis but not Crohn's Disease," *Gastroenterology*, (1995), 108(4), p. A684.

Lorini, et al., "Elevated Circulating Adhesion Molecules in Children and Adolescents Affected by Insulin–Dependent Diabetes Mellitus," *Hormone Research*, (1997), 48(suppl. 2), p. 153.

Marinova–Mutafcheia, L., et al., "A Comparative Study into the Mechanisms of Action of Anti–Tumor Necrosis Factor α, Anti–CD4, and combined Anti–tumor Necrosis Factor oα/Anti–CD4 Treatment in Early Collagen–Induces Arthritis," *Arthritis Rheum.*, (2000), 43(3), 638–644.

Matsuyama, et al., "The Role of VCAM–1 Molecule in the Pathogenesis of Rheumatoid Synovitis," *Hum. Cell*, (1996), 9, 187–192.

McHale, J.F., et al., "TNF–α and IL–1 Sequentially Induce Endothelial 1CAM–1 and VCAM–1 Expression in MRL/lpr Lupus–Prone Mice," *J. Immunol.*, (1996),. 163, 3993–4000.

Metzger, et al., "Anti–VLA–4 Antibody and CS–1 Peptide Inhibitor Modifies Airway Inflammation and Bronchial Airway Hyperresponsiveness in the Allergic Rabbit," *J. Allergy Clin. Immunol.*, (1994), 93(1), 183.

Miranda et al., "Prenylated chalcones and flavanones as inducers of quinone reductase in mouse Hepa 1c1c7 cells," *Cancer Letters*, (2000), 149, 21–29.

Moreles–Ducret, et al., "Vascular Cell Adhesion Molecule–1 Expression in Synovium and on Fibroblast–Like Synoviocytes," *J. Immunol.*, (1992), 149, 1424–1431.

Mrowka, C., et al., "Detection of circulating adhesion molecules ICAM–1, VCAM–1 and E–Selectin in Wegener's granulomatosis, systemic lupus erythematosus and chronic renal failure," *Clin. Nephrol.*, (1995), 53(5), 288–296.

Nakamura et al., "Synthesis and Biological Activities of Fluorinated Chalcone Derivatives," *Bioorganic & Medicinal Chemistry*, (2002), 10, 699–705.

Nielsen et al.,"Antileishmanial Calcones: Statistical Design, Synthesis, and Three–Dimensional Qualitative Structure–Activity Relationship Analysis," *J. Med. Chem.*, (1998), 41, 4819–4832.

Nielsen et a., "Modifications of the α, β–Double Bond in Chalcones only Marginally Affect the Antiprotozoal Activities," *Bioorganic & Medicinal Chemistry*, (1998), 6, 937–945.

Nikoloff, C., et al., "The Cytokine Network in Psoriasis," *Arch Dermatol.*, (1991), 127, 871–884.

O'Brien, et al., "Vascular Cell Adhesion Molecule–1 is Expressed in Human Coronary Atherosclerotic Plaques," *J. Clin. Invest.*, (1993), 92, 945–951.

Oguchi, S., et al., "Monoclonal Antibody Against Vascular Cell Adhesion Molecule–1 Inhibits Neointimal Formation after Periadventitial Carotid Artery Injury in Genetically Hypercholesterolemic Mice," *Arterioscler. Thromb. Vasc. Biol.*, (2000), 20, 1729–1736.

Ohkawara, Y., et al., "In Situ Expression of the Cell Adhesion Molecules in Bronchial Tissues from Asthmatics with Air Flow Limitation: In Vivo Evidence of VCAM–1/VLA–4 Interaction in Selective Eosinophil Infiltration," *Am. J. Respir. Cell Mol. Biol.*, (1995), 12, 4–12.

Orosz, C.G., et al., "Prevention of Acute Murine Cardiac Allograft Rejection: Anti–CD4 or Anti–Vascular Cell Adhesion Molecule One Monoclonal Antibodies Block Acute Rejection but Permit Persistent Graft–Reactive Alloimmunity and Chronic Tissue Remodeling," *J. Heart and Lung Transplantation*, (1997), 16, 889–904.

Orosz, C.G., et al., "Treatment with Anti–Vascular Cell Adhesion Molecule 1 Monoclonal Antibody Induces Long–Term Murine Cardiac Allograft Acceptance," *Transportation*, (1993), 56, 453–460.

Otsuki, et al., "Circulating Vascular Cell Adhesion Molecule–1 as a Useful Marker for Atherosclerosis in NIDDM Patients," *Diabetologia*, (1997), 40, A440.

Pallis, et al., "Distribution of cell adhesion molecules in skeletal muscle from patients with systemic lupus erythematosus," *Ann. Rheum. Dis.*, (1993), 52, 667–671.

Papa, N.D., et al., "Anti–endothelial cell IgG fractions from systemic lupus erythematosus patients bind to human endothelial cells and induce a pro–adhesive and a pro–inflammatory phenotype *in vitro*," *Lupus*, (1999), 8, 423–429.

Pelletier, R., et al., "Analysis of Inflammatory Endothelial Changes, including VCAM–1 Expression, in Murine Cardiac Grafts," *Transplatation*, (1993), 55(2), 315–320.

Pelletier, R., et al., "Importance of Endothelial VCAM–1 for Inflammatory Leukocytic Infiltration in Vivo," *J. Immunol.*, (1992), 149(7), 2473–2481.

Pelletier, R., et al., "Monoclonal Antibody to Anti–V-CAM–1 Interferes with Murine Cardiac Allograft Rejection," *Transplatation Proceedings*, (1993), 25(1), 839–841.

Pilewski, et al., "Cell Adhesion Molecules in Asthma: Homing, Activation, and Airway Remodeling," *Am. J. Respir. Cell. Mol. Biol.*, (1995), 12, 1–3.

Postigo, et al., "Increased Binding of Synovial T Lymphocytes from Rhematoid Arthritis to Endothelial–Leykocyte Adhesion Molecule–1 (ELAM–1) and Vascular Cell Adhesion Molecule–1 (VCAM–1)," *J. Clin. Invest..*, (1992), 89, 1445–1452.

Rabb, et al., "The Role of the Leukocyte Adhesion Molecules VLA–4, LFA–1, and Mac–1 in Allergic Airway Responses in the Rat," *Am. J. Respir. Care. Med.*, (1994), 149, 1186–1191.

Reickmann, P., et al., "Correlation of soluble adhesion molecules in blood and cerebrospinal fluid with magnetic resonance imaging activity in patients with multiple sclerosis," *Multi. Scler.*, (1998), 4, 178–182.

Santos., et al., "Applicability of the case–parent design in the etiological research of Type 1 diabeties in Chile and other genetically mixed populations," *Diabetes Res. Clin. Pract.*, (1999), 43, 143–6.

Schopf, R.E., et al., "Soluble intercellular adhesion molecule–1 levels in patients with psoriasis," *Br. J. Dermatol.*, (1993), 128, 34–37.

Scudla, V., et al., "Vascular Intercellular Adhesion Molecule–1 (VCAM–1)–a New Indicator of Activity of Systemic Lupus Erythematosus," *Vnitr. Lek*, (1997), 43, 307–311.

Solez K., et al., "Adhesion molecules and rejection of renal allgrafts," *Kidney International*, (1997), 51, 1476–1480.

Soriano, A., et al., "VCAM–1, but Not ICAM–1 or MAd-CAM–1, Immunoblokade Ameliorates DSS–Induces Colitis in Mice," *Lab. Invest.*, (2000), 80(10), 1541–1551.

Sundell, et al., "Suppression of VCAM–1 and MCP–1 Attenuates Atherosclerosis in LDL Receptor–knockout and ApoE–knockout Mouse Models," *Circulation*, (1999), 100(18), pp. 1–42.

Tanio, et al., "Differential Expression of the Cell Adhesion Molecules ICAM–1, VCAM–1, and E–Selectin in Normal and Posttransplantation Myocardium," *Circulation*, (1994), 89, 1760–1768.

Uyemura, K., et al., "The Cytokine Network in Lesional and Lesion–Free Psoriatic Skin in Characterized by a T–Helper Type 1 Cell–Mediated Response," *J. Invest. Dermatol.*, (1993), 101–701–705.

Van Dinther–Janssen, et al., "The VLA–4/VCAM–1 Pathway in Involved in Lymphocyte Adhesion to Endothelium in Rheumatoid Synovium," *J. Immunol.*, (1991), 147(12), 4207–4210.

Wagner, et al., "Increased Concentrations of Soluble E–Selection and V–Cam in Gestational Diabetes," *Diabetologia*, (1996), 39, p. A205.

Wagner, et al., "Putative Role of Adhesion Molecules in Metabolic Disorders," *Hormone and Metabolic Research*, (1997), 29, 627–630.

Wang et al., "Investigation of the inhibitory effect of broussochalcone A on respiratory burst in neutrophils," *European Journal of Pharmacology*, (1997), 320, 201–208.

Wang, S., et al., "IL–12 Dependent Vascular Cell Adhesion Molecule–1 Expression Contributes to Airway Eosinophilic Inflammation in a Mouse Model of Asthma–Like Reaction," *J. Immunol.*, (2001), 166, 2741–2749.

Wilkinson, et al., "Expression of Vascular Cell Adhesion Molecule–1 in Normal and Inflamed Synovium," *Lab. Invest.*, (1993), 68(1), 82–89.

Wu et al., "Antimalarial Activity of Ferrocenyl Chalcones," *Bioorganic & Medicinal Chemistry Letters*, (2002), 12, 2299–2302.

Wuthrich, et al., "Vascular cell adhesion molecule–1 (VCAM–1) expression in murine lupus nephritis," *Kidney Int.*, (1992), 42, 903–914.

Yamazaki et al., "Isoliquiritigenin suppresses pulmonary metastasis of mouse renal cell carcinoma," *Cancer Letters*, (2002), 183, 23–30.

Zembala, M., et al., "Cellular adhesion molecules changes is myocardium during first year post heart transplant," *Ann. of Transplant.*, (1998), 2, 16–9.

Zwaagstra, et al., "Synthesis and Structure–Activity Relationships of Carboxylated Chalcones: A Novel Series of CysLTI (LT4) Receptor Antagonists,"*J. Med. Chem.*, (1997), 40, 1075–1089.

* cited by examiner

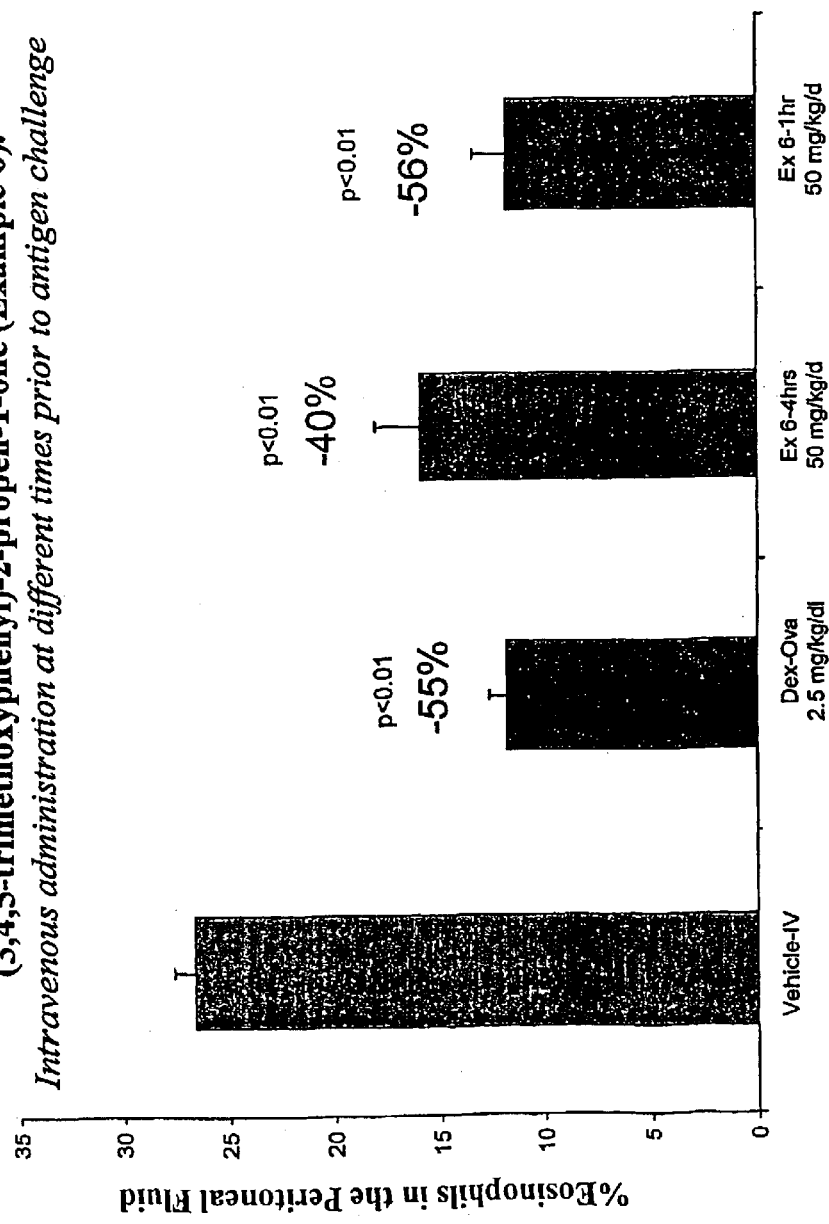
Figure 2. Inhibition of eosinophil recruitment in a murine model of allergen-induced peritonitis using 3-[5-(benzo[b]thien-2-yl)-2,4-dimethoxyphenyl]-1-(3,4,5-trimethoxyphenyl)-2-propen-1-one (Example 6). Intravenous administration at different times prior to antigen challenge

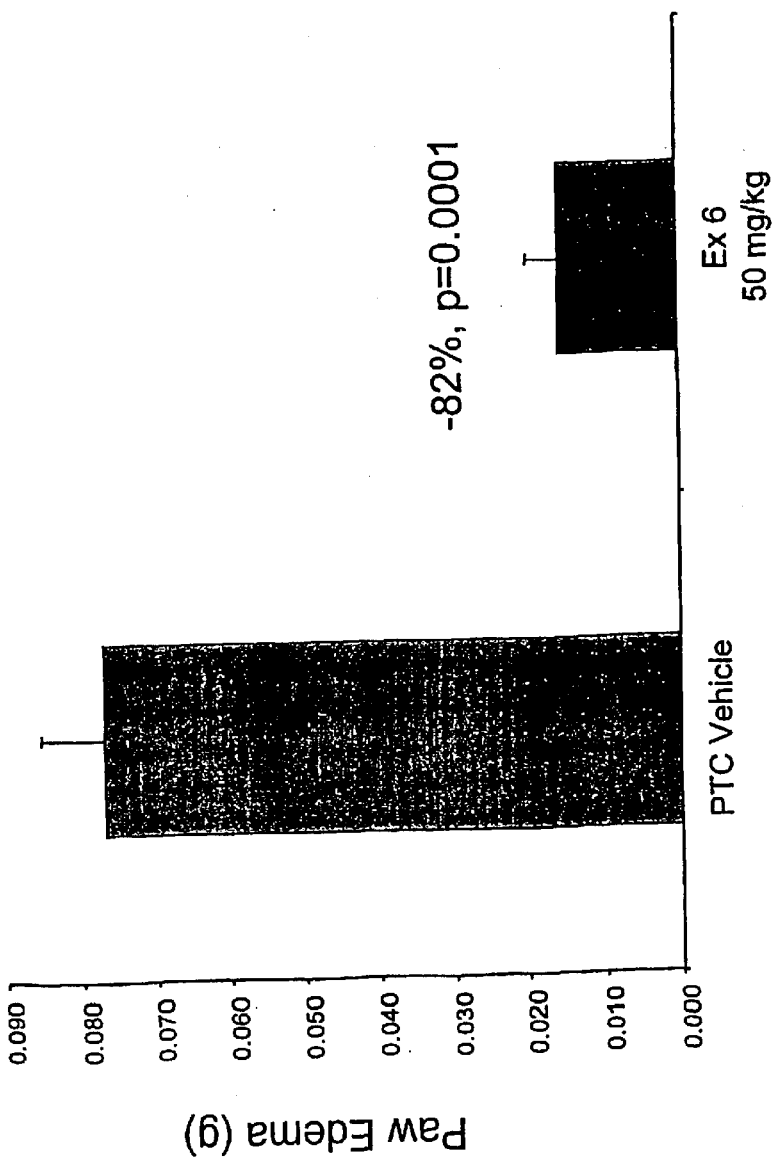
Figure 3. Inhibition of Paw Edema in a Mouse Model of Delayed Type Hypersensitivity using 3-[5-(benzo[b]thien-2-yl)-2,4-dimethoxyphenyl]-1-(3,4,5-trimethoxyphenyl)-2-propen-1-one (Example 6). Administered intraperitoneally -24, -2 and +6-hrs around the time of challenge.

1,3-BIS-(SUBSTITUTED-PHENYL)-2-PROPEN-1-ONES AND THEIR USE TO TREAT VCAM-1 MEDIATED DISORDERS

This application is a continuation U.S. Ser. No. 09/886,348, filed Jun. 20, 2001, which claims priority to U.S. Ser. No. 60/212,769, filed on Jun. 20, 2000, and U.S. Ser. No. 60/255,934 filed on Dec. 15, 2000, the disclosures of which are hereby incorporated by reference in their entirety.

The present invention includes novel heteroaryl or heterocyclic 1,3-bis-(substituted-phenyl)-2-propen-1-ones as well as methods and compositions for the treatment of disorders mediated by VCAM-1 or MCP-1 and for the treatment of inflammatory disorders generally that include the administration of a 1,3-bis-(substituted-phenyl)-2-propen-1-one that has at least one phenyl substituent that is an aryl, heteroaryl or heterocyclic moiety.

BACKGROUND OF THE INVENTION

Adhesion of leukocytes to the endothelium represents a fundamental, early event in a wide variety of inflammatory conditions, autoimmune disorders and bacterial and viral infections. Leukocyte recruitment to endothelium is mediated in part by the inducible expression of adhesion molecules on the surface of endothelial cells that interact with counterreceptors on immune cells. Endothelial cells determine which types of leukocytes are recruited by selectively expressing specific adhesion molecules, such as vascular cell adhesion molecule-1 (VCAM-1), intercellular adhesion molecule-1 (ICAM-1), and E-selectin. VCAM-1 binds to the integrin VLA-4 expressed on lymphocytes, monocytes, macrophages, eosinophils, and basophils but not neutrophils. This interaction facilitates the firm adhesion of these leukocytes to the endothelium. VCAM-1 is an inducible gene that is not expressed, or expressed at very low levels, in normal tissues. VCAM-1 is upregulated in a number of inflammatory diseases, including arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

Coronary heart disease (CHD), primarily as a result of atherosclerosis, remains the leading cause of death in industrialized countries. Atherosclerosis is a disease characterized by vascular inflammation, deposition of lipids in the arterial vessel wall and smooth muscle cell proliferation resulting in a narrowing of the vessel passages. In advanced stages of the disease atherosclerotic lesions can become unstable resulting in plaque rupture, thrombosis, myocardial infarction and ischemic heart disease. It is now well accepted that the initiating events in atherosclerosis are local injury to the arterial endothelium that results in the induction of VCAM-1 and recruitment of mononuclear leukocytes that express the integrin counterreceptor, VLA-4, (O'Brien, et al., J. Clin. Invest., 92: 945–951, 1993). Subsequent conversion of leukocytes to foamy macrophages results in the synthesis of a wide variety of inflammatory cytokines, growth factors, and chemoattractants that help propagate formation of the mature atheromatous plaque by further inducing endothelial activation, leukocyte recruitment, smooth muscle cell proliferation, and extracellular matrix deposition. Pharmacological inhibition of VCAM-1 expression has been shown to inhibit atherosclerosis in several animal models (Sundell et al., Circulation, 100: 42, 1999). A monoclonal antibody against VCAM-1 has also been shown to inhibit neointimal formation in a mouse model of arterial wall injury (Oguchi, S., et al., Arterioscler. Thromb. Vasc. Biol., 20: 1729–1736, 2000).

Asthma, which is increasing in prevalence and morbidity world-wide, is a chronic inflammatory disease characterized by lung eosinophilia and bronchial hyperreactivity. The interaction between VCAM-1 on lung endothelial cells and VLA-4, which is the integrin counterreceptor expressed on eosinophils, is thought to be important for selective eosinophil recruitment. Eosinophils have been considered an important effector cell in the pathogenesis of asthma and other allergic diseases. Activated eosinophils release proteins such as major basic protein (MBP) that have been demonstrated to induce bronchial hyperreactivity, one of the defining criteria of asthma (Bousquot, et al., N. Engl. J. Med., 323: 1033–1039, 1990). It has been demonstrated that VCAM-1 is markedly upregulated on human bronchial vascular endothelium of subjects with asthma who have air flow limitation, when compared with subjects without asthma (Pilewski, et al., Am. J. Respir. Cell Mol. Biol., 12, 1–3,1995; Ohkawara, Y., et al., Am. J. Respir. Cell Mol. Biol., 12, 4–12, 1995; Gosset, P., et al., Int. Arch. Allergy Immunol. 106: 69–77, 1995; Hacken, N. H., et al., Clin. Exp. Allergy, 28 (12): 1518–1525, 1998). An elevation in serum soluble VCAM-1 levels has also been demonstrated in patients undergoing a bronchial asthma attack compared with levels under stable conditions (Montefort, S., Koizumi, A., Clin. Exp. Immunol., 101: 468–73, 1995). Several animal studies further demonstrate a spatial and temporal association between VCAM-1 and asthma. In a mouse model of allergic asthma, VCAM-1 expression was shown to be induced by allergen challenge, and administration of an anti-VCAM-1 antibody was effective in inhibiting eosinophil infiltration that occurred in this model (Metzger, W. J., et al., J. Allergy Clin. Immunol., 93: 183, 1994). Further evidence for the importance of VCAM-1 in allergic asthma comes from work in IL-12 knockout mice. IL-12 knockout mice had fewer eosinophils and VCAM-1 expression than wildtype mice; however, administration of recombinant IL-12 at the time of ova sensitization and challenge restored lung VCAM-1 expression and eosinophilia (Wang, S., et al., J. Immunol., 166:2741–2749, 2001). There are several examples where blocking the integrin receptors for VCAM-1 have had positive effects on animal models of asthma (Rabb et al., Am. J. Respir. Care Med. 149: 1186–1191, 1994; Abraham, W, et al., Am. J. Respir. Crit. Care Med. 156: 696–703. 1997) further demonstrating the importance of VCAM-1/VLA-4 interactions in allergic inflammation. Eosinophils are also important effector cells in allergic rhinitis. VCAM-1 has been demonstrated to be upregulated 24 hrs after nasal allergen provocation in patients with seasonal allergic rhinitis but not in normal subjects (Braunstahl, G. J., et al., J. Allergy Clin. Immunol., 107: 469–476, 2001).

Rheumatoid arthritis (RA) is a clinical syndrome of unknown cause characterized by symmetric, polyarticular inflammation of synovial-lined joints. The role of adhesion molecules in the pathogenesis of rheumatoid arthritis (RA) has also been well documented, and VCAM-1 expression on synovial fibroblasts is a clinical hallmark of RA (Li, P., et al., J. Immunol. 164: 5990–7, 2000). VLA-4/VCAM-1 interactions may be the predominant mechanism for recruitment of leukocytes to the synovium (Dinther-Janssen, et al., J. Immunol. 147: 4207–4210, 1991; Issekeutz and Issekeutz, Clin. Immunol. Immunopathol. 61:436–447, 1991; Morales-Ducret et al., J. Immunol. 149:1424–1431, 1992; Postigo et al., J. Clin. Invest. 89:1445–1452, 1992; Matsuyama, T., et al, Hum. Cell, 9: 187–192,1996). In support of this, increased VCAM-1 expression has been found in RA synovial tissue compared with osteoarthritis and control tissue (Wilkinson et al., Lab. Invest. 69:82–88, 1993; Furuzawa-Carballeda, J., et al., Scand. J. Immunol. 50: 215–222; 1999). Soluble VCAM-1 is higher in RA patients than in control subjects (Kolopp-Sarda, M. N., et al., Clin. Exp. Rheumatol. 19: 165–70, 2001). Soluble VCAM-1 has been shown to be chemotactic for T cells (Kitani, A., et al., J. Immun. 161: 4931–8, 1998), and in addition to being a possible diagnostic marker for RA, may contribute to its pathogenesis by inducing migration and recruitment of T cells. VCAM-1 expressed on fibroblast-like synoviocytes has also been implicated in enhanced survival of activated synovial fluid B cells (Marinova, Mutafcheia, L., Arthritis Rheum. 43: 638–644, 2000) that may further contribute to RA pathogenesis.

Chronic inflammation and accompanying vascular complications and organ damage characterize systemic lupus erythematosis (SLE). Recent studies suggest that VCAM-1 plays a role in SLE. Expression of VCAM-1 is increased on dermal vessel endothelial cells in patients with active systematic lupus erythematosus (Jones, S. M., British J. Dermatol. 135: 678–686, 1996) and correlates with increased disease severity (Belmont et al., Arthritis Rheum. 37:376–383, 1994). SLE muscle samples with perivascular infiltrate have greater endothelial cell expression of VCAM-1 compared with SLE patients without a perivascular infiltrate or with control samples (Pallis et al., Ann. Rheum. Dis. 52:667–671, 1993). Increased expression of VCAM-1 has also been demonstrated in kidneys of lupus-prone MRL/1 pr mice compared to nonautoimmune strains and its expression increased with disease severity (McHale, J. F., et al., J. Immunol. 163: 3993–4000, 1999). VCAM-1 expression on mesangial cells in vitro can be stimulated by IL-1, TNF-$\alpha$, and INF$\gamma$ exposure as well as by anti-endothelial cell IgG fraction and anti-DNA autoantibodies from SLE patients (Wuthrich, Kidney Int. 42: 903–914, 1992; Papa, N. D., et al., Lupus, 8: 423–429, 1999; Lai, K. N., et al., Clin Immunol Immunopathol, 81: 229–238, 1996). Furthermore, soluble VCAM-1 is higher in SLE patients than in normal subjects (Mrowka, C., et al., Clin. Nephrol. 43: 288–296, 1995; Baraczka, K., et al., Acta. Neurol. Scand. 99: 95–99, 1999; Kaplanski, G., et al., Arthritis Rheumol. 43: 55–64, 2000; Ikeda, Y., Lupus, 7: 347–354, 1998) and correlates with disease activity (Scudla, V., Vnitr. Lek., 43: 307–311, 1997).

Increased VCAM-1 expression has also been demonstrated in solid organ transplant rejection. Acute transplant rejection occurs when the transplant recipient recognizes the grafted organ as "non-self" and mounts an immune response characterized by massive infiltration of immune cells, edema, and hemorrage that result in the death of the transplanted organ. Acute rejection occurs in a matter of hours or days and has been correlated with increased levels of VCAM-1 in tissues and in plasma (Tanio et al., Circulation, 89:1760–1768, 1994; Cosimi et al., J. Immunol. 144: 4604–4612, 1990; Pelletier, R., et al., Transplantation, 55: 315, 1992). A monoclonal antibody to VCAM-1 has been shown to inhibit cardiac allograft rejection in mice (Pelletier, R., J. Immunol., 149: 2473–2481, 1992; Pelletier, R., et al., Transplantation Proceedings, 25: 839–841, 1993; Orosz, C. G., et al., J. Heart and Lung Transplantation, 16: 889–904, 1997) and when given for 20 days can cause complete inhibition of rejection and long-term graft acceptance (Orosz C. G., et al., Transplantation, 56: 453–460, 1993). Chronic graft rejection also known as allograft vasculopathy is distinct from acute transplant rejection and is a leading cause of late graft loss after renal and heart transplantation. Histologically it is characterized by concentric neointimal growth within vessels that is largely due to smooth muscle migration and proliferation. It is thought to be the result of endothelial damage brought about by several factors including: ischemia-reperfusion injury, immune complexes, hypertension, hyperlipidemia and viruses. All of these factors have been associated with induction of VCAM-1 in endothelial cells. There is also a strong correlation of soluble and tissue VCAM-1 levels with chronic rejection (Boratynska, M.,. Pol. Arch. Med. Wewn, 100: 410–410, 1998; Zembala, M., et al., Ann. Transplant. 2: 16–9, 1998; Solez K., et al., Kidney International., 51: 1476–1480, 1997; Koskinen P. K., et al., Circulation, 95: 191–6, 1997).

Multiple sclerosis is a common demyelinating disorder of the central nervous system, causing patches of sclerosis (plaques) in the brain and spinal cord. It occurs in young adults and has protean clinical manifestations. It is well documented that VCAM-1 is expressed on brain microvascular endothelial cells in active lesions of multiple sclerosis (Lee S. J., et al., J. Neuroimmunol., 98: 77–88, 1998). Experimental therapy of experimental autoimmune encephalomyelitis, which is an animal model for multiple sclerosis, using antibodies against several adhesion molecules, including VCAM-1, clearly shows that adhesion molecules are critical for the pathogenesis of the disease (Benveniste et al., J. Neuroimmunol. 98:77–88, 1999). A time and dose dependent expression of VCAM-1 and release of soluble VCAM-1 were detected in cultures of human cerebral endothelial cells induced by TNF$\alpha$, but not in peripheral blood mononuclear cells (Kallmann et al., Brain, 123:687–697, 2000). Clinical data also show that adhesion molecules in blood and cerebrospinal fluid are up-regulated throughout the clinical spectrum of multiple sclerosis (Baraczka, K., et al., Acta. Neurol. Scand. 99: 95–99, 1999; Reickimann, P., et al., Mult. Scler., 4: 178–182, 1998; Frigerio, S., et al., J. Neuroimmunol., 87: 88–93, 1998) supporting the notion that therapies which interfere with cell adhesion molecules such as VCAM-1 may be beneficial in modifying this disease (Elovaara et al., Arch. Neurol. 57:546–551, 2000).

Diabetes mellitus is a metabolic disease in which carbohydrate utilization is reduced and that of lipid and protein is enhanced. Evidence has accumulated that increased levels of adhesion molecules may play a functional pathophysiological role in diabetes (Wagner and Jilma, Hormone and Metabolic Research, 29: 627–630, 1997; Kado, S., Diabetes Res. Clin. Pract., 46: 143–8, 1999). It is caused by an absolute or relative deficiency of insulin and is characterized by chronic hyperglycemia, glycosuria, water and electrolyte loss, ketoacidosis, and coma. Elevated circulating adhesion molecules including VCAM-1 have been detected in patients with diabetes and in experimental models of diabetes in animals (Lorini et al., Hormone Research, 48: 153, 1997; Otsuki et al., Diabetologia, 40: A440, 1997; Hart et al., FASEB J. 11:A340, 1997; Albertini et al., Diabetologia, 39: A240, 1996; Wagner et al., Diabetologia, 39: A205, 1996; Enghofer et al., Diabetologia, 39: A97, 1996; Koga M., Diabet. Med., 15: 661–667, 1998). In addition, complications of diabetes often include peripheral vasculopathies such as diabetic retinopathy and diabetic nephropathy. It is believed that adhesion of leukocytes to the peripheral vasculature plays a central role in the vasculopathies often associated with diabetes.

Crohn's disease, also known as regional enteritis, is a subacute chronic inflammatory condition of unknown cause, involving the internal ileum and less frequently other parts of the gastrointestinal tract. It is characterized by patchy deep ulcers that may cause fistulas, and narrowing and thickening of the bowel by fibrosis and lymphocytic infiltration. Ulcerative colitis is a chronic disease of unknown cause characterized by ulceration of the colon and rectum, with rectal bleeding, mucosal crypt abscesses, inflammatory pseudopolyps, abdominal pain, and diarrhea. It has been reported that serum VCAM-1 reflects the grade of intestinal inflammation in patients with Crohn's disease or ulcerative colitis (Jones, et al., Gut, 36: 724–30, 1995; Goggins et al., Gastroenterology, 108: A825, 1995; Goeke and Manns, Gastroenterology, 106: A689, 1994; Goeke et al., J. Gasterokenterol. 32:480–486, 1997; Loftus et al., Gastroenterology, 108: A684, 1995; Tahami et al., Gastroenterology, 118: A344, 2000). Antibodies to VCAM-1 have been shown to ameliorate experimentally-induced colitis in mice (Soriano, A., Lab. Invest. 80: 1541–1551, 2000).

Psoriasis is a chronic skin disease characterized by erythematous scaling plaques as a result of keratinocyte hyperplasia, influx of immune cells and endothelial activation (Nickoloff, B. J., et al., J. Invest. Dermatol., 127: 871–884, 1991). VCAM-1 is upregulated in psoriatic skin as compared to normal skin (Groves, R. W., J. Am. Acad. Dermatol., 29: 67–72, 1993; Uyemura, K., et al., J. Invest. Dermatol. 101: 701–705, 1993) and levels of circulating VCAM-1 correlate with disease activity (Schopf, R. E., Br. J. Dermatol., 128: 34–7, 1993).

U.S. Pat. Nos. 5,750,351; 5,807,884; 5,811,449; 5,846,959; 5,773,231, and 5,773,209 to Medford, et al., as well as the corresponding WO95/30415 to Emory University indicate that polyunsaturated fatty acids ("PUFAs") and their hydroperoxides ("ox-PUFAs"), which are important components of oxidatively modified low density lipoprotein (LDL), induce the expression of VCAM-1, but not intracellular adhesion molecule-1 (ICAM-1) or E-selectin in human aortic endothelial cells, through a mechanism that is not mediated by cytokines or other noncytokine signals. This is a fundamental discovery of an important and previously unknown biological pathway in VCAM-1 mediated immune responses. As non-limiting examples, linoleic acid, linolenic acid, arachidonic acid, linoleyl hydroperoxide (13-HPODE) and arachidonic hydroperoxide (15-HPETE) induce cell-surface gene expression of VCAM-1 but not ICAM-1 or E-selectin. Saturated fatty acids (such as stearic acid) and monounsaturated fatty acids (such as oleic acid) do not induce the expression of VCAM-1, ICAM-1 or E-selectin.

PCT WO 98/51662, filed by AtheroGenics, Inc. and listing as inventors Russell M. Medford, Patricia K. Somers, Lee K. Hoong, and Charles Q. Meng, claims priority to provisional application U.S. Ser. No. 60/047,020, filed on May 14, 1997. This application discloses the use of a broad group of compounds as cardiovascular protectants that exhibit at least one, and sometimes a composite profile, of reducing cholesterol, lowering LDL, and inhibiting the expression of VCAM-1.

U.S. Pat. No. 5,155,250 to Parker, et al. discloses that 2,6-dialkyl-4-silylphenols are antiatherosclerotic agents. The same compounds are disclosed as serum cholesterol lowering agents in PCT Publication No. WO 95/15760, published on Jun. 15, 1995. U.S. Pat. No. 5,608,095 to Parker, et al. discloses that alkylated-4-silyl-phenols inhibit the peroxidation of LDL, lower plasma cholesterol, and inhibit the expression of VCAM-1, and thus are useful in the treatment of atherosclerosis.

PCT WO 98/51289, which claims priority to provisional application U.S. Ser. No. 60/047,020, filed on May 14, 1997 by Emory University listing Patty Somers as sole inventor, discloses the use of a group of compounds as cardiovascular protectants and antiinflammatory agents which exhibit at least one, and sometimes a composite profile, of reducing cholesterol, lowering LDL, and inhibiting the expression of VCAM-1 and thus can be used as antiinflammatory and cardivascular treat agents.

U.S. Pat. Nos. 5,380,747; 5,792,787; 5,783,596; 5,750,351; 5,821,260; 5,807,884; 5,811,449; 5,846,959; 5,877,203; and 5,773,209 to Medford, et al., teach the use of dithiocarbamates of the general formula A—SC(S)—B for the treatment of cardiovascular and other inflammatory diseases. Examples include sodium pyrrolidine-N-carbodithioate, tri-sodium N,N-di(carboxymethyl)-N-carbodithioate, and sodium N,N-diethyl-N-carbodithioate. The patents teach that the compounds inhibit the expression of VCAM-1.

PCT WO 98/23581 discloses the use of benzamidoaldehydes and their use as cysteine protease inhibitors.

PCT WO 97/12613 of Comicelli et al. discloses compounds for the inhibition of 15-lipogenase to treat and prevent inflammation or atherosclerosis. Compounds disclosed include benzopyranoindole, benzimidazole, catacholes, benzoxadiazines, benzo[a]phenothiazine, or related compounds thereof.

Japanese Patent No. 06092950 to Masahiko et al. discloses preparation of epoxy compounds wherein electron deficient olefins such as acylstyrene derivatives, styrene derivatives, and cyclohexenone derivatives are efficiently oxidized by a hydrogen peroxide derivative in the presence of a primary or secondary amine in an organic solvent to give said epoxides which are useful intermediates for pharmaceutical and flavoring materials.

U.S. Pat. No. 5,217,999 to Levitzki et al. discloses substituted styrene compound as a method of inhibiting cell proliferation.

Chalcone (1,3-bis-aromatic-prop-2-en-1-ones) compounds are natural products related to flavonoids. PCT WO 99/00114 (PCT/DK98/00283) discloses the use of certain chalcones, 1,3-bis-aromatic-propan-1-ones (dihydrochalcones), and 1,3-bisaromatic-prop-2-yn-1-ones for the preparation of pharmaceutical compositions for the treatment of prophylaxis of a number of serious diseases including i) conditions relating to harmful effects of inflammatory cytokines, ii) conditions involving infection by Helicobacter species, iii) conditions involving infections by viruses, iv) neoplastic disorders, and v) conditions cause by microorganisms or parasites.

PCT WO 00/47554 filed by Cor Therapeutics describes a broad class of substituted unsaturated compounds for use as antithrombotic agents.

PCT 96/20936 (PCT/KR95/00183) discloses thiazolidin-4-one derivatives of the formula:

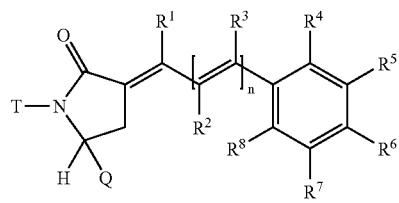

which act as PAF antagonists or 5-lipoxygenase inhibitors. The compounds are used in the prevention and treatment of inflammatory and allergic disorders mediated by platelet-activating factor and/or leukotrienes.

U.S. Pat. No. 4,085,135 discloses 2'-(carboxymethoxy)-chalcones with antigastric and antiduodenal ulcer activities.

U.S. Pat. No. 5,744,614 to Merkle et al. discloses a process for preparing 3,5-diarylpyrazoles and various derivatives thereof by reacting hydrazine hydrate with 1,3-diaryipropenone in the presence of sulfuric acid and an iodine compound.

U.S. Pat. No. 5,951,541 to Wehlage et al. discloses the use of salts of aromatic hydroxy compounds, such as (hydroxyaryl)alkenone salts, as brighteners in aqueous acidic electroplating baths. In addition the invention discloses that such compounds have a lower vapor pressure than the known brighteners, as a single substance and in the electroplating baths,in order to avoid losses of substance. They also have high water solubility properties.

Japanese Patent No. 07330814 to Shigeki et al. discloses benzylacetophenone compounds as photoinitiator compounds.

Japanese Patent No. 04217621 to Tomomi discloses siloxane chalcone derivatives in sunscreens.

U.S. Pat. No. 4,085,135 to Kyogoku et al. discloses a process for preparation of 2'-(carboxymethoxy)-chalcones having antigastric and anti duodenal activities with low toxicity and high absorptive ratio in the body. This patent suggests that the high absorptive ratio in the body is due to the 2'-carboxymethoxy group attached to the chalcone derivative.

U.S. Pat. No. 4,855,438 discloses the process for preparation of optically active 2-hydroxyethylazole derivatives which have fungicidal and plant growth-regulating action by reacting an α-β-unsaturated ketone which could include a chalcone or a chalcone derivative with an enantiomerically pure oxathiolane in the presence of a strongly basic organometallic compound and at temperatures ranging from −80 to 120° C.

European Patent No 307762 assigned to Hofmann-La Roche discloses substituted phenyl chalcones.

E. Bakhite et al. in J. Chem. Tech. Biotech. 1992, 55, 157–161, have disclosed a process for the preparation of some phenyloxazole derivatives of chalcone by condensing 5-(p-acetylphenyl)-2-phenyloxazole with aromatic aldehydes.

Herencia, et al., in Synthesis and Anti-inflammatory Activity of Chalcone Derivatives, Bioorganic & Medicinal Chemistry Letters 8 (1998) 1169–1174, discloses certain chalcone derivatives with anti-inflammatory activity.

Hsieh, et al., Synthesis and Antiinflammatory Effect of Chalcones, J. Pharm. Pharmacol. 2000, 52; 163–171 describes that certain chalcones have potent antiinflammatory activity.

Zwaagstra, et al., Synthesis and Structure-Activity Relationships of Carboxylated Chalcones: A Novel Series of CysLT1 (LT4) Receptor Antagonists; J. Med. Chem., 1997, 40, 1075–1089 discloses that in a series of 2-, 3-, and 4-(2-quinolinylmethoxy)- and 3- and 4-[2-(2-quinolinyl)ethenyl]-substituted, 2', 3', 4', or 5' carboxylated chalcones, certain compounds are CysLT1 receptor antagonists.

JP 63010720 to Nippon Kayaku Co., LTD discloses that chalcone derivatives of the following formula (wherein R1 and R2 are hydrogen or alkyl, and m and n are 0–3) are 5-lipoxygenase inhibitors and can be used in treating allergies.

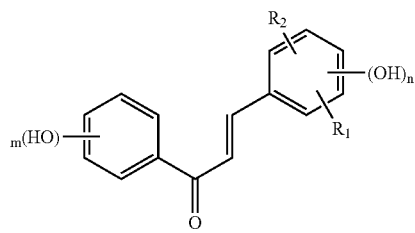

JP 06116206 to Morinaga Milk Industry Co. Ltd, Japan, discloses chalcones of the following structure as 5-lipoxygenase inhibitors, wherein R is acyl and R1–R5 are hydrogen, lower alkyl, lower alkoxy or halo, and specifically that in which R is acyl and R1–R5 are hydrogen.

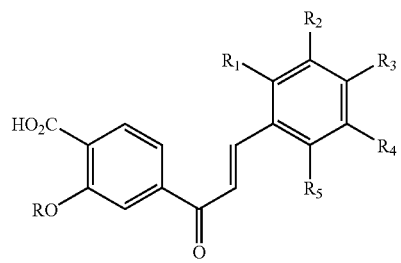

I R = Ac
II R•R$_5$ = H

U.S. Pat. No. 6,046,212 to Kowa Co. Ltd. discloses heterocyclic ring-containing chalcones of the following formula as antiallergic agents, wherein A represents a substituted or unsubstituted phenyl group, a substituted or unsubstituted naphthyl group, or a group:

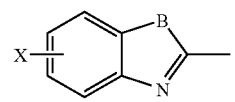

in which X represents a hydrogen or halogen atom or a hydroxyl, lower alkyl or lower alkoxyl group and B represents —CH═CH—, —N(R6)—, R6 is a lower alkyl group or a lower alkoxyalkyl group, —O— or —S—; W represents —CH═CH— or —CH2O—, and R1–5 is the same or different and each independently represent a hydrogen or halogen atom, a hydroxyl, a lower alkyl, lower alkoxyl, carboxyl, cyano, alkyloxycarbonyl or tetrazolyl group, a group —CONHR7 in which R7 represents a hydrogen atom or a lower alkyl group, or a group —O(CH2)n R8 in which R8 represents a carboxyl, alkyloxycarbonyl or tetrazolyl group and n is from 1 to 4, with the proviso that at least one of the groups R1–5 represents a carboxyl, cyano, alkyloxycarbonyl or tetrazolyl group, the group —CONHR7 or the group —O(CH2)nR8; or a salt or solvate thereof.

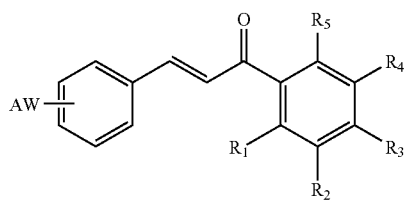

Reported bioactivies of chalcones have been reviewed by Dimmock, et al., in Bioactivities of Chalcones, Current Medicinal Chemistry 1999, 6, 1125–1149.

Given that VCAM-1 is a mediator of chronic inflammatory disorders, it is a goal of the present work to identify new compounds, compositions and methods that can inhibit the expression of VCAM-1. A more general goal is to identify selective compounds and methods for suppressing the expression of redox sensitive genes or activating redox sensitive genes that are suppressed.

It is therefore an object of the present invention to provide new compounds for the treatment of disorders mediated by VCAM-1.

It is also an object to provide new pharmaceutical compositions for the treatment of diseases and disorders mediated by the expression of VCAM-1.

It is a further object of the invention to provide compounds and methods of treating disorders and diseases mediated by VCAM-1, including cardiovascular and inflammatory diseases.

It is another object of the invention to provide compounds, compositions and methods to treat arthritis.

It is yet another object of the invention to provide compounds, compositions and methods to treat asthma.

It is another object of the invention to provide compounds, methods and compositions to inhibit the progression of atherosclerosis.

It is still another object of the invention to provide compounds, compositions, and methods to treat or prevent transplant rejection.

It is a further object of the present invention to provide compounds, methods and compositions for the treatment of lupus.

It is a further object of the present invention to provide compounds, methods and compositions for the treatment of inflammatory bowel disease.

It is a further object of the present invention to provide compounds, methods and compositions for the treatment of autoimmune diabetes.

It is a further object of the present invention to provide compounds, methods and compositions for the treatment of multiple sclerosis.

It is a further object of the present invention to provide compounds, methods and compositions for the treatment of diabetic retinopathy.

It is a further object of the present invention to provide compounds, methods and compositions for the treatment of rhinitis.

It is a further object of the present invention to provide compounds, methods and compositions for the treatment of ischemia-reperfusion injury.

It is a further object of the present invention to provide compounds, methods and compositions for the treatment of post-angioplasty restenosis.

It is a further object of the present invention to provide compounds, methods and compositions for the treatment of chronic obstructive pulmonary disease (COPD).

It is a further object of the present invention to provide compounds, methods and compositions for the treatment of glomerulonephritis.

It is a further object of the present invention to provide compounds, methods and compositions for the treatment of Graves disease.

It is a further object of the present invention to provide compounds, methods and compositions for the treatment of gastrointestinal allergies.

It is a further object of the present invention to provide compounds, methods and compositions for the treatment of conjunctivitis.

It is a further object of the present invention to provide compounds, methods and compositions for the treatment of dermatitis.

It is a further object of the present invention to provide compounds, methods and compositions for the treatment of psoriasis.

SUMMARY OF THE INVENTION

It has been discovered certain 1,3-bis-(substituted-phenyl)-2-propen-1-ones, including compounds of formula (I) inhibit the expression of VCAM-1, and thus can be used to treat a patient with a disorder mediated by VCAM-1. Examples of inflammatory disorders that are mediated by VCAM-1 include, but are not limited to arthritis, asthma, dermatitis, cystic fibrosis, post transplantation late and chronic solid organ rejection, multiple sclerosis, systemic lupus erythematosis, inflammatory bowel diseases, autoimmune diabetes, diabetic retinopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

The compounds disclosed herein can also be used in the treatment of inflammatory skin diseases that are mediated by VCAM-1, as well as human endothelial disorders that are mediated by VCAM-1, which include, but are not limited to psoriasis, dermatitis, including eczematous dermatitis, Kaposi's sarcoma, multiple sclerosis, as well as proliferative disorders of smooth muscle cells.

In yet another embodiment, the compounds disclosed herein can be selected to treat anti-inflammatory conditions that are mediated by mononuclear leucocytes.

In one embodiment, the compounds of the present invention are selected for the prevention or treatment of tissue or organ transplant rejection. Treatment and prevention of organ or tissue transplant rejection includes, but is not limited to treatment of recipients of heart, lung, combined heart-lung, liver, kidney, pancreatic, skin, spleen, small bowel, or corneal transplants. The compounds can also be used in the prevention or treatment of graft-versus-host disease, such as sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

In addition to inhibiting the expression of VCAM-1, the 1,3-bis-(substituted-phenyl)-2-propen-1-ones have the additional properties of inhibiting monocyte chemoattractant protein-1 (MCP-1) and smooth muscle proliferation. MCP-1 is a chemoattractant protein produced by endothelial cells, smooth muscle cells as well as macrophages. MCP-1 promotes integrin activation on endothelial cells thereby facilitating adhesion of leukocytes to VCAM-1, and MCP-1 is a chemoattractant for monocytes. MCP-1 has been shown to play a role in leukocyte recruitment in a number of chronic inflammatory diseases including atherosclerosis, rheumatoid arthritis, and asthma. Its expression is upregulated in these diseases and as such inhibition of MCP-1 expression represents a desirable property of anti-inflammatory therapeutics. Furthermore, smooth muscle cell hyperplasia and resulting tissue remodeling and decreased organ function is yet another characteristic of many chronic inflammatory diseases including atherosclerosis, chronic transplant rejection and asthma. Inhibition of the hyperproliferation of smooth muscle cells is another desirable property for therapeutic compounds.

In one embodiment, the invention provides a compound of the formula (I)

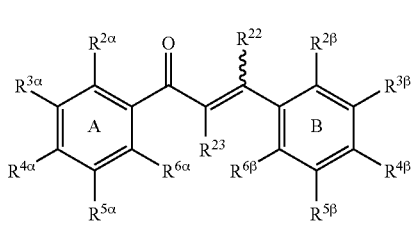

or its pharmaceutically acceptable salt, wherein:
i) the wavy line indicates that the compound can be in the form of the E or Z isomer;
ii) R22 and R23 are independently hydrogen or (C1–C4) alkyl;
iii) R2α, R3α, R4α, R5α, R6α, R2β, R3β, R4β, R5β and R6β are independently
iv) hydrogen, alkyl, carbocycle, aryl, heteroaryl, heterocycle, cycloalkyl, alkoxy, aryloxy, arylalkoxy, heteroaryloxy, heteroarylalkoxy, alkylthio, alkylamino, aminoalkyl, haloalkylthio, acyl, haloalkyl, aryloxy, amido, acylamino, amino, dialkylamino, aminodialkyl, trifluoroalkoxy, alkylsulfonyl, haloalkylsulfonyl, aminocarbonyl, alkenyl, alkynyl, halogen, hydroxyl, thiol, cyano, nitro, sulfonic acid, sulfonate, sulfate, sulfinic acid, sulfenic acid, sulfamide, sulfonamide, sulfoxide, metal sulfinate, phosphate, phosphonate, metal phosphonate, phosphinate, alditol, carbohydrate, amino acid, OC(R1)2CO2H, SC(R1)2CO2H, NHCHR1CO2H, CO—R2, CO2R1, polyoxyalkylene, polyol alkyl, oxyalkylamino, alkylcarbonylalkyl, lower alkyl S(O)-lower alkyl, lower alkyl-S(O)2-lower alkyl; hydroxyalkyl, aralkoxy, heteroaryl lower alkoxy, heterocyclo lower alkoxy, heteroaryloxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, any of which can be optionally substituted with a moiety that does not adversely affect the biological properties of the molecule; —C(O)(CH2)2CO2—M+, —SO3M+, or -lower alkyl-O—R, wherein R is PO2(OH)—M+, PO3(OH)—M+ or —SO3M+, wherein M+ is a pharmaceutically acceptable cation; -lower alkylcarbonyl-lower alkyl; carboxy lower alkyl; -lower alkylamino-lower alkyl; N,N-di-substituted amino lower alkyl-, wherein the substituents each independently represent lower alkyl;
v) R1 is H, lower alkyl, an optionally substituted carbocycle, aryl, heteroaryl, heterocycle, alkylaryl, alkylheteroaryl, alkylheteroaryl or alkylheterocycle;
vi) R2 is an optionally substituted alkyl, alkenyl, alkynyl, aryl, carbocycle, aryl, heteroaryl, heterocycle, alkylaryl, alkylheteroaryl, alkylheteroaryl or alkylheterocycle;
vii) alternatively, R22 and R6α or R23 and R6α can join together to form a bridged carbocycle, aryl, heterocycle or heteroaromatic;

viii) R2α and R3α, R3α and R4α, R4α and R5α, R5α and R6α, R2β and R3β, R3β and R4β, R4β and R5β or R5β and R6β can independently join to form a bridged compound selected from the group consisting of an optionally substituted carbocycle, an optionally substituted cycloalkenyl, an optionally substituted cycloalkylcarbonyl, an optionally substituted cycloalkenylcarbonyl; an optionally substituted aryl, an optionally substituted heterocylic or an optionally substituted heteroaromatic, or alkylenedioxy or wherein the ring can include a carbonyl, cyclic ester, amide, amine, sulfonate, or phosphonate;
ix) at least one of R2α, R3α, R4α, R5α, R6α, R2β, R3β, R4β, R5β or R6β is, or R2α and R3α, R3α and R4α, R4α and R5α, R5α and R6α, R2β and R3β, R3β and R4β, R4β and R5β or R5β and R6β join together to be, an aryl, heterocycle or heteroaromatic; and
x) at least one of R2α, R3α, R4α, R5α, or R6α, and at least one of R2β, R3β, R4β, R5β or R6β is a substituent other than hydrogen.

In another embodiment, the compound is of the formula (II):

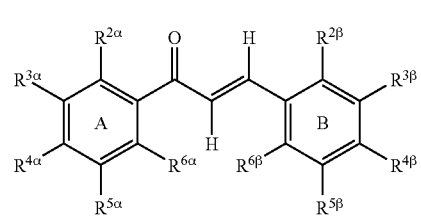

or its pharmaceutically acceptable salt.

In another embodiment, R1 is independently H or lower alkyl, R2 is an optionally substituted alkyl; and at least one of R2α, R3α, R4α, R5α, or R6α, and at least one of R2β, R3β, R4β, R5β or R6β is a substituent other than hydrogen.

In another embodiment, R4β or R5β is optionally substituted heteroaryl or heterocycle; and at least one of R2α, R3α, R4α, R5α, or R6α is a substituent other than hydrogen.

In another embodiment, R4α or R5α is optionally substituted heteroaryl or heterocycle; and at least one of R2β, R3β, R4β, R5β, or R6β is a substituent other than hydrogen.

In a particular embodiment, R5β is optionally substituted thienyl or benzothienyl; R2α, R3α, R4α, R5α, R6α, or R2β, R3β, R4β, and R6β are independently hydrogen, methoxy, ethoxy, propoxy, benzyloxy, 4-carboxybenzyloxy, 4-ethoxycarbonylbenzyloxy, 4-aminobenzyloxy, fluoro, chloro, bromo, iodo, hydroxy, OCH2CO2H, SCH2CO2H, NHCH2CO2H, CO2H, pyrid-2-ylmethoxy, pyrid-3-ylmethoxy, pyrid-4-ylmethoxy; thien-2-ylmethoxy, thien-3-ylmethoxy, fur-2-ylmethoxy, fur-3-ylmethoxy and at least one of R2α, R3α, R4α, R5α, or R6α is a substituent other than hydrogen.

In another embodiment, at least one of R2α, R3α, R4α, R5α, R6α, R2β, R3β, R4β, R5β or R6β, is or R2α and R3α, R3α and R4α, R4α and R5α, R5α and R6α, R2β and R3β, R3β and R4β, R4β and R5β or R5β and R6β join to form a carbocycle, aryl, heterocycle or heteroaromatic in which the carbocycle, aryl, heteroaryl or heterocycle is a 5, 6 or 7 membered ring, optionally conjugated to another carbocycle, aryl, heteroaryl or heterocycle.

In one embodiment, the heteroaryl group is not an oxazole.

In yet another embodiment, either R3α and R4α or R5α and R4α join to form a 5-membered methylendioxyphenyl group.

In one alternative embodiment, one of the A or B rings has only hydrogen substituents.

While it has been known that certain chalcones exhibit antiinflammatory properties, it has not been reported that the presently disclosed class of 1,3-di-(substituted-phenyl)-2-propenones inhibit the expression of VCAM-1, and are useful anti-inflammatory agents.

One of the challenges of the prior biological use of chalcones has been that the phenyl groups of the chalcone can be metabolized by ring hydroxylation (by oxidizing enzymes, including but not limited to cytochrome P450) or via break down of the chalcone double bond. As part of the invention, the present chalcones include a heteroaryl, aryl or heterocyclic group attached to one of the phenyl rings to increase the half life and thus bioavailability of the compound. However, the addition of the heteroaryl, aryl or heterocyclic group can decrease the water solubility of the compound, which has the effect of actually limiting the bioavailability of the compound. Therefore, in a preferred embodiment, the chalcone contains both a heterocycle, heteroaromatic or aryl group on at least one of the A and B phenyl rings to limit the metabolism of the compound, and at least one group that increases the water solubility of the compound. Since phenyl hydroxylation typically occurs at the para position, in a preferred embodiment, the aryl, heteroaryl or heterocyclic group is positioned at the para position, or at a meta position that blocks para-hydroxylation. Alternatively, halogen, especially fluorine, increases metabolic stability when placed in the position(s) most susceptible to hydroxylation. Bulky alkoxy groups like cyclopropyl methoxy, heteroarylalkoxy (for example, thienyl methoxy, furryl methoxy and pyridyl methoxy) and heterocyclealkoxy also increase metabolic stability when placed at the meta or para position. It has been observed that adding the group that increases water solubility to the B ring typically increases the water solubility more than when the same group is added to the A ring, however, this trend may not hold true in all cases. Preferred water solubilizing groups are alkoxy, such as methoxy, OC(R1)2CO2H, SC(R1)2CO2H, NHC(R1)2CO2H or OC(R1)2CO2H, wherein R1 is H or lower alkyl. In a more general embodiment, any group that increases the water solubility of the compound can be used as substituents for R2α, R3α, R4α, R5α, R6α, R2β, R3β, R4β, R5β and R6β, specifically including but not limited to alkoxy, alkylthio, alkylamino, aminoalkyl, haloalkylthio, acyl, amido, acylamino, amino, dialkylamino, aminodialkyl, trifluoroalkoxy, alkylsulfonyl, haloalkylsulfonyl, aminocarbonyl, hydroxyl, thiol, cyano, nitro, sulfonic acid, sulfonate, sulfate, sulfinic acid, sulfenic acid, sulfamide, sulfonamide, sulfoxide, metal sulfinate, phosphate, phosphonate, metal phosphonate, phosphinate, alditol, carbohydrate, amino acid, CO—R2, CO2—R2, polyoxyalkylene, polyol alkyl, NH2.HCl, oxyalkylamino, alkylcarbonylalkyl, lower alkyl S(O)-lower alkyl, lower alkyl-S(0)2-lower alkyl; imidazolyl lower alkyl, morpholinyl lower alkyl, thiazolinyl lower alkyl, piperidinyl lower alkyl, imidazolylcarbonyl, morpholinyl carbonyl, (lower alkyl)-aminocarbonyl, N-pyrrylpyridinyl-lower alkyl; pyridylthio-lower alkyl; morpholinyl-lower alkyl; hydroxyphenylthio-lower alkyl; cyanophenylthio-lower alkyl; imidazolylthio-lower alkyl; triazolylthio-lower alkyl; triazolylphenylthio-lower alkyl; tetrazolylthio-lower alkyl; tetrazolylphenylthio-lower alkyl; aminophenylthio-lower alkyl; N,N-di-substituted aminophenylthio-lower alkyl wherein the amine substituents each independently represent lower alkyl; amidinophenylthio-lower alkyl; phenylsulfinyl-lower alkyl; phenylsulfonyl lower alkyl; -lower alkyl-O—R, wherein R is PO2(OH)—M+ or PO3(OH)—M+ wherein M+ is a pharmaceutically acceptable cation; —C(O)(CH2)2CO2—M+; —SO3M+; -lower alkylcarbonyl-lower alkyl; -carboxy lower alkyl; -lower alkylamino-lower alkyl; N,N-di-substituted amino lower alkyl-, wherein the substituents each independently represent lower alkyl; pyridyl-lower alkyl; imidazolyl-lower alkyl; imidazolyl-Y-lower alkyl wherein Y is thio or amino; morpholinyl-lower alkyl; pyrrolidinyl-lower alkyl; thiazolinyl-lower alkyl; piperidinyl-lower alkyl; morpholinyl-lower hydroxyalkyl; N-pyrryl; piperazinyl-lower alkyl; N-substituted piperazinyl-lower alkyl, wherein the amine substituent is lower alkyl; triazolyl-lower alkyl; tetrazolyl-lower alkyl; tetrazolylamino-lower alkyl; or thiazolyl-lower alkyl; hydroxyalkyl, aralkoxy, heteroaryl lower alkoxy, heterocyclo lower alkoxy, heteroaryloxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, any of which can be optionally substituted with a moiety that does not adversely affect the biological properties of the molecule;

In a preferred embodiment, after the target biological activity, metabolic stability and water solubility have been jointly optimized, substituent groups that do not contribute to these factors or contribute another attribute are removed.

BRIEF DESCRIPTION OF THE FIGURES

FIG. 2 is a bar chart graph of the inhibition of eosinophil recruitment (percent eosinophils in the peritoneal fluid) by 50 mg/kg/dose of 3-[5-(benzo[b]thien-2-yl)-2,4-dimethoxyphenyl]-1-(3,4,5-trimethoxyphenyl)-2-propen-1-one. Balb/C mice (n=10) were sensitized to ovalbumin on days 0 and 7 with a subcutaneous injection of ovalbumin absorbed in aluminum hydroxide. They were then challenged with an intraperitoneal injection of ovalbumin and sacrificed 48 hrs post-challenge. Peritoneal fluid was then collected and spun down onto slides. Slides were stained with DiffQuik and a differential performed. The test compound was administered by subcutaneously injection –24, –2, +2 and +6 hrs around the time of ovalbumin challenge. This is a model of allergic inflammation as eosinophils are the major leukocyte recruited into the peritoneum.

FIG. 3 is a bar chart graph of the inhibition of paw edema in a mouse model of delayed type hypersensitivity by 50 mg/kg/dose of 3-[5-(benzo[b]thien-2-yl)-2,4-dimethoxyphenyl]-1-(3,4,5-trimethoxyphenyl)-2-propen-1-one. Balb/C mice (n=5) were sensitized intradermally on day 0 with methylated BSA (metBSA). They were then challenged with metBSA on day 7 in the right hind paw. The animals were sacrificed 24 hours later and the left and right hind paws weighed. The left hindpaw weight is subtracted from the right hind paw to give the paw weight increase. The test compound was administered by intraperitoneal injection –24, –2 and +6 hrs around the time of metBSA challenge.

DETAILED DESCRIPTION OF THE INVENTION

Figure 1:
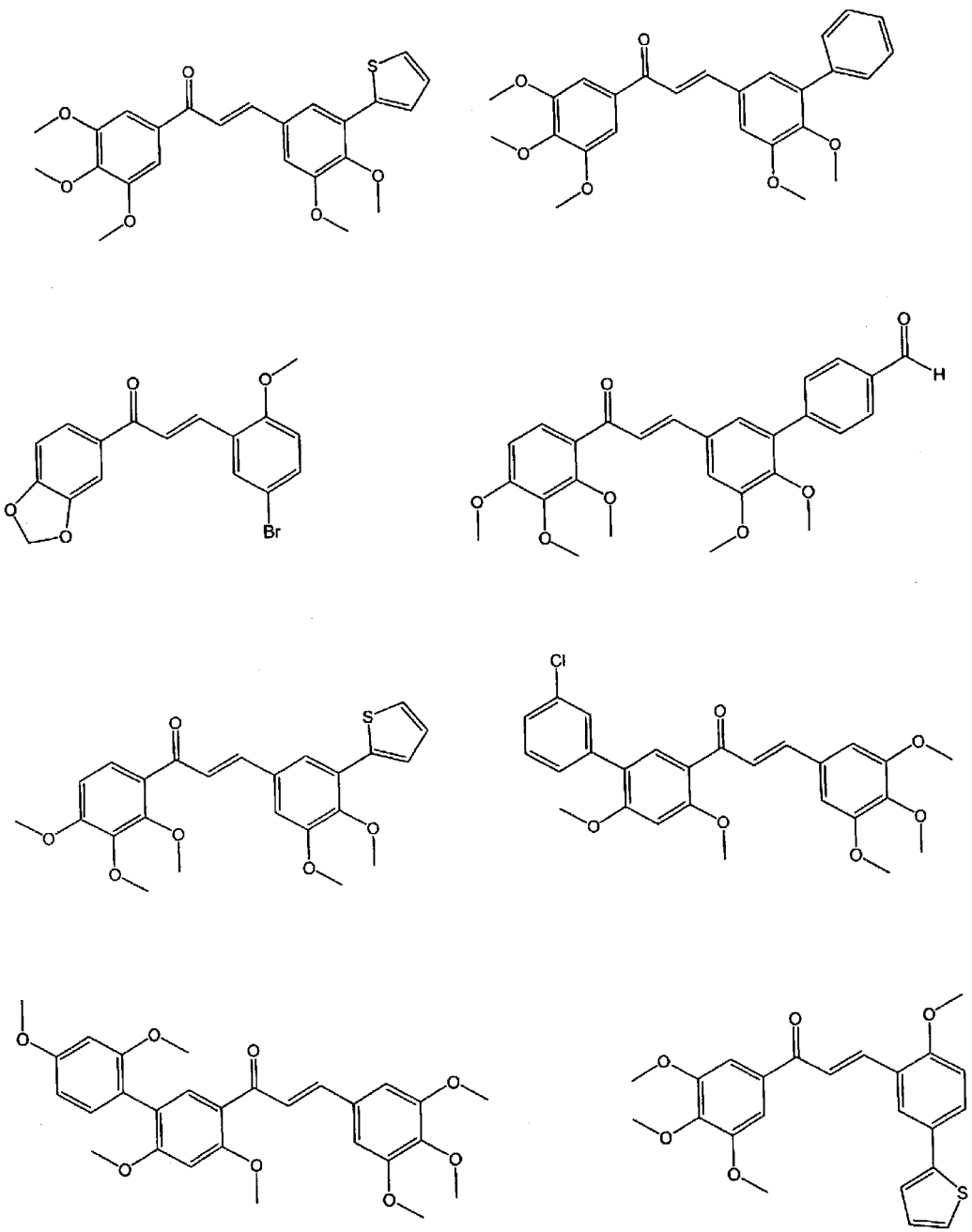
FIG. 1 is an illustration of non-limiting examples of compounds of the present invention.
Figure 1:
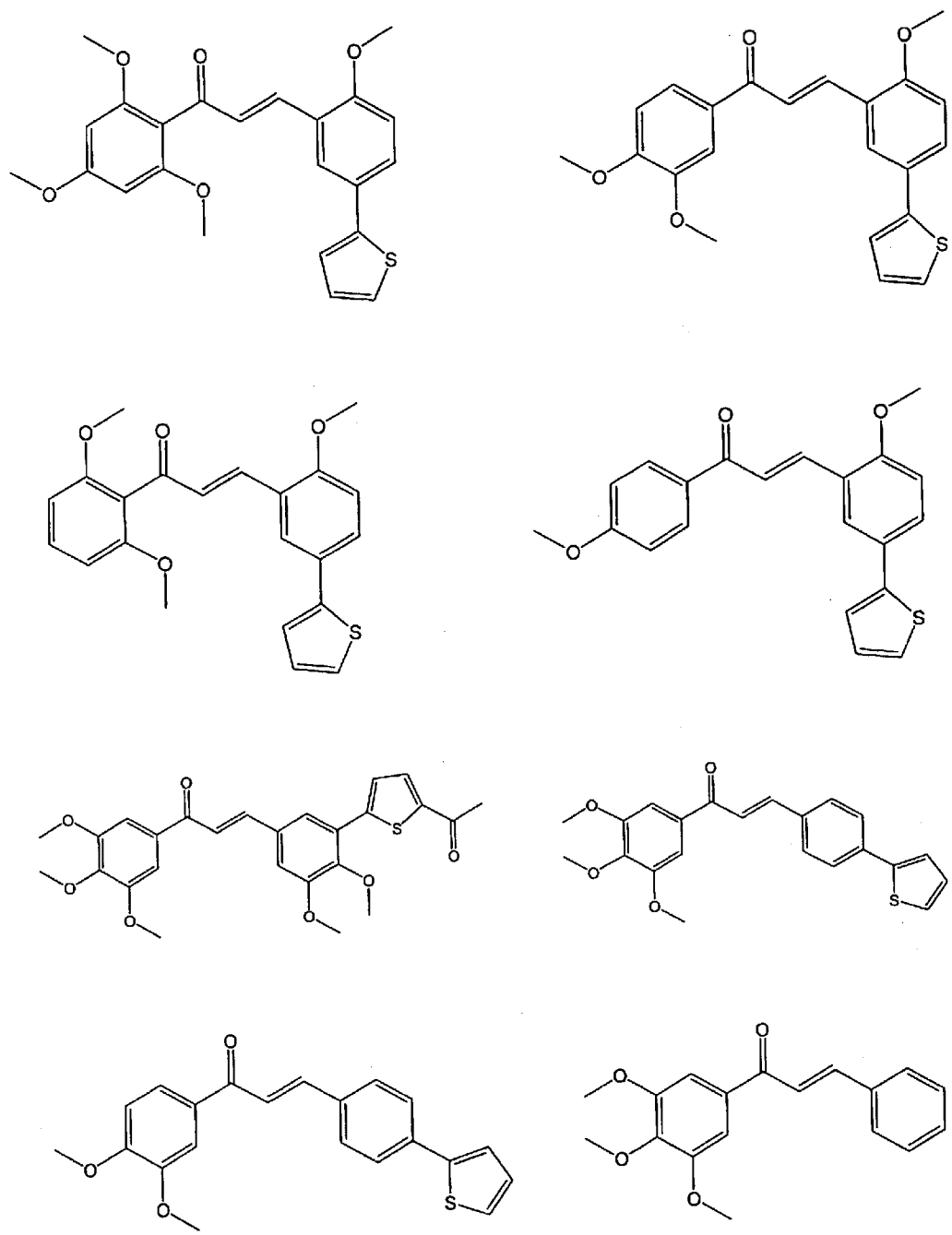
Figure 1:
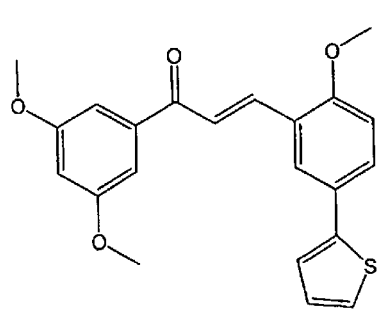
Figure 1:
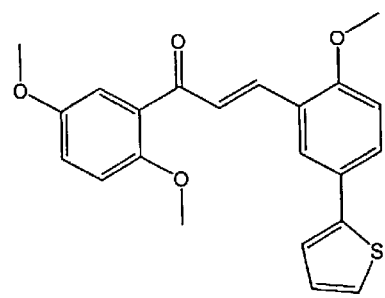
Figure 1:
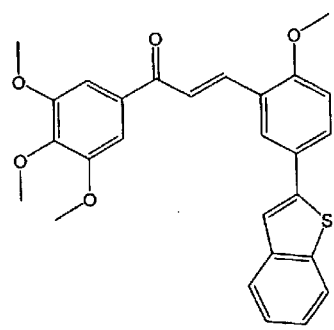
Figure 1:
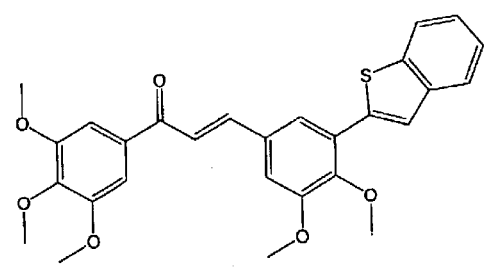
Figure 1:
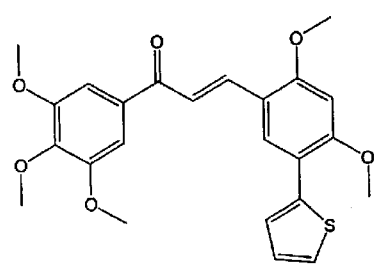
Figure 1:
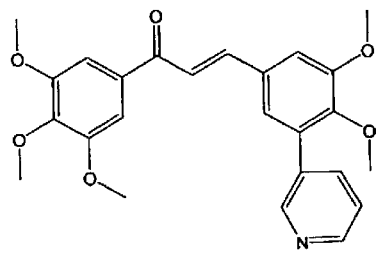
Figure 1:
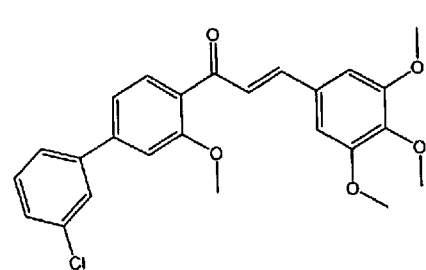
Figure 1:
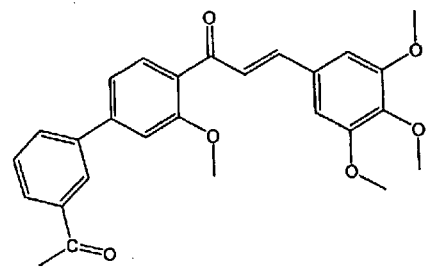
Figure 1:
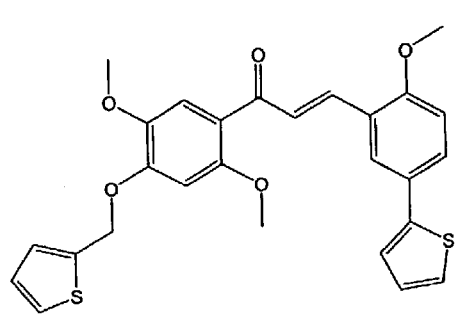
Figure 1:
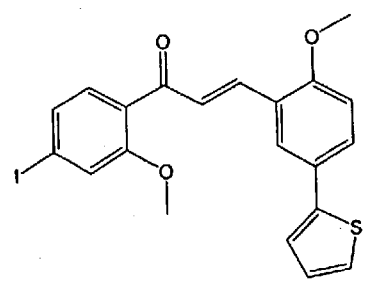
Figure 1:
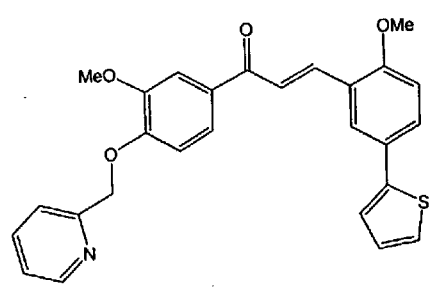
Figure 1:
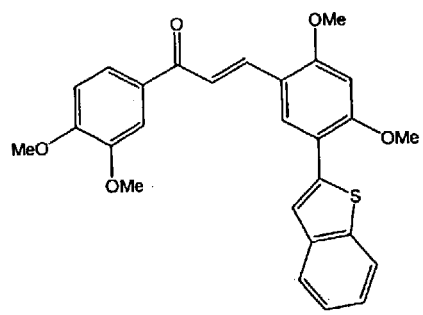
Figure 1:
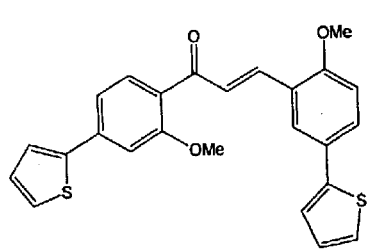
Figure 1:
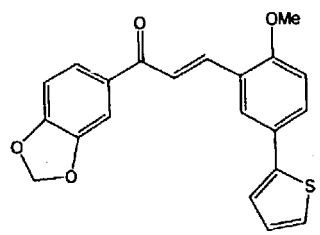
Figure 1:
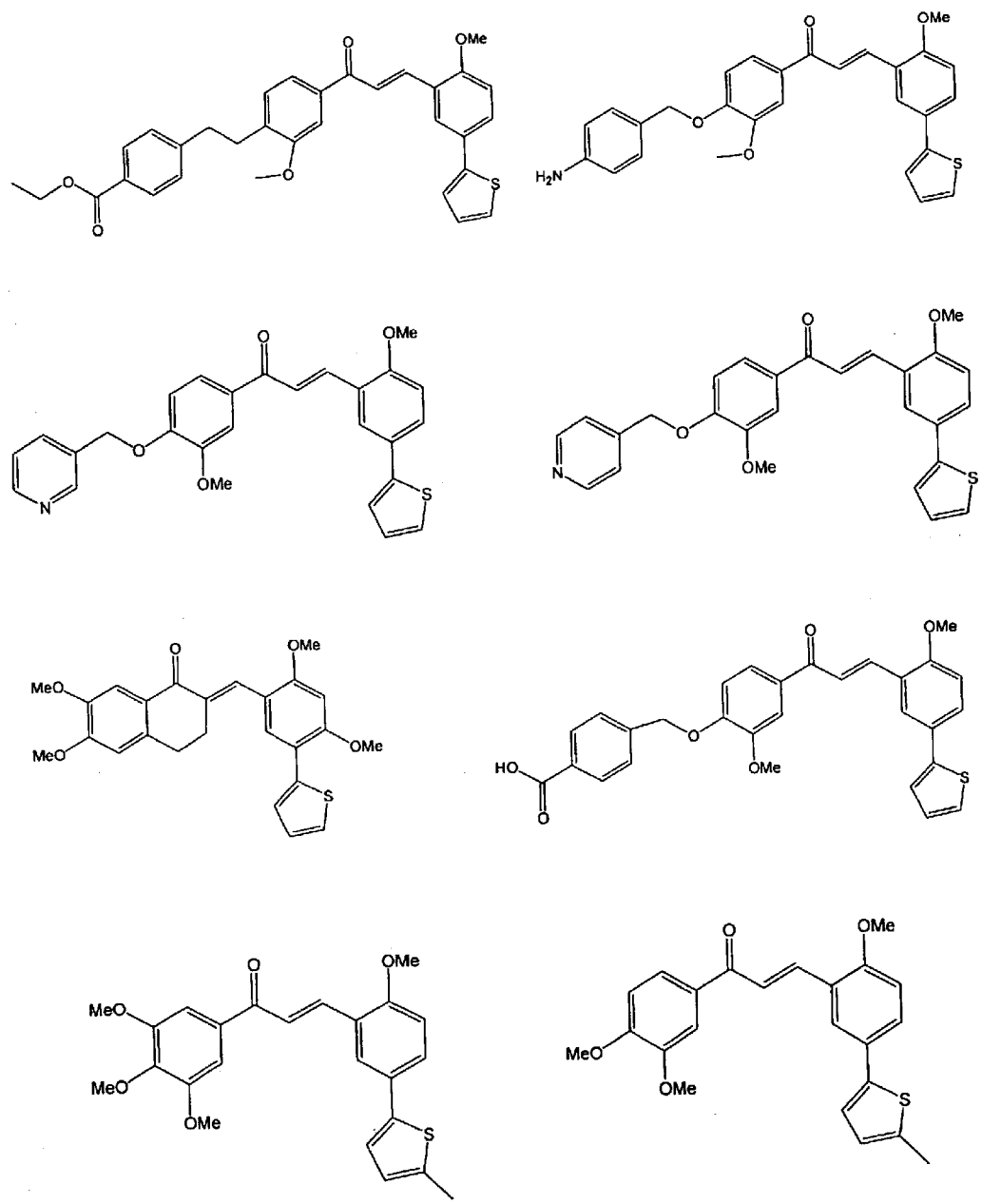
Figure 1:
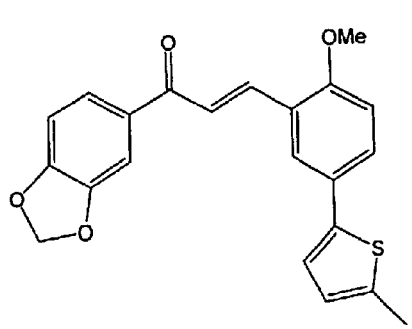
Figure 1:
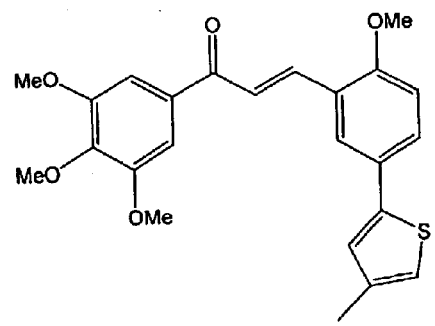
Figure 1:
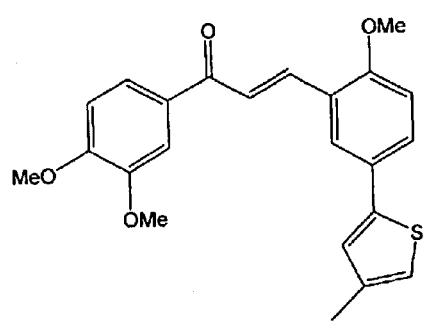
Figure 1:
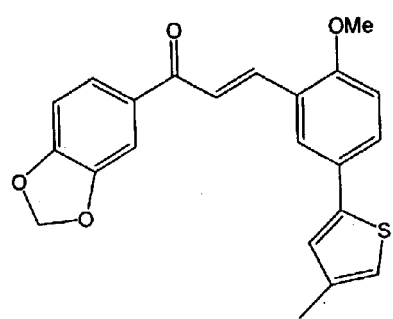
Figure 1:
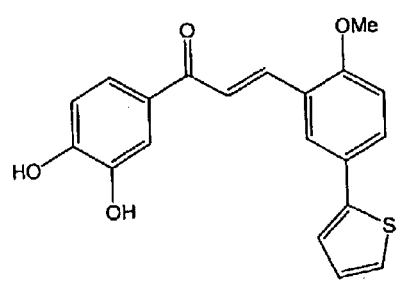
Figure 1:
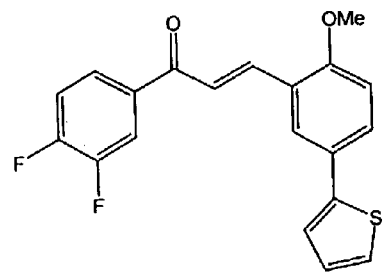
Figure 1:
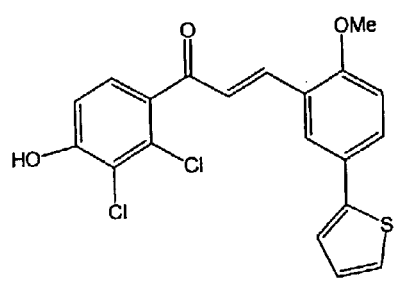
Figure 1:
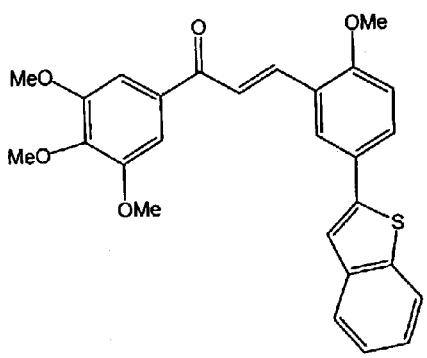
Figure 1:
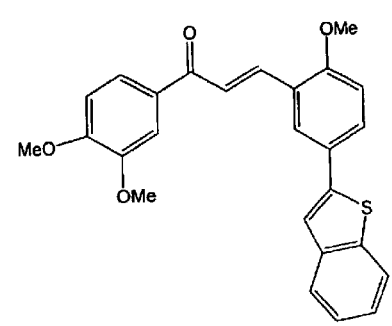
Figure 1:
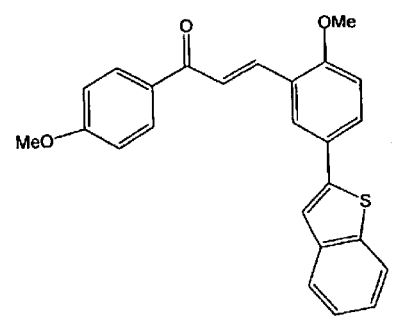
Figure 1:
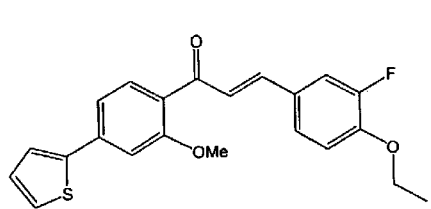
Figure 1:
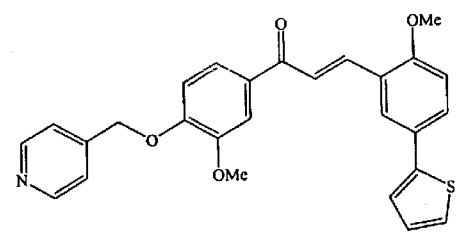
Figure 1:
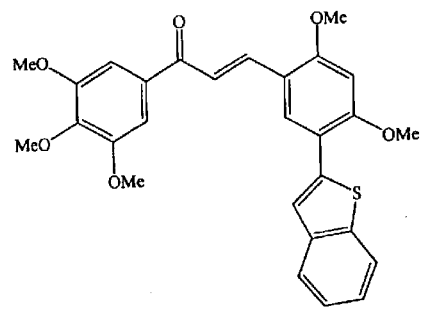

It has been discovered that compounds of formula (I) inhibit the expression of VCAM-1, and thus can be used to treat a patient with a disorder mediated by VCAM-1. These compounds can be administered to a host as monotherapy, or if desired, in combination with another compound of formula (I) or another bioloigically active agent, as described in more detail below.

The compounds can be used to treat inflammatory disorders that are mediated by VCAM-1 including, but not limited to arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

The compounds disclosed herein can be used in the treatment of inflammatory skin diseases that are mediated by VCAM-1, and in particular, human endothelial disorders that are mediated by VCAM-1, which include, but are not limited to, psoriasis, dermatitis, including eczematous dermatitis, and Kaposi's sarcoma, as well as proliferative disorders of smooth muscle cells.

In yet another embodiment, the compounds disclosed herein can be selected to treat anti-inflammatory conditions that are mediated by mononuclear leucocytes.

In yet another embodiment, the compounds of the present invention can be selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. They are also indicated for the prevention or treatment of graft-versus-host disease, which sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

In another aspect the invention provides pharmaceutical compositions for the treatment of diseases or disorders mediated by VCAM-1 wherein such compositions comprise a VCAM-1 inhibiting amount of a chalcone derivatives of the formula (I) or a pharmaceutically acceptable salt thereof and a pharmaceutically acceptable carrier.

In another aspect the invention provides a method for treating a disease or disorder mediated by VCAM-1 comprising administering to a patient a VCAM-1 inhibiting effective amount of a compound of formula (I) or a pharmaceutically acceptable salt thereof.

In another aspect the invention provides a method for treating cardiovascular and inflammatory disorders in a patient in need thereof comprising administering to said patient an VCAM-1 inhibiting effective amount of a compound of formula (I) or a pharmaceutically acceptable salt thereof.

In another aspect the invention provides a method and composition for treating asthma or arthritis in a patient in need thereof comprising administering to said patient an effective amount of a compound of formula (I) or a pharmaceutically acceptable salt thereof.

I. Compounds of the Present Invention

In one embodiment, the invention provides compounds of formula (I) and their pharmaceutically acceptable salts or prodrugs:

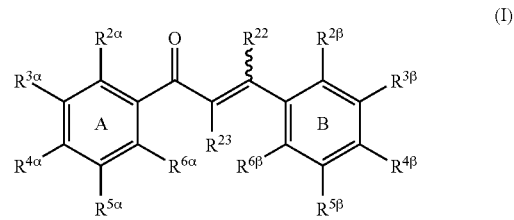

(I)

or its pharmaceutically acceptable salt, wherein:

xi) the wavy line indicates that the compound can be in the form of the E or Z isomer;

xii) R22 and R23 are independently hydrogen or (C1–C4) alkyl, xiii) R2α, R3α, R4α, R5α, R6α, R2β, R3β, R4β, R5β and R6β are independently xiv) hydrogen, alkyl, carbocycle, aryl, heteroaryl, heterocycle, aryloxy; arylalkoxy; heteroaryloxy; heteroarylalkoxy, cycloalkyl, alkoxy, alkylthio, alkylamino, aminoalkyl, haloalkylthio, acyl, haloalkyl, aryloxy, amido, acylamino, amino, dialkylamino, aminodialkyl, trifluoroalkoxy, alkylsulfonyl, haloalkylsulfonyl, aminocarbonyl, alkenyl, alkynyl, halogen, hydroxyl, thiol, cyano, nitro, sulfonic acid, sulfonate, sulfate, sulfinic acid, sulfenic acid, sulfamide, sulfonamide, sulfoxide, metal sulfinate, phosphate, phosphonate, metal phosphonate, phosphinate, alditol, carbohydrate, amino acid, OC(R1)2CO2H, SC(R1)2CO2H, NHCHR1CO2H, CO—R2, CO2R1, polyoxyalkylene, polyol alkyl, oxyalkylamino, alkylcarbonylalkyl, lower alkyl S(O)-lower alkyl, lower alkyl-S(O)2-lower alkyl; hydroxyalkyl, aralkoxy, heteroaryl lower alkoxy, heterocyclo lower alkoxy, heteroaryloxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, any of which can be optionally substituted with a moiety that does not adversely affect the biological properties of the molecule; —C(O)(CH2)2CO2—M+, —SO3M+, or -lower alkyl-O—R, wherein R is PO2(OH)—M+, PO3(OH)—M+ or —SO3M+, wherein M+ is a pharmaceutically acceptable cation; -lower alkylcarbonyl-lower alkyl; carboxy lower alkyl; -lower alkylamino-lower alkyl; N,N-di-substituted amino lower alkyl-, wherein the substituents each independently represent lower alkyl;

xv) R1 is H, lower alkyl, an optionally substituted carbocycle, aryl, heteroaryl, heterocycle, alkylaryl, alkylheteroaryl, alkylheteroaryl or alkylheterocycle;

xvi) R2 is an optionally substituted alkyl, alkenyl, alkynyl, aryl, carbocycle, heteroaryl, heterocycle, alkylaryl, alkylheteroaryl, alkylheteroaryl or alkylheterocycle;

xvii) alternatively, R22 and R6α or R23 and R6α can join together to form a bridged carbocycle, aryl, heterocycle or heteroaromatic;

xviii) R2α and R3α, R3α and R4α, R4α and R5α, R5α and R6α, R2β and R3β, R3β and R4β, R4β and R5β or R5β and R6β can independently join to form a bridged compound selected from the group consisting of an optionally substituted carbocycle, an optionally substituted cycloalkenyl, an optionally substituted cycloalkylcarbonyl, an optionally substituted cycloalkenylcarbonyl; an optionally substituted aryl, an optionally substituted heterocylic or an optionally substituted heteroaromatic, or alkylenedioxy or wherein the ring can include a carbonyl, cyclic ester, amide, amine, sulfonate, or phosphonate;

xix) at least one of R2α, R3α, R4α, R5α, R6α, R2β, R3β, R4β, R5β or R6β is, or R2α and R3α, R3α and R4α, R4α and R5α, R5α and R6α, R2β and R3β, R3β and R4β, R4β and R5β or R5β and R6β come together to be, an aryl, heterocycle or heteroaromatic; and xx) at least one of R2α, R3, R4α, R5α, or R6α, and at least one of R2β, R3β, R4β, R5β or R6β is a substituent other than hydrogen.

In another embodiment, the compound is of the formula (II):

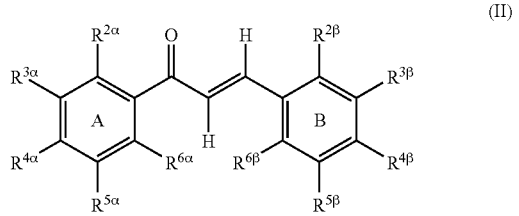

or its pharmaceutically acceptable salt.

In another embodiment, R1 is independently H or lower alkyl, R2 is an optionally substituted alkyl; and at least one of R2α, R3α, R4α, R5α, or R6α, and at least one of R2β, R3β, R4β, R5β or R6β is a substituent other than hydrogen.

In another embodiment, R4β or R5β is optionally substituted heteroaryl or heterocycle; and at least one of R2α, R3α, R4α, R5α or R6α is a substituent other than hydrogen.

In another embodiment, R4α or R5α is optionally substituted heteroaryl or heterocycle; and at least one of R2β, R3β, R4β, R5β, or R6β is a substituent other than hydrogen.

In one alternative embodiment, one of the A or B rings has only hydrogen substituents.

In a particular embodiment, R5β is optionally substituted thienyl or benzothienyl; R2α, R3α, R4α, R5α, R6α, or R2β, R3β, R4β, and R6β are independently hydrogen, methoxy, ethoxy, propoxy, benzyloxy, 4-carboxybenzyloxy, 4-ethoxycarbonylbenzyloxy, 4-aminobenzyloxy, fluoro, chloro, bromo, iodo, hydroxy, OCH2CO2H, SCH2CO2H, NHCH2CO2H, CO2H, pyrid-2-ylmethoxy, pyrid-3-ylmethoxy, pyrid-4-ylmethoxy; thien-2-ylmethoxy, thien-3-ylmethoxy, fur-2-ylmethoxy, fur-3-ylmethoxy and at least one of R2α, R3α, R4α, R5α, or R6α is a substituent other than hydrogen.

In another embodiment, at least one of R2α, R3α, R4α, R5α, R6α, R2β, R3β, R4β, R5β or R6β, is or R2α and R3α, R3α and R4α, R4α and R5α, R5α and R6α, R2β and R3β, R3β and R4β, R4β and R5β or R5β and R6β join to form a carbocycle, aryl, heterocycle or heteroaromatic in which the carbocycle, aryl, heteroaryl or heterocycle is a 5, 6 or 7 membered ring, optionally conjugated to another carbocycle, aryl, heteroaryl or heterocycle. In yet another embodiment, either R3α and R4α or R5α and R4α join to form a 5-membered methylendioxyphenyl group.

In a primary embodiment, the compounds of the formula (I) are of the more specific formula (II):

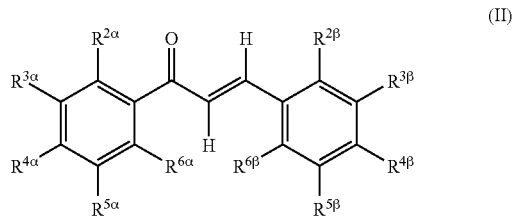

or its pharmaceutically acceptable salt or prodrug thereof, wherein:

R2α, R3α, R4α, R5α, R6α, R2β, R3β, R4β, R5β and R6β are defined above.

In a particular embodiment, the optionally substituted carbocycle, aryl, heteroaryl or heterocycle is a 5, 6 or 7 membered ring, optionally substituted or conjugated to another optionally substituted carbocycle, aryl, heteroaryl or heterocycle.

In another sub-embodiment, the invention provides trans compounds of formula (II) and their pharmaceutically acceptable salts or prodrugs thereof wherein;

R2α, R3α, R4α, R5α and R6α are independently selected from alkyl, alkoxy, hydroxy, halogen, preferably chloro, heterocycle, heteroaromatic, OC(R1)2CO2H wherein R1 is H, or lower alkyl, O-alkylheteroaryl and R2β, R3β, R4β, R5β and R6β are independently selected from alkyl, alkoxy, hydroxy, halogen, preferably F or Br, carbocycle, aryl, heterocycle and heteroaryl, preferably thienyl or benzothienyl.

In one embodiment the invention provides trans compounds of formula (II) and a pharmaceutically acceptable salts or prodrugs that exhibit a sufficient solubility in water and an in vitro inhibition of fifty percent of VCAM expression at 10 micromolar concentration.

In another embodiment, at least one of R2α, R3α, R4α, R5α, R6α, R2β, R3β, R4β, R5β and R6β is selected from halogen, alkoxy, hydroxy, OC(R1)2CO2H, SC(R1)2CO2H, or NHC(R1)2CO2H; or its pharmaceutically acceptable salt; R1 is H, or lower alkyl; the remaining Rα/β groups are selected independently from H; halogen, thio, cyano, nitro, optionally substituted alkyl; cycloalkyl; hydroxy; alkoxy; alkylthio; alkylamino, aminoalkyl, haloalkylthio; haloalkyl; carboxyl derivatives; aryloxy; arylalkoxy; heteroaryloxy; heteroarylalkoxy, amido; acylamino; amino, dialkylamino; trifluoroalkoxy; alkylsulfonyl, haloalkylsulfonyl; sulfonic acid; sulfonate, sulfate, sulfinic acid, sulfenic acid, sulfamide, sulfonamide; sulfoxide, metal sulfinate, phosphate, phosphonate, metal phosphonate, phosphinate aminocarbonyl; alkenyl; alkynyl; alditol, carbohydrate, carbocycle, aryl, heteroaryl, and heterocycle; or the remaining Rα/β groups can join to form a 5, 6 or 7 membered optionally substituted carbocycle, aryl, heteroaryl or heterocycle, optionally conjugated to another optionally substituted carbocycle, aryl, heteroaryl.

In a preferred embodiment the invention provides trans compounds of formula (II) and a pharmaceutically acceptable salts or prodrugs that increase the solubility of the molecule while maintaining or increasing the inhibition of VCAM expression wherein:

at least one of the R2β, R3β, R4β, R5β and R6β is selected from OC(R1)2CO2H, SC(R1)2CO2H, NHC(R1)2CO2H or their salts;

R2α, R3α, R4α, R5α and R6α are selected independently from H; halogen, thio, cyano, nitro, optionally substituted alkyl; cycloalkyl; hydroxy; alkoxy; alkylthio; alkylamino, aminoalkyl, haloalkylthio; haloalkyl; carboxyl derivatives; aryloxy; arylalkoxy; heteroaryloxy; heteroarylalkoxy, amido; acylamino; amino, dialkylamino; trifluoroalkoxy; alkylsulfonyl, haloalkylsulfonyl; sulfonic acid; sulfonate, sulfate, sulfinic acid, sulfenic acid, sulfamide, sulfonamide; sulfoxide, metal sulfinate, phosphate, phosphonate, metal phosphonate, phosphinate aminocarbonyl; alkenyl; alkynyl; alditol, carbohydrate, carbocycle, aryl, heteroaryl and heterocycle; or the remaining Rα/β groups can join to form a 5, 6 or 7 membered optionally substituted carbocycle, aryl, heteroaryl or heterocycle, optionally conjugated to another optionally substituted carbocycle, aryl, heteroaryl.

In yet another preferred embodiment the invention provides trans compounds of formula (II) and a pharmaceutically acceptable salts or prodrugs that increase the solubility of the molecule while maintaining or increasing the inhibition of VCAM expression wherein:

R2β is selected from OC(R1)2CO2H, SC(R1)2CO2H, or NHC(R1)2CO2H; or its pharmaceutically acceptable salt;

R1 is H, or lower alkyl;

R3β, R4β, R5β, R6β, R2α, R3α, R4α, R5α and R6α are selected independently from H; halogen, thio, cyano, nitro, optionally substituted alkyl; cycloalkyl; hydroxy; alkoxy; alkylthio; alkylamino, aminoalkyl, haloalkylthio; thio; cyano; halo; haloalkyl; nitro; carboxyl derivatives; aryloxy; arylalkoxy; heteroaryloxy; heteroarylalkoxy, amido; acylamino; amino, dialkylamino; trifluoroalkoxy; alkylsulfonyl, haloalkylsulfonyl; sulfonic acid; sulfonate, sulfate, sulfinic acid, sulfenic acid, sulfamide, sulfonamide; sulfoxide, metal sulfinate, phosphate, phosphonate, metal phosphonate, phosphinate aminocarbonyl; alkenyl; alkynyl; alditol, carbohydrate, carbocycle, aryl, heteroaryl, and heterocycle; or R2α and R3α, R3α and R4α, R4α and R5α, R5α and R6α, R3β and R4β, R4β and R5β or R5β and R6β can join to form a 5, 6 or 7 membered optionally substituted carbocycle, aryl, heteroaryl or heterocycle, optionally conjugated to another optionally substituted carbocycle, aryl, heterocycle or heteroaryl.

In yet another embodiment the invention provides compounds of the formula (II) and a pharmaceutically acceptable salts or prodrugs that are metabolically stable: wherein:

R4α and R4β are independently selected from cyano; halo; nitro; substituted or unsubstituted alkyl; cycloalkyl; alkoxy; alkylthio; alkylamino; aminoalkyl; haloalkylthio; haloalkyl; carboxyl derivatives; aryloxy; arylalkoxy; heteroaryloxy; heteroarylalkoxy, amido; acylamino; amino, dialkylamino; trifluoroalkoxy; aminocarbonyl; alkenyl; alkynyl; alditol; carbohydrate; aryl; heteroaryl; and heterocycle; or R2α and R4α; R4α and R5α; R3β and R4β; or R4β and R5β; independently form a 5–7 membered optionally substituted carbocyclic, aryl; heteroaryl or heterocyclic ring;

the remaining Rα/β groups are selected independently from H; halogen, thio, cyano, nitro, optionally substituted alkyl; cycloalkyl; hydroxy; alkoxy; alkylthio; alkylamino, aminoalkyl, haloalkylthio; haloalkyl; carboxyl derivatives; aryloxy; arylalkoxy; heteroaryloxy; heteroarylalkoxy, amido; acylamino; amino, dialkylamino; trifluoroalkoxy; alkylsulfonyl, haloalkylsulfonyl; sulfonic acid; sulfonate, sulfate, sulfinic acid, sulfenic acid, sulfamide, sulfonamide; sulfoxide, metal sulfinate, phosphate, phosphonate, metal phosphonate, phosphinate aminocarbonyl; alkenyl; alkynyl; alditol, carbohydrate, carbocycle, aryl, heteroaryl and heterocycle; or the remaining Rα/β groups can join to form a 5, 6 or 7 membered optionally substituted carbocycle, aryl, heteroaryl or heterocycle, optionally conjugated to another optionally substituted carbocycle, aryl, heteroaryl, and R1 is H; or lower alkyl; or In a preferred embodiment the invention provides trans compounds of formula (II) and a pharmaceutically acceptable salts or prodrugs that are metabolically stable: wherein:

R4α and R4β independently from each other are selected from halogen preferably F or heteroaryl preferably thienyl and benzothienyl and, and R3β, R5β, R6β, R2α, R3α, R5α and R6α are selected from H, cyano; nitro; halo preferably F; optionally substituted alkyl; cycloalkyl; alkoxy; alkylthio; alkylamino; aminoalkyl; haloalkylthio; haloalkyl; carboxyl derivatives; aryloxy; amido; acylamino; amino, dialkylamino; trifluoroalkoxy; aminocarbonyl; alkenyl; alkynyl; alditol; carbohydrate; aryl; heteroaryl; and heterocycle; or R3α and R4α, R4α and R5β, R3β and R4β, or R4β and R5β independently can join to form a 5–7 membered optionally substituted carbocylic; aryl; heteroaryl; or heterocyclic ring; and the remaining Rα/β groups are selected independently from H; halogen, thio, cyano, nitro, optionally substituted alkyl; cycloalkyl; hydroxy; alkoxy; alkylthio; alkylamino, aminoalkyl, haloalkylthio; haloalkyl; carboxyl derivatives; aryloxy; arylalkoxy; heteroaryloxy; heteroarylalkoxy, amido; acylamino; amino, dialkylamino; trifluoroalkoxy; alkylsulfonyl, haloalkylsulfonyl; sulfonic acid; sulfonate, sulfate, sulfinic acid, sulfenic acid, sulfamide, sulfonamide; sulfoxide, metal sulfinate, phosphate, phosphonate, metal phosphonate, phosphinate aminocarbonyl; alkenyl; alkynyl; alditol, carbohydrate, carbocycle, aryl, heteroaryl and heterocycle; or the remaining Rα/β groups can join to form a 5, 6 or 7 membered optionally substituted carbocycle, aryl, heteroaryl or heterocycle, optionally conjugated to another optionally substituted carbocycle, aryl, heteroaryl, and R1 is H; or lower alkyl.

In another embodiment the invention provides trans compounds of formula (II) and a pharmaceutically acceptable salts or prodrugs: wherein:

at least one of the following pairs R3α and R4α, R4α and R5α, R3β and R4β, or R4β and R5β comes together to form a 5, 6 or 7 membered optionally substituted heteroaryl or optionally substituted heterocycle, optionally conjugated to another optionally substituted carbocycle, optionally substituted aryl, or heteroaryl, wherein the heteroatom of the ring is selected from O, S or N; and the remaining Rα/β groups are independently selected from H; halogen, thio, cyano, nitro, optionally substituted alkyl; cycloalkyl; hydroxy; alkoxy; alkylthio; alkylamino, aminoalkyl, haloalkylthio; haloalkyl; carboxyl derivatives; aryloxy; arylalkoxy; heteroaryloxy; heteroarylalkoxy, amido; acylamino; amino, dialkylamino; trifluoroalkoxy; alkylsulfonyl, haloalkylsulfonyl; sulfonic acid; sulfonate, sulfate, sulfinic acid, sulfenic acid, sulfamide, sulfonamide; sulfoxide, metal sulfinate, phosphate, phosphonate, metal phosphonate, phosphinate aminocarbonyl; alkenyl; alkynyl; alditol, carbohydrate, carbocycle, aryl, heteroaryl and heterocycle; or the remaining Rα/β groups can join to form a 5, 6 or 7 membered optionally substituted carbocycle, aryl, heteroaryl or heterocycle, optionally conjugated to another optionally substituted carbocycle, aryl, heteroaryl.

In another embodiment, the invention provides trans compounds of formula (II) and their pharmaceutically acceptable salts or prodrugs thereof:
wherein;
R2α, R3α, R4α, R5α and R6α are independently selected from alkyl, alkoxy, halogen, preferably Cl, Br or I, heteroaryl, O-alkylheterocycle, O-akylheteroaryl, carboxyalkyl;
R2β, R3β, R4β, R5β and R6β are independently selected from alkyl, alkoxy, halogen, preferably F or Br, or heteroaryl, preferably benzothienyl.

In one preferred embodiment, the invention provides trans compounds of formula (II) and their pharmaceutically acceptable salts or prodrugs thereof:
wherein:
R3β and R6β are independently H;
R2α, R3α, R4α, R5α and R6α are independently selected from H, OH, OR (R is lower alkyl), halogen, OC(R1)2CO2H, SC(R1)2CO2H, or NHC(R1)2CO2H; or its pharmaceutically acceptable salt;
R2β, R4β and R5β are independently selected from O-alkyl, OC(R1)2CO2H, SC(R1)2CO2H, or NHC(R1)2CO2H; or its pharmaceutically acceptable salt; and
R1 is H, or lower alkyl.

In another preferred embodiment, the invention provides trans compounds of formula (II) and their pharmaceutically acceptable salts or prodrugs thereof:
wherein:
R2α, R6β, R3β and R6β are H;
R3α , R5β, R3β and R6β are OMe;
R4α is OC(R1)2CO2H, CO2H, SC(R1)2CO2H or NHC(R1)2CO2H; or its pharmaceutically acceptable salt;
R1 is H or lower alkyl; and
R5β is a heteroaryl or heterocycle.

In another preferred embodiment, the invention provides trans compounds of formula (II) and their pharmaceutically acceptable salts or prodrugs thereof:
wherein;
R2α, R6α, R3β and R6β are H;
R3α, R4α, R5α and R4β are OMe;
R2β is selected from OC(R1)2CO2H, CO2H, SC(R1)2CO2H or NHC(R1)2CO2H; or its pharmaceutically acceptable salt;
R1 is H or lower alkyl; and
R5β is a heteroaryl or heterocycle.

In another preferred embodiment, the invention provides trans compounds of formula (II) and their pharmaceutically acceptable salts or prodrugs thereof:
wherein;
R2α, R6α, R3β and R6β are H;
R3α, R4α, R5α, R2β and R4β are OMe; and R5β is a heteroaryl or heterocycle.

In another preferred embodiment, the invention provides trans compounds of formula (II) and their pharmaceutically acceptable salts or prodrugs thereof:
wherein;
R2α, R6α, R2β and R6β are H;
R3α, R4α, R5β, R3β and R4β are OMe; and
R5β is a heteroaryl or heterocycle.

In another preferred embodiment, the invention provides trans compounds of formula (II) and their pharmaceutically acceptable salts or prodrugs thereof:
wherein;
R3β and R6β are H;
R2β and R4β are OMe and,
R2α, R3α, R4α , R5α and R6α are independently selected from H, OH, SH, halo, alkyl, CF3, O-alkyl, CO2H, NH2, aminoalkyl, aminodialkyl, SO3H, sulfonamine, sulfonaminodi- and mono-alkyl, α-aminoacid, heterocycle, OC(R1)2CO2H, CO2H, SC(R1)2CO2H or NHC(R1)2CO2H; or its pharmaceutically acceptable salt;
R1 is H or lower alkyl; and
R5β is a heteroaryl.

In another preferred embodiment, the invention provides trans compounds of formula (II) and their pharmaceutically acceptable salts or prodrugs thereof:
wherein;
R3β, R5β and R6β are H;
R4β is OMe and,
R2β is OC(R1)2CO2H, CO2H, SC(R1)2CO2H or NHC(R1)2CO2H; or its pharmaceutically acceptable salt;
R2α, R3α, R4α, R5α and R6α are independently selected from H, OH, SH, halo, alkyl, CF3, O-alkyl, CO2H, NH2, aminoalkyl, aminodialkyl, SO3H, sulfonamine, sulfonaminodi- and mono-alkyl, α-aminoacid, heterocycle, heteroaryl, OC(R1)2CO2H, SC(R1)2CO2H, or NHC(R1)2CO2H; or its pharmaceutically acceptable salt; and
R1 is H, or lower alkyl.

In yet another preferred embodiment, the invention provides trans compounds of formula (II) and their pharmaceutically acceptable salts or prodrugs thereof:
wherein;
R2α and R6α are H and,
R4β, R3α, R4α and R5α are OMe and, R2β is OC(R1)2CO2H, SC(R1)2CO2H, or NHC(R1)2CO2H; or its pharmaceutically acceptable salt;
R3β, R5β and R6β are independently selected from H, OH, SH, halo, alkyl, CF3, O-alkyl, CO2H, NH2, aminoalkyl, aminodialkyl, SO3H, sulfonamine, sulfonaminodi- and mono-alkyl, α-aminoacid, heterocycle, heteroaryl, OC(R1)2CO2H, SC(R1)2CO2H, or NHC(R1)2CO2H; or its pharmaceutically acceptable salt; and
R1 is H, or lower alkyl.

In yet another preferred embodiment, the invention provides trans compounds of formula (II) and their pharmaceutically acceptable salts or prodrugs thereof:
wherein;
R2α, and R6α are independently H and,
R4β, R3α, R4α, R5α and R6α are OMe and,
R3β, R5β and R6β are independently selected from H, OH, SH, halo, alkyl, CF3, O-alkyl, CO2H, NH2, aminoalkyl, aminodialkyl, SO3H, sulfonamine, sulfonaminodi- and mono-alkyl, α-aminoacid, heterocycle, heteroaryl, C(R1)2CO2H, OC(R1)2CO2H, SC(R1)2CO2H, or NHC(R1)2CO2H; or its pharmaceutically acceptable salt;

R1 is H, or lower alkyl.

In yet another preferred embodiment, the invention provides trans compounds of formula (II) and their pharmaceutically acceptable salts or prodrugs thereof:
wherein;

R2α and R6α are H and,

R3β, R4β, R3α, R4α and R5α are OMe and,

R2β, R5β and R6β are independently selected from H, OH, SH, halo, alkyl, CF3, O-alkyl, CO2H, NH2, aminoalkyl, aminodialkyl, SO3H, sulfonamine, sulfonaminodi- and mono-alkyl, α-aminoacid, heterocycle, heteroaryl, C(R1)2CO2H, OC(R1)2CO2H, SC(R1)2CO2H, or NHC(R1)2CO2H; or its pharmaceutically acceptable salt;

R1 is H, or lower alkyl.

In yet another embodiment, the invention provides trans compounds of formula (II) and their pharmaceutically acceptable salts or prodrugs thereof:
wherein;

R3β, R4β and R6β are H;

R4β is OMe and,

R2β is C(R1)2CO2H, OC(R1)2CO2H, SC(R1)2CO2H, or NHC(R1)2CO2H; or its pharmaceutically acceptable salt;

R2α–R6α are independently selected from H, OH, SH, halo, alkyl, CF3, O-alkyl, CO2H, NH2, aminoalkyl, aminodialkyl, sulfonic acid, sulfonamine, sulfonaminodi- and mono-alkyl, α-amrinoacid, heterocycle, heteroaryl, C(R1)2CO2H, OC(R1)2CO2H, SC(R1)2CO2H, or NHC(R1)2CO2H; or its pharmaceutically acceptable salt;

R1 is H, or lower alkyl.

In yet another embodiment, the invention provides trans compounds of formula (II) and their pharmaceutically acceptable salts or prodrugs thereof:
wherein;

R3β, R5β and R6β are H;

R2β and R4β are OMe;

R2α–R6α are independently selected from H, OH, SH, halo, alkyl, CF3, O-alkyl, CO2H, NH2, aminoalkyl, aminodialkyl, sulfonic acid, sulfonamine, sulfonaminodi- and mono-alkyl, α-aminoacid, heterocycle, heteroaryl, C(R1)2CO2H, OC(R1)2CO2H, SC(R1)2CO2H, or NHC(R1)2CO2H; or its pharmaceutically acceptable salt;

R1 is H, or lower alkyl.

In yet another embodiment, the invention provides trans compounds of formula (II) and their pharmaceutically acceptable salts or prodrugs thereof:
wherein;

R2β, R5β and R6β are H;

R3β and R4β are OMe;

R2α–R6α are independently selected from H, OH, SH, halo, alkyl, CF3, O-alkyl, CO2H, NH2, aminoalkyl, aminodialkyl, sulfonic acid, sulfonamine, sulfonaminodi- and mono-alkyl, α-aminoacid, heterocycle, heteroaryl, C(R1)2CO2H, OC(R1)2CO2H, SC(R1)2CO2H, or NHC(R1)2CO2H; or its pharmaceutically acceptable salt;

R1 is H, or lower alkyl.

In yet another embodiment, the invention provides trans compounds of formula (II) and their pharmaceutically acceptable salts or prodrugs thereof:
wherein;

R2α, R3α and R6α are H;

R4β is OMe and,

R4α and R5α together form a five or six membered substituted heterocylic ring and, R2 is OC(R1)2CO2H, SC(R1)2CO2H, or NHC(R1)2CO2H; or its pharmaceutically acceptable salt;

R3β, R5β and R6β are independently selected from H, OH, SH, halo, alkyl, CF3, O-alkyl, CO2H, NH2, aminoalkyl, aminodialkyl, sulfonic acid, sulfonamine, sulfonaminodi- and mono-alkyl, α-aminoacid, heterocycle, heteroaryl, C(R1)2CO2H, OC(R1)2CO2H, SC(R1)2CO2H, or NHC(R1)2CO2H; or its pharmaceutically acceptable salt; and R1 is H, or lower alkyl.

In yet another embodiment, the invention provides trans compounds of formula (II) and their pharmaceutically acceptable salts or prodrugs thereof:
wherein;

R2α, R3α and R6α are H;

R4α and R5α together form a five or six membered substituted heterocylic ring;

R2β and R4β are methoxy;

R3β, R5β and R6β are independently selected from H, OH, SH, halo, alkyl, CF3, O-alkyl, CO2H, NH2, aminoalkyl, aminodialkyl, sulfonic acid, sulfonamine, sulfonaminodi- and mono-alkyl, α-aminoacid, heterocycle, heteroaryl, C(R1)2CO2H, OC(R1)2CO2H, SC(R1)2CO2H, or NHC(R1)2CO2H; or its pharmaceutically acceptable salt; and R1 is H, or lower alkyl.

In yet another embodiment, the invention provides trans compounds of formula (II) and their pharmnaceutically acceptable salts or prodrugs thereof:
wherein;

R2α, R2α and R6α are H;

R4α and R5α together form a five or six membered substituted heterocylic ring;

R3β and R4β are methoxy;

R2β, R5β and R6β are independently selected from H, OH, SH, halo, alkyl, CF3, O-alkyl, CO2H, NH2, aminoalkyl, aminodialkyl, SO3H, sulfonamine, sulfonaminodi- and mono-alkyl, α-aminoacid, heterocycle, heteroaryl, C(R1)2CO2H, OC(R1)2CO2H, SC(R1)2CO2H, or NHC(R1)2CO2H; or its pharmaceutically acceptable salt; and R1 is H, or lower alkyl.

In yet another embodiment, the invention provides trans compounds of formula (II) and their pharmaceutically acceptable salts or prodrugs thereof:
wherein;

R3β and R6β are H;

R2β is methoxy and,

R4β is selected from OC(R1)2CO2H, SC(R1)2CO2H, or NHC(R1)2CO2H; or its pharmaceutically acceptable salt;

R2α–6α are independently selected from H, OH, SH, halo, alkyl, CF3, O-alkyl, CO2H, NH2, aminoalkyl, aminodialkyl, sulfonic acid, sulfonamine, sulfonaminodi- and mono-alkyl, α-aminoacid, heterocycle, heteroaryl, C(R1)2CO2H, OC(R1)2CO2H, SC(R1)2CO2H, or NHC(R1)2CO2H; or its pharmaceutically acceptable salt;

R1 is H, or lower alkyl.

In yet another embodiment, the invention provides trans compounds of formula (II) and their pharmaceutically acceptable salts or prodrugs thereof:
wherein;

R3β, R6α and R6β are H;

R4β is OMe;

R2β is selected from OC(R1)2CO2H, SC(R1)2CO2H, or NHC(R1)2CO2H; or its pharmaceutically acceptable salt;

R1 is H, or lower alkyl; and (R2α and R3α), (R3α and R4α) or (R4α and R5α) join to form a 5 or 6 membered optionally substituted heteroaryl or heterocycle, or optionally conjugated to another optionally substituted carbocycle, aryl, or heteroaryl.

In yet another embodiment the invention provides trans compounds of formula (II) and a pharmaceutically acceptable salts or prodrugs:
wherein;

R5β is heteroaryl preferably 2-benzothienyl and, 2-thienyl and,

R2β and R4β are independently H, or OMe and,

R3β and R6β and R6α are H and,

R2α, R3α, R4α and R5α are independently H, OH, alkoxy, halo, heteroaryl group, or OCHR1CO2H; or its pharmaceutically acceptable salt; and R1 is H, or lower alkyl.

In another preferred embodiment the invention provides trans compounds of formula (II) and a pharmaceutically acceptable salts or prodrugs:
wherein;

R4α is alkoxy, halo, preferably F, OC(R1)2CO2H, SC(R1)2CO2H, or NHC(R1)2CO2H; or its pharmaceutically acceptable salt;

R1 is H, or lower alkyl, preferably methyl;

R2α, R6α, R3β and R6β are H and,

R3α, R5α, R2β and R4β are selected from electron donating groups including but not limited to amino, thiol, alkylthio, alkoxy, preferably OMe;

R5β is an heteroaryl including furanyl, pyrrolyl, thienyl or pyridinyl, but preferably benzothienyl.

In another preferred embodiment the invention provides trans compounds of formula (II) and a pharmaceutically acceptable salts or prodrugs:
wherein;

R2β is H, alkoxy, hydroxyl, OC(R1)2CO2H, SC(R1)2CO2H, or NHC(R1)2CO2H; or its pharmaceutically acceptable salt;

R1 is H, or lower alkyl, preferably Me; R4β, R5α and R2α are independently hydroxy or alkoxyl, preferably methoxy;

R2α, R6α, R3β and R6β are independently H; and R4α is hydroxy, alkoxy or halogen, preferably F.

In another preferred embodiment the compounds of the formula (II) and a pharmaceutically acceptable salts or prodrugs:
wherein;

R2β is H, hydroxy, alkoxy, OC(R1)2CO2H, SC(R1)2CO2H, or NHC(R1)2CO2H; or its pharmaceutically acceptable salt;

R1 is H, or lower alkyl, preferably methyl; R4β and R3α are independently hydroxyl or alkoxy, preferably methoxy;

R2α, R6α, R3α and R6β are H;

R5β is heteroaryl, preferably 2-thienyl or 2-benzo[b]thienyl; and

R4α and R5α join to form a 5, 6 or 7 membered optionally substituted carbocycle, aryl, heteroaryl or heterocycle, optionally conjugated to another optionally substituted carbocycle, aryl, or heteroaryl.

In another preferred embodiment the trans compounds of the formula (II) and a pharmaceutically acceptable salts or prodrugs:
wherein;

R3α, R5α, R6α, R2β, R5β and R6β are H;

R2α, R3β and R4β are independently halo, preferably F, hydroxyl or alkoxy, preferably methoxy; and R4α is an heteroaryl preferably 2-thienyl.

In another preferred embodiment the trans compounds of formula (II) and a pharmaceutically acceptable salts or prodrugs:
wherein;

R3α, R5α, R6α, R2β and R4β are independently hydroxy or alkoxy, preferably methoxy;

R2α, R6α, R3β and R6α are H;

R4α is OC(R1)2heterocycle or its pharmaceutically acceptable salt;

R1 is H, or lower alkyl; and

R5β is heteroaryl preferably benzo[b]thienyl.

In another alternative embodiment the trans compounds of formula (II) and a pharmaceutically acceptable salts or prodrugs:
wherein;

at least one of R3α, R4α, R4β, or R5β is selected from a group consisting of the moieties in the following table (1):

TABLE 1

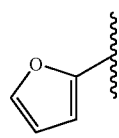

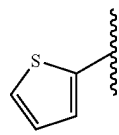

TABLE 1-continued
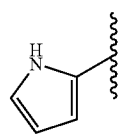
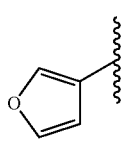
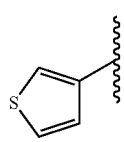
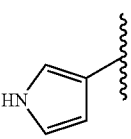
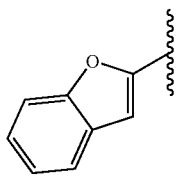
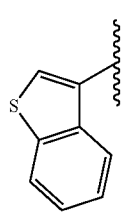
TABLE 1-continued
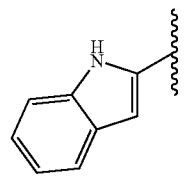
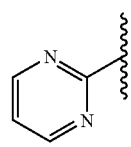
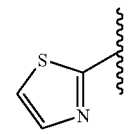
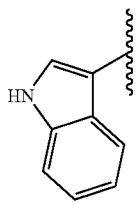
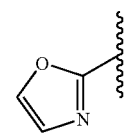
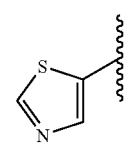

TABLE 1-continued
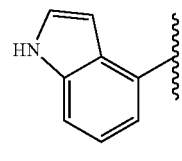
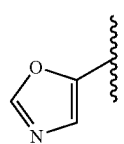
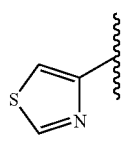
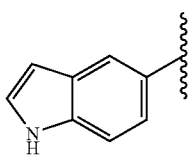
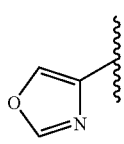
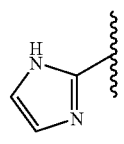
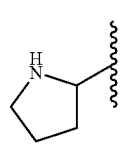
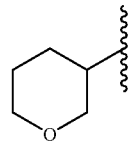
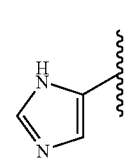
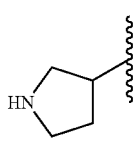
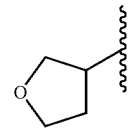
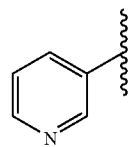
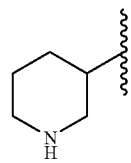

TABLE 1-continued

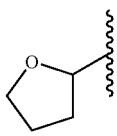

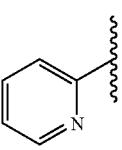

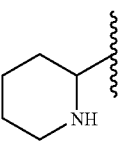

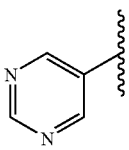

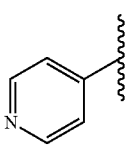

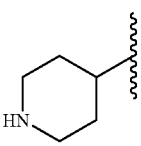

and the remaining Rα/β groups are selected independently from H; halogen, thio, cyano, nitro, optionally substituted alkyl; cycloalkyl; hydroxy; alkoxy; alkylthio; alkylamino, aminoalkyl, haloalkylthio; haloalkyl; carboxyl derivatives; aryloxy; arylalkoxy; heteroaryloxy; heteroarylalkoxy, amido; acylamino; amino, dialkylamino; trifluoroalkoxy; alkylsulfonyl, haloalkylsulfonyl; sulfonic acid; sulfonate, sulfate, sulfinic acid, sulfenic acid, sulfamide, sulfonamide; sulfoxide, metal sulfinate, phosphate, phosphonate, metal phosphonate, phosphinate aminocarbonyl; alkenyl; alkynyl; alditol, carbohydrate, carbocycle, aryl, heteroaryl and heterocycle; or the remaining Rα/β groups can join to form a 5, 6 or 7 membered optionally substituted carbocycle, aryl, heteroaryl or heterocycle, optionally fused to another optionally substituted carbocycle, aryl, heteroaryl, or heterocycle.

Examples of active chalcone derivatives prepared in this invention are listed in Table 2.

TABLE 2

| X | Z |
|---|---|
| 4-carboxymethoxy-3,5-dimethoxy, sodium salt | 2,4-dimethoxy-5-(benzo[b]thien-2-yl) |
| 2,4,6-trimethoxy | 2,4-difluoro |
| 2,3-dichloro-4-methoxy | 5-bromo-2-methoxy |
| 2,4,6-trimethoxy | 4-hydroxy-3,5-dimethoxy |
| 3,5-dimethoxy-4-(4-methoxybenzyloxy) | 3,4,5-trimethoxy |
| 3,4,5-trimethoxy | 5-bromo-2-methoxy |
| 2,3,4-trimethoxy | 3-bromo-4,5-dimethoxy |
| 3,4,5-trimethoxy | 3,4-dimethoxy-5-phenyl |
| 4-hydroxy-3,5-dimethoxy | 2,4-dimethoxy-5-(benzo[b]thien-2-yl) |
| 4-carboxymethoxy-3,5-dimethoxy | 2,4-dimethoxy-5-(benzo[b]thien-2-yl) |
| 2,3,4-trimethoxy | 5-(benzo[b]thien-2-yl)-3,4-dimethoxy |
| 3,4,5-trimethoxy | 2-methoxy-5-(4-methylthien-2-yl) |
| 3,4-dimethoxy | 2-methoxy-5-(5-methylthien-2-yl) |
| 3,4,5-trimethoxy | 2-methoxy-5-(5-methylthien-2-yl) |
| 3,5-dimethoxy-4-(1,4-benzodioxan-3-methoxy) | 3,4,5-trimethoxy |
| 2,5-dimethoxy | 2-methoxy-5-(thien-2-yl) |
| 3,4,5-trimethoxy | 3,4-dimethoxy-5-(thien-2-yl) |
| 3,4-dichloro-2-hydroxy, sodium salt | 2-methoxy-5-(thien-2-yl) |
| 3,4-dimethoxy | 2-methoxy-5-(4-methylthien-2-yl) |
| 3,4,5-trimethoxy | 3,4-dimethoxy-5-(3-pyridyl) |
| 3,4,5-trimethoxy | 2,4-dimethoxy-5-(thien-2-yl) |
| 3,4,5-trimethoxy | 5-bromo-2,4-dimethoxy |
| 3,5-dimethoxy | 2-methoxy-5-(thien-2-yl) |
| 4-iodo-2-methoxy | 2-methoxy-5-(thien-2-yl) |
| 4-(3,4-dimethoxybenzyloxy)-3-methoxy | 3,4,5-trimethoxy |
| 4-(3,4-dimethoxybenzyloxy)-3,5-dimethoxy | 3,4,5-trimethoxy |
| 2,4,5-trimethoxy | 3,4,5-trimethoxy |
| 3,4,5-trimethoxy | 2-bromo-4,5-dimethoxy |
| 3,4-dichloro-2-hydroxy | 5-bromo-2-methoxy |
| 3-methoxy-4-(3,4,5-trimethoxybenzyloxy) | 3,4,5-trimethoxy |
| 3-methoxy-4-(4-pyridylmethoxy), hydrogen chloride | 2-methoxy-5-(thien-2-yl) |
| 3-methoxy-4-(2-pyridylmethoxy), hydrogen chloride | 2-methoxy-5-(thien-2-yl) |
| 2-methoxy-4-(thien-2-yl) | 3,4-difluoro |
| 3,4,5-trimethoxy | 5-(benzo[b]thien-2-yl)-2-methoxy |
| 3,4-dichloro-2-hydroxy | 2-methoxy-5-(thien-2-yl) |
| 3,4-dimethoxy | 5-(benzo[b]thien-2-yl)-2-methoxy |
| 2,3,4-trimethoxy | 2,4-dimethoxy-5-(thien-2-yl) |

TABLE 2-continued

[Structure: 1,3-diphenyl-2-propen-1-one (chalcone) with X substituents on left ring and Z substituents on right ring]

| X | Z |
|---|---|
| 3-methoxy-4-(2-pyridylmethoxy) | 2-methoxy-5-(thien-2-yl) |
| 4-(fur-2-ylmethoxy)-3,5-dimethoxy | 3,4,5-trimethoxy |
| 4-iodo-2-methoxy | 3,4,5-trimethoxy |
| 2,4,6-trimethoxy | 3-bromo-4,5-dimethoxy |
| 3,4-methylenedioxy | 2-methoxy-5-(5-methylthien-2-yl) |
| 4-hydroxy-3,5-dimethoxy, sodium salt | 2,4-dimethoxy-5-(benzo[b]thien-2-yl) |
| 3-methoxy-4-(3-pyridylmethoxy) | 2-methoxy-5-(thien-2-yl) |
| 4-methoxy | 5-(benzo[b]thien-2-yl)-2-methoxy |
| 3,5-dimethoxy-4-(3,4-methylenedioxybenzyloxy) | 3,4,5-trimethoxy |
| 3,5-dimethoxy-4-(thien-2-ylmethoxy) | 3,4,5-trimethoxy |
| 3,4,5-trimethoxy | 3-fluoro-4-methoxy |
| 3,4-dimethoxy | 3-bromo-4,5-dimethoxy |
| 2,3,4-trimethoxy | 3,4-dimethoxy-5-(thien-2-yl) |
| 3,5-dimethoxy-4-(3,4,5-trimethoxybenzyloxy) | 3,4,5-trimethoxy |
| 3,4,5-trimethoxy | 5-(5-acetylthien-2-yl)-3,4-dimethoxy |
| 4-methoxy | 2-methoxy-5-(thien-2-yl) |
| 2,6-dimethoxy | 2-methoxy-5-(thien-2-yl) |
| 3,4-dimethoxy | 2-methoxy-5-(thien-2-yl) |
| 2,4,6-trimethoxy | 2-methoxy-5-(thien-2-yl) |
| 3,4,5-trimethoxy | 2-methoxy-5-(thien-2-yl) |
| 5-(2,4-dimethoxyphenyl) | 3,4,5-trimethoxy |
| 2-bromo-4,5-dimethoxy | 2-bromo-4,5-dimethoxy |
| 3,4,5-trimethoxy | 4-hydroxy |
| 3-methoxy-4-(4-methoxybenzyloxy) | 3,4,5-trimethoxy |
| 4-(4-ethoxycarbonyl-benzyloxy)-3-methoxy | 2-methoxy-5-(thien-2-yl) |
| 4-(2,3-isopropylidenedioxy-1-propoxy)-3,5-dimethoxy | 5-(benzo[b]thien-2-yl)-2,4-dimethoxy |
| 3-methoxy-4-(4-pyridylmethoxy) | 2-methoxy-5-(thien-2-yl) |
| 4-(3-acetylphenyl)-2-methoxy | 3,4,5-trimethoxy |
| 3,4,5-trimethoxy | 3-bromo-4,5-dimethoxy |
| 3,4-methylenedioxy | 5-bromo-2-methoxy |
| 3,4-methylenedioxy | 2-methoxy-5-(thien-2-yl) |
| 3,4-methylenedioxy | 2-methoxy-5-(4-methylthien-2-yl) |
| 2-methoxy-5-(thien-2-yl) | 4-ethoxy-3-fluoro |
| 3,4,5-trimethoxy | 5-(benzo[b]thien-2-yl)-2-carboxymethoxy-4-methoxy, sodium salt |
| 3,4,5-trimethoxy | 5-(benzo[b]thien-2-yl)-3,4-dimethoxy |
| 3,4,5-trimethoxy | 5-(benzo[b]thien-2-yl)-2,4-dimethoxy |
| 4-(4-carboxybenzyloxy)-3-methoxy | 2-methoxy-5-(thien-2-yl) |
| 3,5-dimethoxy-4-(2-methoxyethoxy) | 3,4,5-trimethoxy |
| 2,3,4-trimethoxy | 5-(4-formylphenyl)-3,4-dimethoxy |
| 2,4-dimethoxy | 4-trifluoromethyl |
| 3,4-difluoro | 2-methoxy-5-(thien-2-yl) |
| 3,4,5-trimethoxy | hydrogen |
| 4-(3-chlorophenyl) | 3,4,5-trimethoxy |
| 3,4,5-trimethoxy | 4-(thien-2-yl) |
| 5-(3-chlorophenyl)-2,4-dimethoxy | 3,4,5-trimethoxy |
| 4-(4-aminobenzyloxy)-3-methoxy | 2-methoxy-5-(thien-2-yl) |
| 3-methoxy-4-(3,4-methylenedioxybenzyloxy) | 3,4,5-trimethoxy |
| 4-hydroxy-3-methoxy | 2-methoxy-5-(thien-2-yl) |
| 2,3,4-trimethoxy | 5-(benzo[b]thien-2-yl)-2,4-dimethoxy |
| 3,4,5-trimethoxy | 5-(benzo[b]thien-2-yl)-2-carboxymethoxy-4-methoxy |
| 3,5-di-tert-butyl-4-methoxy | hydrogen |
| 3,5-dimethoxy-4-(2-morpholinoethoxy) | 5-(benzo[b]thien-2-yl)-2,4-dimethoxy |
| 2-methoxy-4-(3-methoxyphenyl) | 2-methoxy-5-(thien-2-yl) |
| 3,4-dimethoxy | 5-(benzo[b]thien-2-yl)-2,4-dimethoxy |
| 3,4,5-trimethoxy | 4-bromo |
| 2,5-dimethoxy-4-(thien-2-yl-methoxy) | 2-methoxy-5-(thien-2-yl) |
| 3,4-dimethoxy | 4-(thien-2-yl) |
| 2,4-dihydroxy | 4-hydroxy |
| 5-bromo-2,4-dimethoxy | 3,4,5-trimethoxy |
| 2,4,5-triethoxy | 3-bromo-4,5-dimethoxy |
| 4-methoxy | 3,4-dimethoxy |
| 2-methoxy-4-(thien-2-yl) | 2-methoxy-4-(thien-2-yl) |
| 3,5-di-tert-butyl-4-methoxy | 4-methoxy |
| hydrogen | hydrogen |
| 4-fluoro | 4-fluoro |
| hydrogen | 4-nitro |
| 4-methoxy | hydrogen |
| 3,4-dichloro-2-hydroxy | 5-(benzo[b]thien-2-yl)-2-methoxy |
| 3-chloro | hydrogen |
| 3,5-di-tert-butyl-4-hydroxy | 4-methoxy |
| 4-methyl | 3,5-di-tert-butyl-4-hydroxy |
| hydrogen | 3,5-di-tert-butyl-4-hydroxy |
| 3-methoxy-4-(4-tert-butyloxy-carbonylaminobenzyloxy) | 2-methoxy-5-(thien-2-yl) |
| hydrogen | 2,4,6-triisopropyl |
| 4-bromo | 3,4,5-trimethoxy |
| 4-benzyloxy-3,5-dimethoxy | 3-bromo-4,5-dimethoxy |
| 3,5-dimethoxy-4-[isopropylidene-glucofuranose-lactone ether] | 5-(benzo[b]thien-2-yl)-2,4-dimethoxy |

Alternative embodiments include the compounds illustrated below, or their pharmaceutically acceptable salts, wherein the variables are as defined above.

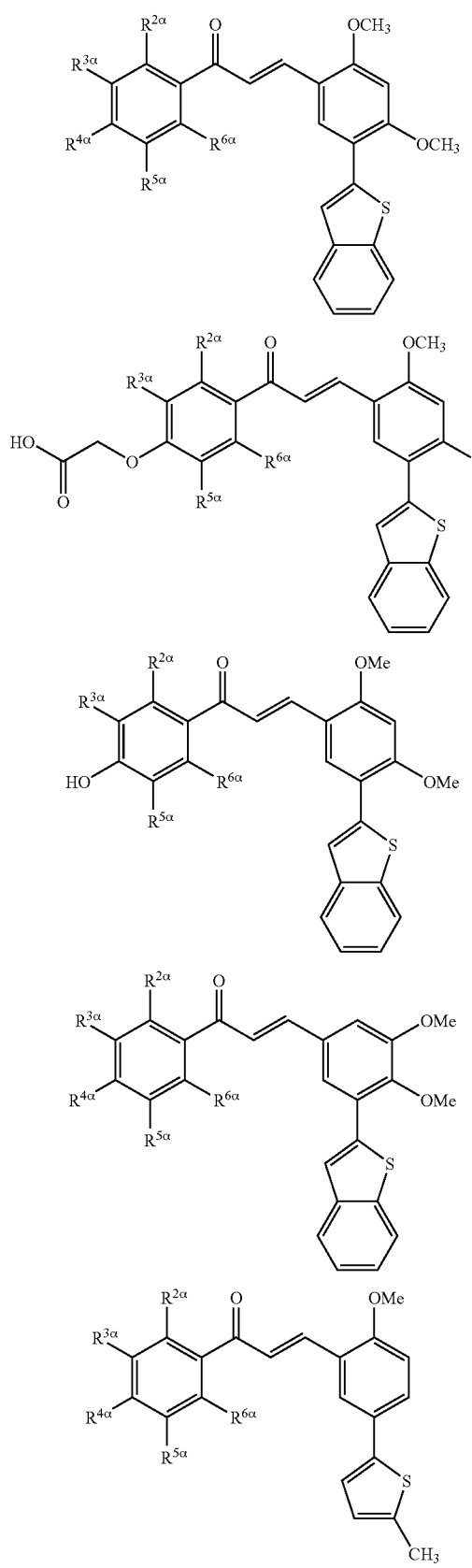
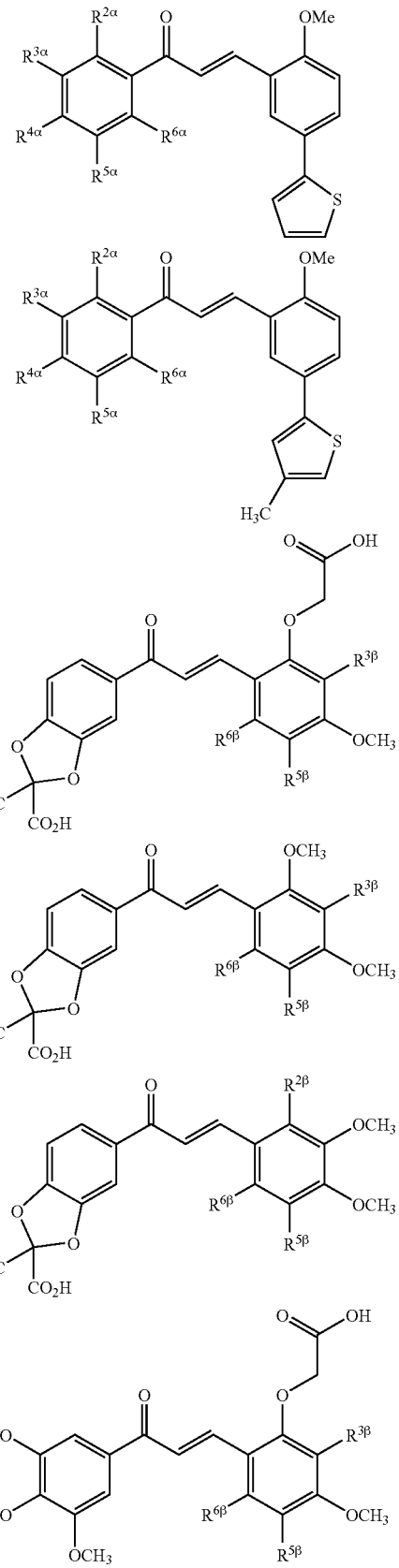
-continued

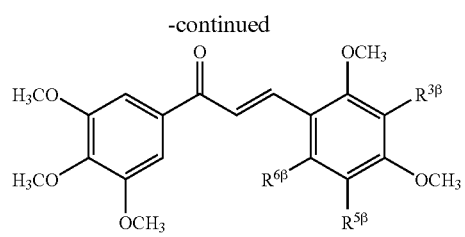
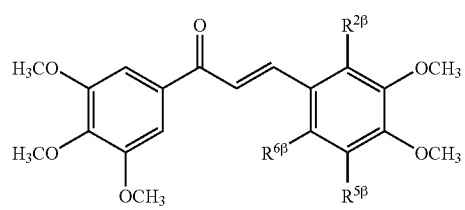
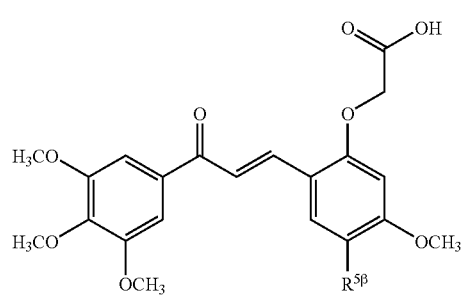
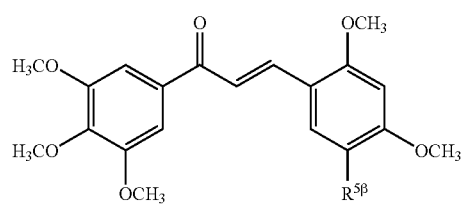
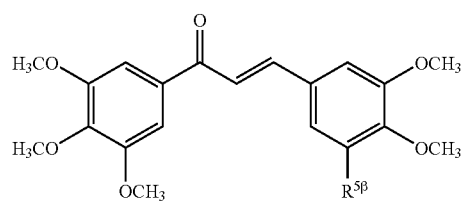
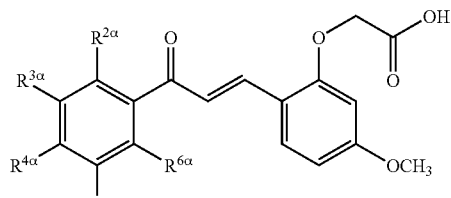
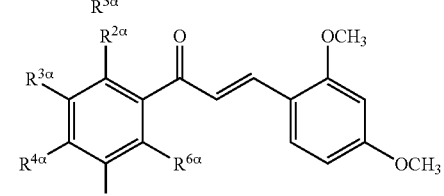
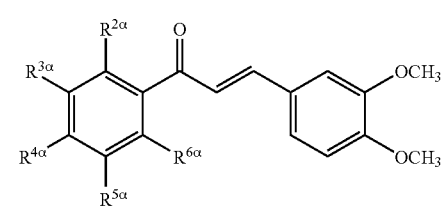
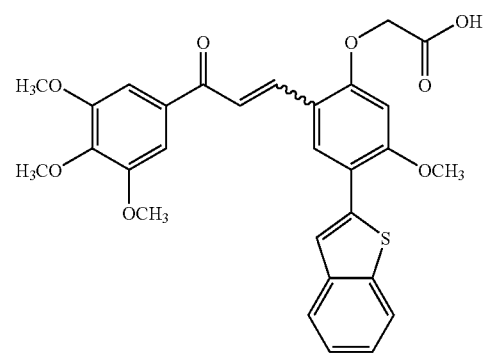
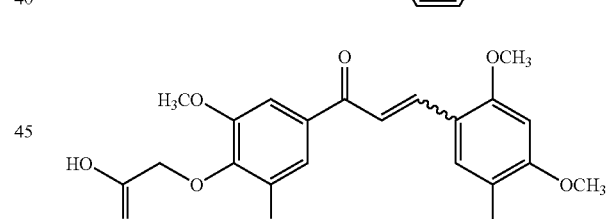
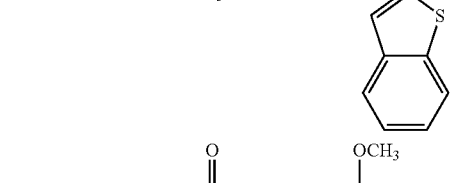
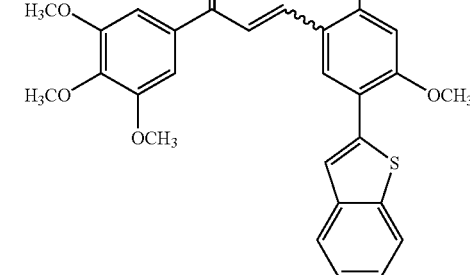
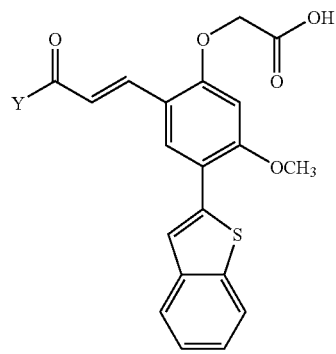
wherein Y is a phenyl ring conjugated to another heteroaromatic or heterocycle.

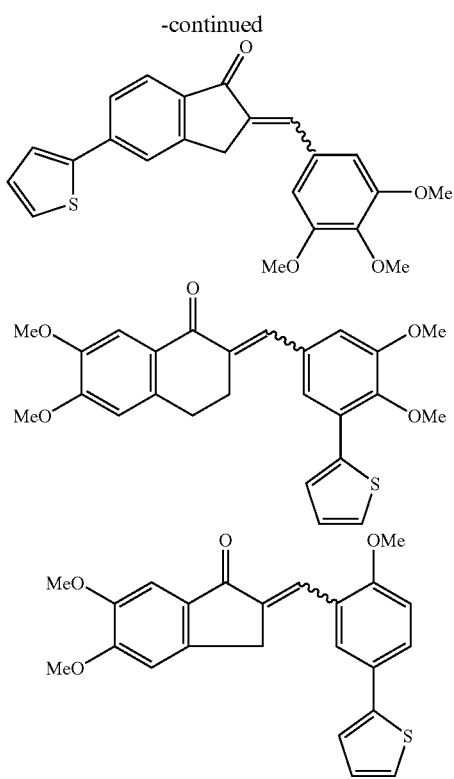

In yet another embodiment, the compound is selected from the following:

3-[5-(benzo[b]thien-2-yl)-2,4-dimethoxyphenyl]-1-(4-carboxymethoxy-3,5-dimethoxyphenyl)-2-propen-1-one sodium salt;
3-[2,4-dimethoxy-5-(thien-2-yl)phenyl]-1-(4-carboxyrnethoxy-3,5-dimethoxyphenyl)-2-propen-1-one;
3-[2,4-dimethoxy-5-(thien-2-yl)phenyl]-1-(4-carboxymethoxy-3,5-dimethoxyphenyl)-2-propen-1-one sodium salt;
3-[5-(benzo[b]thien-2-yl)-2,4-dimethoxyphenyl]-1-(4-hydroxy-3,5-dimethoxyphenyl)-2-propen-1-one;
3-[2,4-dimethoxy-5-(thien-2-yl)phenyl]-1-(4-hydroxy-3,5-dimethoxyphenyl)-2-propen-1-one;
3-[5-(benzo[b]thien-2-yl)-2,4-dimethoxyphenyl]-1-(4-carboxymethoxy-3,5-dimethoxyphenyl)-2-propen-1-one;
3-[2,4-dimethoxy-5-(thien-2-yl)-phenyl]-1-(4-carboxymethoxy-3,5-dimethoxyphenyl)-2-propen-1-one;
3-[5-(benzo[b]thien-2-yl)-3,4-dimethoxyphenyl]-1-(2,3,4-trimethoxyphenyl)-2-propen-1-one;
3-[2-methoxy-5-(4-methylthien-2-yl)phenyl]-1-(3,4,5-trimethoxy phenyl)-2-propen-1-one;
3-[2-methoxy-5-(5-methylthien-2-yl)phenyl]-1-(3,4-dimethoxyphenyl)-2-propen-1-one;
3-[2-methoxy-5-(5-methylthien-2-yl)phenyl]-1-(3,4,5-trimethoxy phenyl)-2-propen-1-one;
3-[2-methoxy-5-(thien-2-yl)phenyl]-1-(2,5-dimethoxyphenyl)-2-propen-1-one;
3-[3,4-dimethoxy-5-(thien-2-yl)phenyl]-1-(3,4,5-trimethoxyphenyl)-2-propen-1-one;
3-[2-methoxy-5-(thien-2-yl)phenyl]-1-(3,4-dichloro-2-hydroxyphenyl)-2-propen-1-one sodium salt;
3-[2-methoxy-5-(4-methylthien-2-yl)phenyl]-1-(3,4-dimethoxyphenyl)-2-propen-1-one;
3-[3,4-dimethoxy-5-(3-pyridyl)phenyl]-1-(3,4,5-trimethoxyphenyl)-2-propen-1-one;
3-[2,4-dimethoxy-5-(thien-2-yl)phenyl]-1-(3,4,5-trimethoxyphenyl)-2-propen-1-one;
3-[2-methoxy-5-(thien-2-yl)phenyl]-1-(3,5-dimethoxyphenyl)-2-propen-1-one;
3-[2-methoxy-5-(thien-2-yl)phenyl]-1-(4-iodo-2-methoxyphenyl)-2-propen-1-one;
3-[2-methoxy-5-(thien-2-yl)phenyl]-1-(3-methoxy-4-(4-pyridylmethoxyphenyl)-2-propen-1-one, hydrochloride salt;
3-[2-methoxy-5-(thien-2-yl)phenyl]-1-(3-methoxy-4-(2-pyridylmethoxyphenyl)-2-propen-1-one hydrochloride salt;
3-(3,4-difluorophenyl)-1-[2-methoxy-4-(thien-2-yl)phenyl]-2-propen-1-one;
3-[5-(benzo[b]thien-2-yl)-2-methoxyphenyl]-1-(3,4,5-trimethoxyphenyl)-2-propen-1-one;
3-[2-methoxy-5-(thien-2-yl)phenyl]-1-(3,4-dichloro-2-hydroxyphenyl)-2-propen-1-one;
3-[5-(benzo[b]thien-2-yl)-2-methoxyphenyl]-1-(3,4-dimethoxyphenyl)-2-propen-1-one;
3-[2,4-dimethoxy-5-(thien-2-yl)phenyl]-1-(2,3,4-trimethoxyphenyl)-2-propen-1-one;
3-[2-methoxy-5-(thien-2-yl)phenyl]-1-(3-methoxy-4-(2-pyridylmethoxphenyl)-2-propen-1-one;
3-[2-methoxy-5-(5-methylthien-2-yl)phenyl]-1-(3,4-methylenedioxyphenyl)-2-propen-1-one;
3-[5-(benzo[b]thien-2-yl)-2,4-dimethoxyphenyl]-1-(4-hydroxy-3,5-dimethoxyphenyl)-2-propen-1-one sodium salt;
3-[2-methoxy-5-(thien-2-yl)phenyl]-1-(3-methoxy-4-(3-pyridylmethoxphenyl)-2-propen-1-one;
3-[5-(benzo[b]thien-2-yl)-2-methoxyphenyl]-1-(4-methoxyphenyl)-2-propen-1-one;
3-[3,4-dimethoxy-5-(thien-2-yl)phenyl]-1-(2,3,4-trimethoxyphenyl)-2-propen-1-one;
3-[5-(5-acetylthien-2-yl)-3,4-dimethoxyphenyl]-1-(3,4,5-trimethoxyphenyl)-2-propen-1-one;
3-[2-methoxy-5-(thien-2-yl)phenyl]-1-(4-methoxyphenyl)-2-propen-1-one;
3-[2-methoxy-5-(thien-2-yl)phenyl]-1-(2,6-dimethoxyphenyl)-2-propen-1-one;
3-[2-methoxy-5-(thien-2-yl)phenyl]-1-(3,4-dimethoxyphenyl)-2-propen-1-one;
3-[2-methoxy-5-(thien-2-yl)phenyl]-1-(2,4,6-trimethoxyphenyl)-2-propen-1-one;
3-[2-methoxy-5-(thien-2-yl)phenyl]-1-(3,4,5-trimethoxyphenyl)-2-propen-1-one;
3-[2-methoxy-5-(thien-2-yl)phenyl]-1-[4-(4-ethoxycarbonylenzyloxy)-3-methoxyphenyl]-2-propen-1-one;
3-[5-(benzo[b]thien-2-yl)-2,4-dimethoxyphenyl]-1-[4-(2,3-isopropylidenedioxy-1-propoxy)-3,5-dimethoxyphenyl]-2-propen-1-one;
3-[2-methoxy-5-(thien-2-yl)phenyl]-1-[3-methoxy-4-(4-pyridylmethoxy)phenyl]-2-propen-1-one;
3-[2-methoxy-5-(thien-2-yl)phenyl]-1-(3,4-methylenedioxyphenyl)-2-propen-1-one;
3-[2-methoxy-5-(4-methylthien-2-yl)phenyl]-1-(3,4-methylenedioxyphenyl)-2-propen-1-one;

3-(4-ethoxy-3-fluorophenyl)-1-[2-methoxy-5-(thien-2-yl) phenyl]-2-propen-1-one;

3-[5-(benzo[b]thien-2-yl)-2-carboxymethoxy-4-methoxyphenyl]-1-(3,4,5-trimethoxyphenyl)-2-propen-1-one sodium salt;

3-[5-(benzo[b]thien-2-yl)-4-carboxymethoxy-2-methoxyphenyl]-1-(3,4,5-trimethoxyphenyl)-2-propen-1-one;

3-[5-(benzo[b]thien-2-yl)-4-carboxymethoxy-2-methoxyphenyl]-1-(3,4,5-trimethoxyphenyl)-2-propen-1-one sodium salt;

3-[2-carboxymethoxy-4-methoxy-5-(thien-2-yl)phenyl]-1-(3,4,5-trimethoxyphenyl)-2-propen-1-one;

3-[2-carboxymethoxy-4-methoxy-5-(thien-2-yl)phenyl]-1-(3,4,5-trimethoxyphenyl)-2-propen-1-one sodium salt;

3-[4-carboxymethoxy-2-methoxy-5-(thien-2-yl)phenyl]-1-(3,4,5-trimethoxyphenyl)-2-propen-1-one sodium salt;

3-[4-carboxymethoxy-2-methoxy-5-(thien-2-yl)phenyl]-1-(3,4,5-trimethoxyphenyl)-2-propen-1-one;

3-[5-(benzo [b]thien-2-yl)-3,4-dimethoxyphenyl]-1-(3,4,5-trimethoxyphenyl)-2-propen-1-one;

3-[5-(benzo [b]thien-2-yl)-2,4-dimethoxyphenyl]-1-(3,4,5-trimethoxyphenyl)-2-propen-1-one;

3-[5-(benzo [b]thien-2-yl)-2,4-dimethoxyphenyl]-1-(3,4,5-trimethoxyphenyl)-2-buten-1-one;

3-[2-methoxy-5-(thien-2-yl)phenyl]-1-[4-(4-carboxybenzyloxy)-3-methoxyphenyl]-2-propen-1-one;

3-[2-methoxy-5-(thien-2-yl)phenyl]-1-(3,4-difluorophenyl)-2-propen-1-one;

3-[4-(thien-2-yl)phenyl]-1-(3,4,5-trimethoxyphenyl)-2-propen-1-one;

3-[2-methoxy-5-(thien-2-yl)phenyl]-1-[4-(4-aminobenzyloxy)-3-methoxyphenyl]-2-propen-1-one;

3-[2-methoxy-5-(thien-2-yl)phenyl]-1-(4-hydroxy-3-methoxyphenyl)-2-propen-1-one;

3-[5-(benzo [b]thien-2-yl)-2,4-dimethoxyphenyl]-1-(2,3,4-trimethoxyphenyl)-2-propen-1-one;

3-[5-(benzo [b]thien-2-yl)-2-carboxymethoxy-4-methoxyphenyl]-1-(3,4,5-trimethoxyphenyl)-2-propen-1-one;

3-[5-(benzo[b]thien-2-yl)-2,4-dimethoxyphenyl]-1-[3,5-dimethoxy-4-(2-morpholinoethoxy)phenyl]-2-propen-1-one;

3-[2-methoxy-5-(thien-2-yl)phenyl]-1-[-2-methoxy-4-(3-methoxyphenyl)phenyl]-2-propen-1-one;

3-[5-(benzo[b]thien-2-yl)-2,4-dimethoxyphenyl]-1-(3,4-dimethoxyphenyl)-2-propen-1-one;

3-[2-methoxy-5-(thien-2-yl)phenyl]-1-(2,5-dimethoxy-4-(thien-2-ylmethoxy)phenyl)-2-propen-1-one;

3-[4-(thien-2-yl)phenyl]-1-(3,4-dimethoxyphenyl)-2-propen-1-one;

3-[2-methoxy-4-(thien-2-yl)-phenyl]-1-[2-methoxy-4-(thien-2-yl)phenyl]-2-propen-1-one phenyl]-2-propen-1-one;

2-[[3,4-dimethoxy-5-(thien-2-yl)phenyl]ethylene]-3,4-dihydro-6,7-dimethoxy-1(2H)-naphthalenone.

Stereoisomerism and Polymorphism

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatopraphy—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

II. Definitions

The term alkyl, as used herein, unless otherwise specified, refers to a saturated straight, branched, or cyclic, primary, secondary, or tertiary hydrocarbon, including but not limited to those of C1 to C10, and preferably C1–C4, including methyl, ethyl, propyl, isopropyl, cyclopropyl, methylcyclopropyl, butyl, isobutyl, t-butyl, sec-butyl, cyclobutyl, and (cyclopropyl)methyl. The alkyl group specifically includes fluorinated alkyls such as CF3 and other halogenated alkyls such as CH2CF2, CF2CF3, the chloro analogs, and the like.

The alkyl group can be optionally substituted with one or more moieties selected from the group consisting of aryl, heteroaryl, heterocyclic, carbocycle, alkoxy, heterocycloxy, heterocylalkoxy, aryloxy; arylalkoxy; heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulfonic acid, sulfate, sulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide, substituted or unsubstituted urea connected through nitrogen including but not limited to NHCONH2 and NHCONHR; or any other desired functional group that does not inhibit the pharmacological activity of this compound, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term aryl, as used herein, and unless otherwise specified, refers to phenyl, biphenyl, or naphthyl, and preferably phenyl. The aryl group can be optionally substituted with one or more of the moieties selected from the group consisting of alkyl, heteroaryl, heterocyclic, carbocycle, alkoxy, aryloxy, aryloxy; arylalkoxy; heteroaryloxy; heteroarylalkoxy, carbohydrate, amino acid, amino acid esters, amino acid amides, alditol, halo, haloalkyl, hydroxyl, carboxyl, acyl, acyloxy, amino, amido, alkylamino, dialkylamino, arylamino, nitro, cyano, thiol, imide, sulfonic acid, sulfate, sulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene, et al., "Protective Groups in Organic Synthesis," John Wiley and Sons, Second Edition, 1991. Alternatively, adjacent groups on the aryl ring may combine to form a 5 to 7 membered carbocyclic, aryl, heteroaryl or heterocylic ring. In another embodiment, the aryl ring is substituted with an optionally substituted cycloalkyl (such as cyclopentyl or cylcohexyl), or an alkylene dioxy moiety (for example methylenedioxy).

The term heterocyclic refers to a nonaromatic cyclic group that may be partially (contains at least one double bond) or fully saturated and wherein there is at least one heteroatom, such as oxygen, sulfur, nitrogen, or phosphorus in the ring. The term heteroaryl or heteroaromatic, as used herein, refers to an aromatic that includes at least one sulfur, oxygen, nitrogen or phosphorus in the aromatic ring. Non-limiting examples of heterocylics and heteroaromatics are pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, or pteridinyl wherein said heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl.

The term thienyl refers to a five member cyclic group wherein the ring contains one sulfur atom and two double bonds. The thienyl group can optionally be substituted with one or more moieties selected from the group consisting of those described above for aryl substituents.

The term benzothienyl refers to a five member cyclic group wherein the ring contains one sulfur atom and two double bonds fused to a phenyl ring. The benzothienyl group can optionally be substituted with one or more moieties selected from the group consisting of those described above for aryl substituents.

The term aralkyl, as used herein, and unless otherwise specified, refers to an aryl group as defined above linked to the molecule through an alkyl group as defined above. The aryl and alkyl portions can be optionally substituted as described above.

The term heteroaralkyl, as used herein, and unless otherwise specified, refers to an heteroaryl group as defined above linked to the molecule through an alkyl group as defined above.

The term heterocyclealkyl, as used herein, refers to a heterocyclic group bound to the molecule through an alkyl group. The heterocyclic group and the alkyl group can be optionally substituted as described above.

The term aryloxy, as used herein, refers to an aryl group bound to the molecule through an oxygen atom. The aryl group can be optionally substituted as set out above for aryl groups.

The term heteroaryloxy, as used herein, refers to a heteroaryl group bound to the molecule through an oxygen atom. The heteroaryl group can be optionally substituted as set out above for aryl groups.

The term aralkoxy refers to an aryl group attached to an alkyl group which is attached to the molecule through an oxygen atom. The aryl and alkyl groups can be optionally substituted as described above.

The term heterocyclearalkoxy refers to a heterocyclic group attached to an aryl group attached to an alkyl-O— group. The heterocyclic, aryl and alkyl groups can be optionally substituted as described above.

The term halo or halogen, as used herein, includes chloro, bromo, iodo and fluoro.

The term alkoxy, as used herein, and unless otherwise specified, refers to a moiety of the structure —O-alkyl, wherein alkyl is as defined above. The alkyl group can be optionally substituted as described above. Alkoxy groups can include $OCF_3$, $OCH_2CF_3$, $OCF_2CF_3$ and the like.

The term alkylthio as used herein refers to an alkyl group attached to the molecule through a sulfur atom. The alkyl group can be optionally substituted as described above.

The term acyl, as used herein, refers to a group of the formula C(O)R', wherein R' is an alkyl, aryl, alkaryl or aralkyl group, or substituted alkyl, aryl, aralkyl or alkaryl, wherein these groups are as defined above.

The term "alditol," as referred to herein, and unless otherwise specified, refers to a carbohydrate in which the aldehyde or ketone group has been reduced to an alcohol moiety. The alditols of the present invention can also be optionally substituted or deoxygenated at one or more positions. Exemplary substituents include hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, amino acid, amino acid esters and amides, phosphonyl, phosphinyl, phosphoryl, thioester, thioether, oxime, hydrazine, carbamate, phosphonic acid, phosphonate, or any other viable functional group that does not inhibit the pharmacological activity of this compound. Particular exemplary substituents include amine and halo, particularly fluorine. The substituent or alditol can be either unprotected, or protected as necessary, as known to those skilled in the art, for example, as taught in Greene, et al., Protective Groups in Organic Synthesis, John Wiley and Sons, Second Edition, 1991, hereby incorporated by reference.

The alditol may have 3, 4, 5, 6 or 7 carbons. Examples of useful alditols are those derived from reduction of monosaccharides, including specifically those derived from the reduction of pyranose and furanose sugars.

The term "carbohydrate," as referred to herein, and unless otherwise specified, refers to a compound of carbon, hydrogen and oxygen that contains an aldehyde or ketone group in combination with at least two hydroxyl groups. The carbohydrates of the present invention can also be optionally substituted or deoxygenated at one or more positions. Carbohydrates thus include substituted and unsubstituted monosaccharides, disaccharides, oligosaccharides, and polysaccharides. The saccharide can be an aldose or ketose, and may comprise 3, 4, 5, 6, or 7 carbons. In one embodiment the carbohydrates are monosaccharides. In another embodiment the carbohydrates are pyranose and furanose sugars.

Non limiting examples of pyranose and furanose sugars include threose, ribulose, ketose, gentiobiose, aldose, aldotetrose, aldopentose, aldohexose, ketohexose, ketotetrose, ketopentose, erythrose, threose, ribose, deoxyribose, arabinose, xylose, lyxose, allose, altrose, glucose, mannose, gulose, idose, glactose, talose, erythrulose, ribulose, xylulose, psicose, fructose, sorbose, tagatose, dextrose, maltose, lactose, sucrose, cellulose, aldose, amylose, palatinose, trehalose, turanose, cellobiose, amylopectin, glucosamine, mannosamine, fucose, phamnose, glucuronate, gluconate, glucono-lactone, muramic acid, abequose, rhamnose, gluconic acid, glucuronic acid, and galactosamine.

The carbohydrate can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, amino acid, amino acid esters, amides, phosphonyl, phosphinyl, phosphoryl, thioester, thioether, oxime, hydrazine, carbamate, phosphonic acid, phosphonate, or any other viable functional group that does not inhibit the pharmacological activity of this compound. Particular exemplary substituents include amine and halo, particularly fluorine. The substituent or carbohydrate can be either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991.

As used herein, the term "patient" refers to warm-blooded animals or mammals, and in particular humans, who are in need of the therapy described herein. The term host, as used herein, refers to a unicellular or multicellular organism, including cell lines and animals, and preferably a human.

III. Pharmaceutically Acceptable Salt Formulations

In cases where compounds are sufficiently basic or acidic to form stable nontoxic acid or base salts, administration of the compound as a pharmaceutically acceptable salt may be appropriate. The term "pharmaceutically acceptable salts" or "complexes" refers to salts or complexes that retain the desired biological activity of the compounds of the present invention and exhibit minimal undesired toxicological effects.

Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, sulfate, nitrate, bicarbonate and carbonate salts. Alternatively, the pharmaceutically acceptable salts may be made with sufficiently basic compounds such as an amine with a suitable acid affording a physiologically acceptable anion. Alkali metal (for example, sodium, potassium or lithium) or alkaline earth metal (for example calcium) salts of carboxylic acids can also be made.

Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR+A—, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess anti-inflammatory activity, or are metabolized to a compound that exhibits such activity.

Any of the compounds described herein can be administered as a prodrug to increase the activity, bioavailability, stability or otherwise alter the properties of the compound. A number of prodrug ligands are known. In general, alkylation, acylation or other lipophilic modification of the compound will increase the stability of the chalcone. Examples of substituent groups that can replace one or more hydrogens on the compound are alkyl, aryl, steroids, carbohydrates, including sugars, 1,2-diacylglycerol and alcohols. Many are described in R. Jones and N. Bischofberger, Antiviral Research, 27 (1995) 1–17. Any of these can be used in combination with the disclosed compounds to achieve a desired effect.

IV. Inflammatory Diseases

The compounds of the present invention can be used to treat any disorder that is mediated by VCAM. VCAM is upregulated in a wide variety of disease states, including but not limited to arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, rhinitis, ischemia-reperfusion injury, post-angioplasty restenosis, chronic obstructive pulmonary disease (COPD), glomerulonephritis, Graves disease, gastrointestinal allergies, and conjunctivitis.

Nontlimiting examples of arthritis include rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, Dendonitis, tenosynovitis, bursitis), juvenile chronic, spondyloarthropaties (ankylosing spondylitis), osteoarthritis, hyperuricemia and arthritis associated with acute gout, chronic gout and systemic lupus erythematosus.

Human endothelial disorders mediated by VCAM-1 include psoriasis, eczematous dermatitis, Kaposi's sarcoma, as well as proliferative disorders of smooth muscle cells.

In yet another embodiment, the compounds disclosed herein can be selected to treat anti-inflammatory conditions that are mediated by mononuclear leucocytes.

In one embodiment, the compounds of the present invention are selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. The compounds can also be used in the prevention or treatment of graft-versus-host disease, such as sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

In addition to inhibiting the expression of VCAM-1, the disubstituted 1,3-bis-(substituted-phenyl)-2-propen-1-ones have the additional properties of inhibiting monocyte chemoattractant protein-1 (MCP-1) and smooth muscle proliferation. MCP-1 is a chemoattractant protein produced by endothelial cells, smooth muscle cells as well as macrophages. MCP-1 promotes integrin activation on endothelial cells thereby facilitating adhesion of leukocytes to VCAM-1, and MCP-1 is a chemoattractant for monocytes. MCP-1 has been shown to play a role in leukocyte recruitment in a number of chronic inflammatory diseases including atherosclerosis, rheumatoid arthritis, and asthma. Its expression is upregulated in these diseases and as such inhibition of MCP-1 expression represents a desirable property of anti-inflammatory therapeutics. Furthermore, smooth muscle cell hyperplasia and resulting tissue remodeling and decreased organ function is yet another characteristic of many chronic inflammatory diseases including atherosclerosis, chronic transplant rejection and asthma. Inhibition of the hyperproliferation of smooth muscle cells is another desirable property for therapeutic compounds.

V. Combination and Alternation Therapy

Any of the compounds disclosed herein can be administered in combination or alternation with a second biologically active agent to increase its effectiveness against the target disorder.

In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The efficacy of a drug can be prolonged, augmented, or restored by administering the compound in combination or alternation with a second, and perhaps third, agent that induces a different biological pathway from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the condition.

Any method of alternation can be used that provides treatment to the patient. Nonlimiting examples of alternation patterns include 1–6 weeks of administration of an effective amount of one agent followed by 1–6 weeks of administration of an effective amount of a second agent. The alternation schedule can include periods of no treatment. Combination therapy generally includes the simultaneous administration of an effective ratio of dosages of two or more active agents.

Illustrative examples of specific agents that can be used in combination or alternation with the chalcones of the present invention are described below in regard to asthma and arthritis. The agents set out below or others can alternatively be used to treat a host suffering from any of the other disorders listed in Section IV or that are mediated by VCAM or MCP-1. Illustrative second biologically active agents for the treatment of cardiovascular disease are also provided below.

Asthma

In one embodiment, the compound of the present invention is administered in combination or alternation with heparin, frusemide, ranitidine, an agent that effects respiratory function, such as DNAase, or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-D4-receptor antagonists such as Accolate (zafirlukast), Ziflo (zileuton), leukotriene C1 or C2 antagonists and inhibitors of leukotriene synthesis such as zileuton for the treatment of asthma, or an inducible nitric oxide synthase inhibitor.

In another embodiment, the active compound is administered in combination or alternation with one or more other prophylactic agent(s). Examples of prophylactic agents that can be used in alternation or combination therapy include but are not limited to sodium cromoglycate, Intal (cromolyn sodium, Nasalcrom, Opticrom, Crolom, Ophthalmic Crolom), Tilade (nedocromil, nedocromil sodium) and ketotifen.

In another embodiment, the active compound is administered in combination or alternation with one or more other β2-adrenergic agonist(s) (β agonists). Examples of β-adrenergic agonists (β agonists) that can be used in alternation or combination therapy include but are not limited to albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tornalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone ,Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other antihistimine(s) (H1 receptor antagonists). Examples of antihistimines (H1 receptor antagonists) that can be used in alternation or combination therapy include alkylamines, ethanolamines ethylenediamines, piperazines, piperidines or phenothiazines. Some non-limiting examples of antihistimes are Chlortrimeton (Teldrin, chlorpheniramine), Atrohist (brompheniramine, Bromarest, Bromfed, Dimetane), Actidil (triprolidine), Dexchlor (Poladex, Polaramine, dexchlorpheniramine), Benadryl (diphen-hydramine), Tavist (clemastine), Dimetabs (dimenhydrinate, Dramamine, Marmine), PBZ (tripelennamine), pyrilamine, Marezine (cyclizine), Zyrtec (cetirizine), hydroxyzine, Antivert (meclizine, Bonine), Allegra (fexofenadine), Hismanal (astemizole), Claritin (loratadine), Seldane (terfenadine), Periactin (cyproheptadine), Nolamine (phenindamine, Nolahist), Phenameth (promethazine, Phenergan), Tacaryl (methdilazine) and Temaril (trimeprazine).

Alternatively, the compound of the present invention is administered in combination or alternation with
 (a) xanthines and methylxanthines, such as Theo-24 (theophylline, Slo-Phylline, Uniphyllin, Slobid, Theo-Dur), Choledyl (oxitriphylline), aminophylline;
 (b) anticholinergic agents (antimuscarinic agents) such as belladonna alkaloids, Atrovent (ipratropium bromide), atropine, oxitropium bromide;
 (c) phosphodiesterase inhibitors such as zardaverine;
 (d) calcium antagonists such as nifedipine; or
 (e) potassium activators such as cromakalim for the treatment of asthma.

Arthritic Disorders

In one embodiment, the compound of the present invention can also be administered in combination or alternation with apazone, amitriptyline, chymopapain, collegenase, cyclobenzaprine, diazepam, fluoxetine, pyridoxine, ademetionine, diacerein, glucosamine, hylan (hyaluronate), misoprostol, paracetamol, superoxide dismutase mimics, TNFα receptor antagonists, TNFα antibodies, P38 Kinase inhibitors, tricyclic antidepressents, cJun kinase inhibitors or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-D4-receptor antagonists such as Accolate (zafirlukast), Ziflo (zileuton), leukotriene C1, C2 antagonists and inhibitors of leukotriene synthesis such as zileuton for the treatment of arthritic disorders, inducible nitric oxide sythase inhibitors.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone ,Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other non-steroidal anti-inflammatory drug(s) (NSAIDS). Examples of NSAIDS that can be used in alternation or combination therapy are carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some nonlimiting examples of COX-2 inhibitors are Celebrex (celecoxib) and Vioxx (rofacoxib). Some non-limiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Alminoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine, Hydrochloride, Bornyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucametacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lomoxicam, Loxoprofen Sodium, Lysine Aspirin, Magnesium Salicylate, Meclofenamae Sodium, Mefenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Momiflurnate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

Cardiovascular Disease

Compounds useful for combining with the compounds of the present invention for the treatment of cardiovascular disease encompass a wide range of therapeutic compounds.

Ileal bile acid transporter (IBAT) inhibitors, for example, are useful in the present invention, and are disclosed in patent application no. PCT/US95/10863, herein incorporated by reference. More IBAT inhibitors are described in PCT/US97/04076, herein incorporated by reference. Still further IBAT inhibitors useful in the present invention are described in U.S. application Ser. No. 08/816,065, herein incorporated by reference. More IBAT inhibitor compounds useful in the present invention are described in WO 98/40375, and WO 00/38725, herein incorporated by reference. Additional IBAT inhibitor compounds useful in the present invention are described in U.S. application Ser. No. 08/816,065, herein incorporated by reference.

In another aspect, the second biologically active agent is a statin. Statins lower cholesterol by inhibiting of 3-hydroxy-3-methylglutaryl coenzyme A (HMG CoA) reductase, a key enzyme in the cholesterol biosynthetic pathway. The statins decrease liver cholesterol biosynthesis, which increases the production of LDL receptors thereby decreasing plasma total and LDL cholesterol (Grundy, S. M. New Engl. J. Med. 319, 24 (1988); Endo, A. J. Lipid Res. 33, 1569 (1992)). Depending on the agent and the dose used, statins may decrease plasma triglyceride levels and may increase HDLc. Currently the statins on the market are lovastatin (Merck), simvastatin (Merck), pravastatin (Sankyo and Squibb) and fluvastatin (Sandoz). A fifth statin, atorvastatin (Parke-Davis/Pfizer), is the most recent entrant into the statin market. Any of these statins or thers can be used in combination with the chalcones of the present invention.

MTP inhibitor compounds useful in the combinations and methods of the present invention comprise a wide variety of structures and functionalities. Some of the MTP inhibitor compounds of particular interest for use in the present invention are disclosed in WO 00/38725, the disclosure from which is incorporated by reference. Descriptions of these therapeutic compounds can be found in Science, 282, 23 October 1998, pp. 751–754, herein incorporated by reference.

Cholesterol absorption antagonist compounds useful in the combinations and methods of the present invention comprise a wide variety of structures and functionalities. Some of the cholesterol absorption antagonist compounds of particular interest for use in the present invention are described in U.S. Pat. No. 5,767,115, herein incorporated by reference. Further cholesterol absorption antagonist compounds of particular interest for use in the present invention, and methods for making such cholesterol absorption antagonist compounds are described in U.S. Pat. No. 5,631,365, herein incorporated by reference.

A number of phytosterols suitable for the combination therapies of the present invention are described by Ling and Jones in "Dietary Phytosterols: A Review of Metabolism, Benefits and Side Effects," Life Sciences, 57 (3), 195–206 (1995). Without limitation, some phytosterols of particular use in the combination of the present invention are Clofibrate, Fenofibrate, Ciprofibrate, Bezafibrate, Gemfibrozil. The structures of the foregoing compounds can be found in WO 00/38725.

Phytosterols are also referred to generally by Nes (Physiology and Biochemistry of Sterols, American Oil Chemists' Society, Champaign, Ill., 1991, Table 7-2). Especially preferred among the phytosterols for use in the combinations of the present invention are saturated phytosterols or stanols. Additional stanols are also described by Nes (Id.) and are useful in the combination of the present invention. In the combination of the present invention, the phytosterol preferably comprises a stanol. In one preferred embodiment the stanol is campestanol. In another preferred embodiment the stanol is cholestanol. In another preferred embodiment the stanol is clionastanol. In another preferred embodiment the stanol is coprostanol. In another preferred embodiment the stanol is 22,23-dihydrobrassicastanol. In another embodiment the stanol is epicholestanol. In another preferred embodiment the stanol is fucostanol. In another preferred embodiment the stanol is stigmastanol.

Another embodiment the present invention encompasses a therapeutic combination of a compound of the present invention and an HDLc elevating agent. In one aspect, the second HDLc elevating agent can be a CETP inhibitor. Individual CETP inhibitor compounds useful in the present invention are separately described in WO 00/38725, the disclosure of which is herein incorporated by reference. Other individual CETP inhibitor compounds useful in the present invention are separately described in WO 99/14174, EP818448, WO 99/15504, WO 99/14215, WO 98/04528, and WO 00/17166, the disclosures of which are herein incorporated by reference. Other individual CETP inhibitor compounds useful in the present invention are separately described in WO 00/18724, WO 00/18723, and WO 00/18721, the disclosures of which are herein incorporated by reference. Other individual CETP inhibitor compounds useful in the present invention are separately described in WO 98/35937, the disclosure of which is herein incorporated by reference.

In another aspect, the second biologically active agent can be a fibric acid derivative. Fibric acid derivatives useful in the combinations and methods of the present invention comprise a wide variety of structures and functionalities which have been reported and published in the art.

In another embodiment the present invention encompasses a therapeutic combination of a compound of the present invention and an antihypertensive agent. Hypertension is defined as persistently high blood pressure. In another embodiment, the chalcone is administered in combination with an ACE inhibitor, a beta andrenergic blocker, alpha andrenergic blocker, angiotensin II receptor antagonist, vasodilator and diuretic.

VI. Pharmaceutical Compositions

Any host organism, including a pateint, mammal, and specifically a human, suffering from any of the above-described conditions can be treated by the administration of a composition comprising an effective amount of the compound of formula (I) or a pharmaceutically acceptable salt thereof, optionally in a pharmaceutically acceptable carrier or diluent.

The composition can be administered in any desired manner, including oral, topical, parenteral, intravenous, intradermal, intra-articular, intra-synovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump, or via catheter. In one embodiment, the agent and carrier are administered in a slow release formulation such as an implant, bolus, microparticle, microsphere, nanoparticle or nanosphere. For standard information on pharmaceutical formulations, see Ansel, et al., Pharmaceutical Dosage Forms and Drug Delivery Systems, Sixth Edition, Williams & Wilkins (1995).

An effective dose for any of the herein described conditions can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication. Typical systemic dosages for all of the herein described conditions are those ranging from 0.1 mg/kg to 500 mg/kg of body weight per day as a single daily dose or divided daily doses. Preferred dosages for the described conditions range from 5–1500 mg per day. A more particularly preferred dosage for the desired conditions ranges from 25–750 mg per day. Typical dosages for topical application are those ranging from 0.001 to 100% by weight of the active compound.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The compound can also be mixed with other active materials that do not impair the desired action, or with materials that supplement the desired action. The compounds can also be administered in combination with non-steroidal antiinflammatories such as ibuprofen, indomethacin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are physiological saline, bacteriostatic water, Cremophor ELTM (BASF, Parsippany, N.J.) or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Any of the compounds described herein for combination or alternation therapy can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound. This can easily be assessed by preparing the derivative and testing its anti-inflammatory activity according to known methods.

VII. Synthesis of the Active Compounds

A number of the compounds of the general formula (I) are known, whereas many of the compounds of the general formula (I) are novel compounds. The known compounds may be isolated or synthesized in accordance with methods from literature or methods analogous thereto, an non-limiting example is taught by Wade et al, Organic Chemistry Third Edition, 1995. The novel compounds may, likewise, be produced by methods known per se or methods which are analogous to such methods.

Compounds of general formula (I) are prepared by reacting an aryl or cyclic substituted ketone with an aryl or cyclic substituted aldehyde. This reaction, which is a condensation reaction, is suitably carried out under acid or base catalyzed conditions. The reaction may be suitably carried out in water or protic organic solvents such as lower alcohols (e.g. methanol, ethanol, or tert-butanol), or lower carboxylic acid (e.g. formic acid, glacial acetic acid, or propionic acid), or in aprotic organic solvents such as ethers (e.g. tetrahydrofuran, dioxane, or diethyl ether), liquid amides (e.g. dimethylformamide, or hexamethylphosphordiamide), dimethylsulfoxide, or hydrocarbons (e.g. toluene or benzene), or mixtures of such solvents. When carrying out the reaction under basic conditions, the base may be selected from sodium, lithium, potassium, barium, calcium, magnesium, aluminum, ammonium, or quarternary ammonium hydroxides, lower alkoxides (e.g. methoxides, ethoxides, tert-butoxides), carbonates, borates, oxides, hydrides, or amides of lower secondary amines (e.g. diisopropyl amides or methylphenyl amides). Primary aromatic amines such as aniline, free secondary amines such as dimethyl amine, diethyl amine, piperidine, or pyrrolidine as well as basic ion exchange resins may also be used.

Acid catalysts may be selected from hydrogen chloride, hydrogen bromide, hydrogen iodide, sulfuric acid, sulfonic acids (such as paratoluenesulfonic or methansulfonic acid), lower carboxylic acid (such as formic, acetic, or propionic acid), lower halogenated carboxylic acid (such as trifluoroacetic acid), Lewis acids (such as BF3, POCl3, PC15, FeCl3), or acid ion exchange resins.

The reaction may be carried out at temperatures in the range of 0–100° C., preferably at room temperature. The time of reaction may be from 30 minutes to 24 hours.

In the above reactions, it may be preferred or necessary to protect various sensitive or reactive groups present in the starting materials so as to prevent said groups from interfering with the reactions. Such protection may be carried out in a well-known manner as taught by Theodora Green et al., in "Protective Groups in Organic Chemistry" or of the like. The protecting group may be removed after the reaction in a manner known per se.

1,3-Bis-(substituted-phenyl)-2-propen-1-ones

The 1,3-bis-(substituted-phenyl)-2-propen-1-one compounds of formula (I) and formula (II) can be prepared by known procedures and techniques, or routine modifications thereof. General procedures for preparing compounds of formula (I) are set forth in Schemes 1 through 6.

Generic Syntheses

The 1,3-bis-(substituted-phenyl)-2-propen-1-one compounds of the present invention can be readily prepared by someone skilled in the art of organic synthesis using commonly known methods, many of which are described by D. N. Dnar in The Chemistry of Chalcones and Related Compounds (Wiley-Interscience, New York, 1981), that is incorporated herein by reference. As shown in Scheme 1 through Scheme 6, typically a substituted acetophenone is condensed with a substituted benzaldehyde in the presence of a suitable base in a common procedure known as an aldol condensation reaction. A variety of organic and inorganic bases can be used. Sodium hydroxide is a preferred inorganic base. The reaction can be carried out in a variety of different solvents. Either protoic or aprotic solvents may be used. Ethanol is preferred in the presence of an inorganic base. On either or both of the phenyl rings there is a halogen substutution, with iodo and bromo being preferred.

A heteroaryl or heterocyclic ring is then introduced to replace the halogen substitution on either one or both of the phenyl rings through a metal-catalyzed cross-coupling carbon-carbon bond forming reaction well known in the art of organic chemistry. A variety of metal-catalyzed cross coupling carbon-carbon bond forming reactions can be used. The palladium-catalyzed Suzuki reaction is preferred, and general methods for this procedure are described by A. Suzuki in Recent Advances in the Cross-Coupling Reactions of Organoboron Derivatives with Organic Electrophiles, 1995–1998 (J. Organomet. Chem. (1999), 576(1–2), 147–168), incorporated herein by reference. For the Suzuki reaction, a variety of solvents can be used. The preferred solvent for the Suzuki coupling is ethylene glycol dimethyl ether (DME). As shown in Schemes 1 and 5, this cross-coupling reaction can be done on either phenyl ring after the 1,3-bis-(substituted-phenyl)-2-propen-1-one skeleton has been assembled to provide 1,3-bis-(substituted-phenyl)-2-propen-1-ones containing one or more heteroaryl or heterocyclic ring. Alternatively, the cross-coupling reaction can be done on the individual acetophenone or benzaldehyde intermediates prior to the aldol condensation, as shown in Schemes 2 and 4. Most of the compounds of this invention are made by either one of these two methods.

As shown in Scheme 3, the aldol condensation reaction can also be carried out in an aquaeous solution using a surfactant. A variety of surfactants can be used. Cetyltrimethylammonium chloride is the preferred surfactant. This method is particularly useful when there are one or more hydroxyl substitutions on either one or both of the phenyl rings.

As shown in Scheme 6, the aldol condensation reaction can also be carried out in an aprotic solvent such as tetrahydrofuran (THF) with an organic base. The preferred solvent is THF and the preferred base is lithium diisopropylamide (LDA). In this manner an aldol reaction may take place first and the subsequent dehydration reaction may take place during aqueous workup.

Some acetophenones and benzaldehydes are not commercially available. They can be readily prepared by someone skilled in the art of organic synthesis. Since the acetophenones or benzaldehydes may also contain one or more water solubilizing groups (amines, acohols, carboxylates, phosphates, phosphonates, sulfonates, sulfates, etc) that may interfere in the reaction or that may complicate isolation of the desired product, one normally skilled in the art may choose to protect these solubilizing groups prior to the reaction using methods commonly known in the literature such as those described by T. W. Greene and P. G. M. Wuts in Protective Groups in Organic Synthesis (Wiley, New York, 1999) and A. J. Pearson and W. R. Roush in Handbook of Reagents for Organic Synthesis: Activating and Agents and Protecting Groups (Wiley, Chichester, UK, 1999), incorporated herein by reference. Preferable protecting groups include acetates to protect alcohols, esters to protect carboxylic acids, and amides or carbamates to protect amines. Compounds of the present invention include the resulting protected intermediates. One skilled in the art can selectively remove these protecting groups using well established and known procedures to give the desired deprotected heteroaryl or heterocyclic 1,3-bis-(substituted-phenyl)-2-propen-1-one products. Some protecting groups such as carboxylic esters may be removed during the aldol condensation reaction. Formation of the resulting carboxylate salts, e.g. the sodium salt, may facilitate isolation of the desired heteroaryl or heterocyclic 1,3-bis-(substituted-phenyl)-2-propen-1-one products from the reaction mixture. Alternatively, acidification of the reaction mixture prior to or during workup may facilitate the isolation of the desired free carboxylic, phosphonic, phosphinic or sulfonic acid derivatives. Various salts of the compounds of this invention can be prepared by someone skilled in the art of organic synthesis. Such salts, e.g. amine hydrochlorides, can be directly isolated from the reaction mixture after acidification or formed separately after isolation of the corresponding free amine.

The chemical reactions described above are generally disclosed in terms of their broadest applications to the preparation of the compounds of the present invention. Occasionally, the reactions may not be applicable as described to each compound included within the disclosed scope. The compounds for which this occurs will be readily recognized by those skilled in the art. In all such cases, either the reactions can successfully performed by conventional modifications recognized by those skilled in the art, e.g., by appropriate protection and deprotection of interfering groups, by changing to alternative conventional solvents or reagents, by routine modification of reaction conditions and the like, or other conventional reactions will be applicable to the preparation of the corresponding compounds of the present invention. In all preparative methods, all starting materials are known or readily prepared from known starting materials.

VIII. EXAMPLES

The following examples are understood to be illustrative only and are not intended to limit the scope of the present invention in any way. All intermediates and final products have been completely characterized by conventional proton NMR and standard analytical methods known to those skilled in the art.

Scheme 1

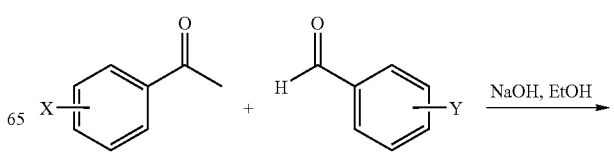

-continued

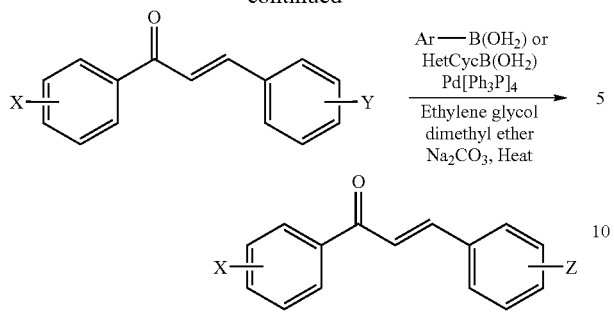

HetCyc: heterocyclic ring

Example 1:

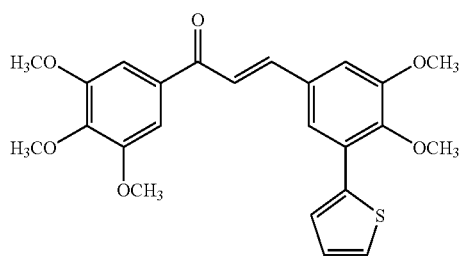

3-[3,4-dimethoxy-5-(thien-2-yl)phenyl]-1-(3,4,5-trimethoxyphenyl)-2-propen-1-one Ex-1A: 3',4',5'-Trimethoxyacetophenone (1.47 g, 6.9 mmol) and 3-bromo-4,5-dimethoxybenzaldehyde (1.64 g, 0.67 mmol) were suspended in ethanol (50 mL). Sodium hydroxide solution (50%, 1 mL) was added dropwise. The mixture was stirred at room temperature for 2 h. Water (20 mL) was added. The precipitate was filtered out, washed with water and dried over an oil pump to give 1.91 g (65%) of the desired product, 3-(3-bromo-4,5-dimethoxyphenyl)-1-(3,4,5-trimethoxyphenyl)-2-propen-1-one, as a slightly yellow residue.

3-(3-Bromo-4,5-dimethoxyphenyl)-1-(3,4,5-trimethoxyphenyl)-2-propen-1-one (0.105 g, 0.2 mmol) from Ex-1A was dissolved in ethylene glycol dimethyl ether (20 mL). Tetrakis(triphenylphosphine)palladium(0) (0.116 g, 0.1 mmol) was added, and the mixture was stirred at room temperature under nitrogen for 5 min. 2-Thiopheneboronic acid (0.128 g) and sodium carbonate solution (2 M, 0.5 mL) were added. The mixture was stirred at reflux under nitrogen overnight. Upon cooling to room temperature it was poured into water (100 mL) and extracted with dichloromethane (100 mL). The organic phase was dried over sodium sulfate and evaporated. Silica gel chromatography (hexane/ethyl acetate, 4:1, 2:1) gave 0.079 g (90%) of the desired 3-[3,4-dimethoxy-5-(thien-2-yl)phenyl]-1-(3,4,5-trimethoxyphenyl)-2-propen-1-one product as a slightly yellow residue. 1H-NMR (300 MHz, CDCl3): 7.79 (d, 1H), 7.56 (m, 2H), 7.42 (d, 1H), 7.39 (d, 1H), 7.29 (s, 2H), 7.10–7.16 (m, 2H), 3.89–4.00 (m, 15H). Anal. Calculated for C24H24O6S C: 65.44, H: 5.49, S: 7.28; found C: 65.69, H: 5.59, S: 6.99.

Additional substituted 1-phenyl-3-[(heteroaryl)phenyl]-2-propen-1-ones can be prepared by one skilled in the art using similar methods, as shown in Example Table 1.

Example Table 1. Substituted 1-Phenyl-3-[(Heteroaryl)phenyl]-2-propen-1-ones.

| Ex. No. | X | Z | Melting point (° C.) |
|---|---|---|---|
| 2 | 2,3,4-trimethoxy | 3,4-dimethoxy-5-(thien-2-yl) | 94–97 |
| 3 | 3,4,5-trimethoxy | 5-(5-acetylthien-2-yl)-3,4-dimethoxy | 109–112 |
| 4 | 3,4,5-trimethoxy | 5-(benzo[b]thien-2-yl)-3,4-dimethoxy | 150–151 |
| 5 | 3,4,5-trimethoxy | 2,4-dimethoxy-5-(thien-2-yl) | 75–80 |

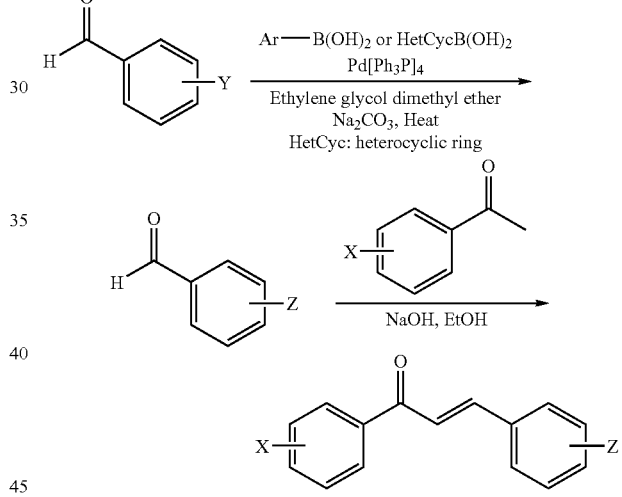

Scheme 2

Example 6:

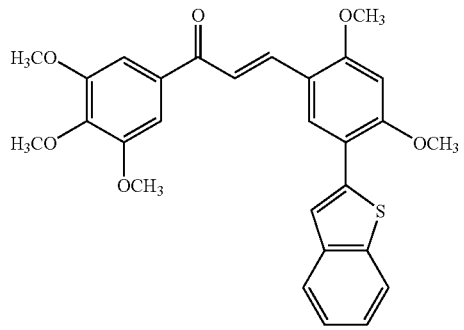

3-[5-(benzo[b]thien-2-yl)-2,4-dimethoxyphenyl]-1-(3,4,5-trimethoxyphenyl)-2-propen-1-one Ex-6A: 5-Bromo-2,4-dimethoxybenzaldehyde (4.9 g, 20.0 mmol) was dissolved in ethylene glycol dimethyl ether (50 mL). Tetrakis(triphenylphosphine)palladium(0) (2.32 g, 2 mmol) was added, and the mixture was stirred at room temperature under nitrogen for 5 min. Benzo[b]thiophene-2-boronic acid (4.27 g, 24 mmol) and sodium carbonate solution (2 M, 20 mL) were added. The mixture was stirred at reflux under nitrogen for 24 hours. Upon cooling to room temperature, it was poured into water and extracted with ethyl acetate. The organic phase was dried over sodium sulfate and evaporated. Silica gel chromatography (hexane/ethyl acetate 2:1 then 1:1) gave 4.75 g (83%) of the desired 5-(benzo[b]thien-2-yl)-2,4-dimethoxybenzaldehyde.

3',4',5'-Trimethoxyacetophenone (1.62 g, 7.7 mmol) was dissolved in ethanol (50 mL). Sodium hydroxide solution (50%, 4 mL) was added and the mixture was stirred at room temperature for 30 minutes. 5-(Benzo[b]thien-2-yl)-2,4-dimethoxybenzaldehyde (2.2 g, 7.7 mmol) from Ex-6A was added, and the mixture was stirred at room temperature overnight. The resulting yellow precipitate was filtered out, rinsed with water and dried over an oil pump to give 3.4 g (92%) of the desired 3-[5-(benzo[b]thien-2-yl)-2,4-dimethoxyphenyl]-1-(3,4,5-trimethoxyphenyl)-2-propen-1-one product as a solid, m.p. 194–196° C. 1H-NMR (300 MHz, CDCl3): 8.09 (d, 1H), 7.93 (s, 1H), 7.83 (d, 1H), 7.78 (d, 1H), 7.67 (s, 1H), 7.52 (d, 1H), 7.25–7.38 (m, 4H), 6.57 (s, 1H), 3.9–4.1 (m, 15H). Anal. Calculated for C28H26O6S: C, 68.55, H, 5.34, S, 6.53; found C: 68.48, H: 5.43, S: 6.52.

Additional substituted 1-[(heteroaryl)phenyl]-3-phenyl-2-propen-1-ones and substituted 3-[(heteroaryl)phenyl]-1-phenyl-2-propen-1-ones can be prepared by one skilled in the art using similar methods, as shown in Example Tables 2a and 2b.

Example Table 2a. Substituted 1-[(Heteroaryl)phenyl]-3-phenyl-2-propen-1-ones and Substituted 3-[(Heteroaryl)phenyl]-1-phenyl-2-propen-1-ones.

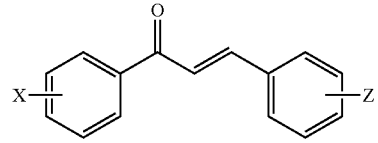

| Example No. | X | Z | Melting point (° C.) |
|---|---|---|---|
| 7 | 3,4,5-trimethoxy | 2-methoxy-5-(thien-2-yl) | 47–53 |
| 8 | 2,4,6-trimethoxy | 2-methoxy-5-(thien-2-yl) | 173–180 |
| 9 | 3,4-dimethoxy | 2-methoxy-5-(thien-2-yl) | 124–127 |
| 10 | 2,6-dimethoxy | 2-methoxy-5-(thien-2-yl) | 171–173 |
| 11 | 4-methoxy | 2-methoxy-5-(thien-2-yl) | 65–85 |
| 12 | 3,4,5-trimethoxy | 4-(thien-2-yl) | 135–140 |
| 13 | 3,4-dimethoxy | 4-(thien-2-yl) | 170–180 |
| 14 | 3,5-dimethoxy | 2-methoxy-5-(thien-2-yl) | 135–140 |
| 15 | 2,5-dimethoxy | 2-methoxy-5-(thien-2-yl) | 96–100 |
| 16 | 3,4,5-trimethoxy | 3,4-dimethoxy-5-(3-pyridyl) | Oil |
| 17 | 2,5-dimethoxy-4-(thien-2-yl-methoxy) | 2-methoxy-5-(thien-2-yl) | 54–73 |
| 18 | 4-iodo-2-methoxy | 2-methoxy-5-(thien-2-yl) | 150–155 |
| 19 | 3-methoxy-4-(2-pyridylmethoxy) | 2-methoxy-5-(thien-2-yl) | 92–94 |
| 20 | 3,4-dimethoxy | 5-(benzo[b]thien-2-yl)-2,4-dimethoxy | 159–161 |
| 21 | 2-methoxy-4-(3-methoxyphenyl) | 2-methoxy-5-(thien-2-yl) | 97–107 |
| 22 | 3,4-methylenedioxy | 2-methoxy-5-(thien-2-yl) | 140–145 |
| 23 | 4-(4-ethyloxy-carbonylbenzyloxy)-3-methoxy | 2-methoxy-5-(thien-2-yl) | 62–65 |
| 24 | 4-(4-tert-butyloxy-carbonylaminobenzyloxy)-3-methoxy | 2-methoxy-5-(thien-2-yl) | 50–60 |
| 25 | 4-(4-aminobenzyl-oxy)-3-methoxy | 2-methoxy-5-(thien-2-yl) | 67–80 |
| 26 | 3-methoxy-4-(3-pyridylmethoxy) | 2-methoxy-5-(thien-2-yl) | 220–255 |
| 27 | 3-methoxy-4-(4-pyridylmethoxy) | 2-methoxy-5-(thien-2-yl) | 165–170 |
| 28 | 3,4,5-trimethoxy | 2-methoxy-5-(5-methylthien-2-yl) | 111–115 |
| 29 | 3,4-dimethoxy | 2-methoxy-5-(5-methylthien-2-yl) | 119–124 |
| 30 | 3,4-methylenedioxy | 2-methoxy-5-(5-methylthien-2-yl) | 115–117 |
| 31 | 3,4,5-trimethoxy | 2-methoxy-5-(4-methylthien-2-yl) | 103–105 |

Example Table 2a. Substituted 1-[(Heteroaryl)phenyl]-3-phenyl-2-propen-1-ones and Substituted 3-[(Heteroaryl)phenyl]-1-phenyl-2-propen-1-ones.

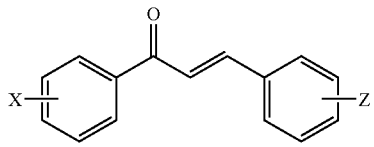

| Example No. | X | Z | Melting point (° C.) |
|---|---|---|---|
| 32 | 3,4-dimethoxy | 2-methoxy-5-(4-methylthien-2-yl) | 82–90 |
| 33 | 3,4-methylenedioxy | 2-methoxy-5-(4-methylthien-2-yl) | 143–146 |
| 34 | 4-(4-carboxy-benzyloxy-3-methoxy | 2-methoxy-5-(thien-2-yl) | Oil |
| 35 | 3,4-difluoro | 2-methoxy-5-(thien-2-yl) | 100–105 |
| 36 | 3,4-dichloro-2-hydroxy | 2-methoxy-5-(thien-2-yl) | 152–163 |
| 37 | 3,4,5-trimethoxy | 5-(benzo[b]thien-2-yl)-2-methoxy | 150–151 |
| 38 | 3,4-dimethoxy | 5-(benzo[b]thien-2-yl)-2-methoxy | 155–162 |
| 39 | 4-methoxy | 5-(benzo[b]thien-2-yl)-2-methoxy | 173–176 |
| 40 | 2-methoxy-5-(thien-2-yl) | 4-ethoxy-3-fluoro | Oil |
| 41 | 2,3,4-trimethoxy | 2,4-dimethoxy-5-(thien-2-yl) | 132–133 |
| 42 | 3,4-dichloro-2-hydroxy | 5-(benzo[b]thien-2-yl)-2-methoxy | 203–210 |
| 43 | 3,5-dimethoxy-4-(2-morpholino-ethyloxy) | 5-(benzo[b]thien-2-yl)-2,4-dimethoxy | 111–113 |
| 44 | 4-carboxymethoxy-3,5-dimethoxy | 5-(benzo[b]thien-2-yl)-2,4-dimethoxy | 145–153 |
| 45 | 2,3,4-trimethoxy | 5-(benzo[b]thien-2-yl)-2,4-dimethoxy | 145–147 |
| 46 | 2,3,4-trimethoxy | 5-(benzo[b]thien-2-yl)-2-carboxymethoxy-4-methoxy | 195–200 |
| 47 | 3,5-dimethoxy-4- | 5-(benzo[b]thien-2-yl)-2,4-dimethoxy | Oil |
| 48 | 4-(2,3-isopropylidene-dioxy-1-propoxy)-3,5-dimethoxy | 5-(benzo[b]thien-2-yl)-2,4-dimethoxy | 131–135 |
| 49 | 2,3,4-trimethoxy | 5-(benzo[b]thien-2-yl)-3,4-dimethoxy | 120–124 |
| 50 | 3-methoxy-4-(4-pyridylmethoxy), hydrogen chloride | 2-methoxy-5-(thien-2-yl) | 173–175 |
| 51 | 3-methoxy-4-(2-pyridylmethoxy), hydrogen chloride | 2-methoxy-5-(thien-2-yl) | 168–171 |
| 52 | 3,4-dichloro-2-hydroxy, sodium salt | 2-methoxy-5-(thien-2-yl) | >260 |

EXAMPLE TABLE 2b

Cyclic Substituted 1-[(Heteroaryl)phenyl]-3-phenyl-2-propen-1-ones and Substituted 3-[(Heteroaryl)phenyl]-1-phenyl-2-propen-1-ones.

| Example No. | Structure | m.p. (° C.) |
|---|---|---|
| 53 | 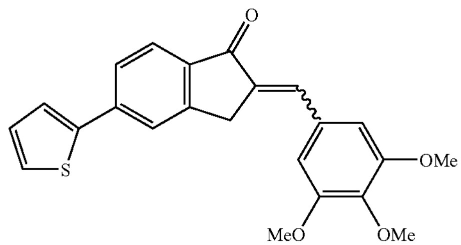 | 216–222 |
| 54 | 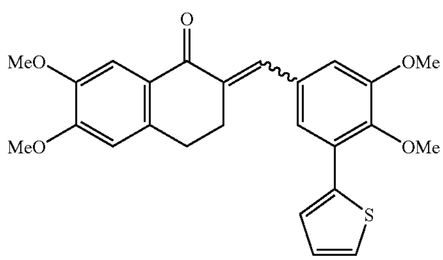 | 192–205 |
| 55 | 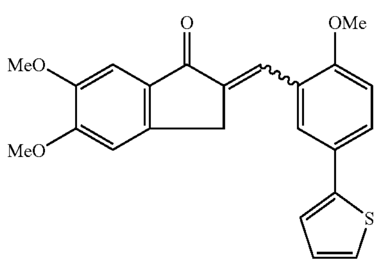 | 164–172 |

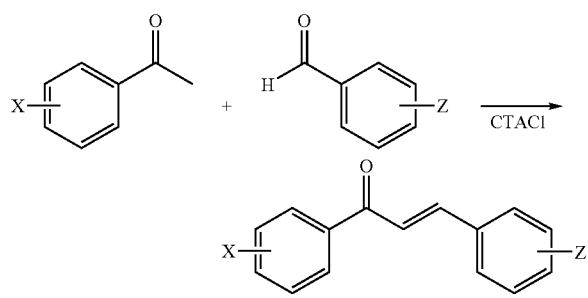

Scheme 3

Example 56:

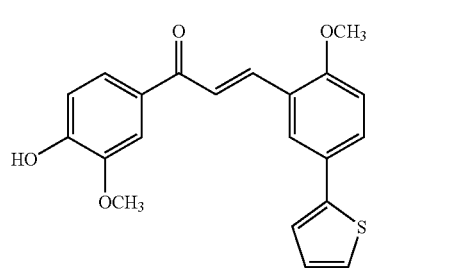

3-[2-methoxy-5-(thien-2-yl)phenyl]-1-(4-hydroxy-3-methoxyphenyl)-2-propen-1-one

To a suspension of 2-methoxy-5-(thien-2-yl)benzaldehyde (0.5 g, 2.3 mmol), obtained in the same manner as described in Ex-6A, in 5 N KOH solution was added cetyltrimethyl-ammonium chloride (CTACl, 25% in water, 4 mL, 3.0 mmol) followed by the addition of 4′-hydroxy-3′-methoxyacetophenone (0.38 g, 2.3 mmol). The mixture was stirred at room temperature overnight. Then it was acidified to about pH 1 with 6 M sulfuric acid, saturated with sodium chloride, and extracted with dichloromethane. The organic phase was washed with brine, dried and evaporated. Silica gel chromatography (hexane/ethyl acetate, 3:1 then 1:1) gave 0.61 g (73%) of a foam as the desired 3-[2-methoxy-5-(thien-2-yl)phenyl]-1-(4-hydroxy-3-methoxyphenyl)-2-propen-1-one product, m.p. 142–144° C. 1H-NMR (300 MHz, CDCl3): 8.21 (d, 1H), 7.82 (s, 1H), 7.55–7.75 (m, 4H), 6.85–7.15 (m, 4H), 6.14 (s, 1H), 4.00 (s, 3H), 3.95 (s, 3H).

Scheme 4

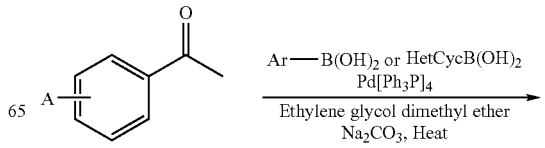

-continued

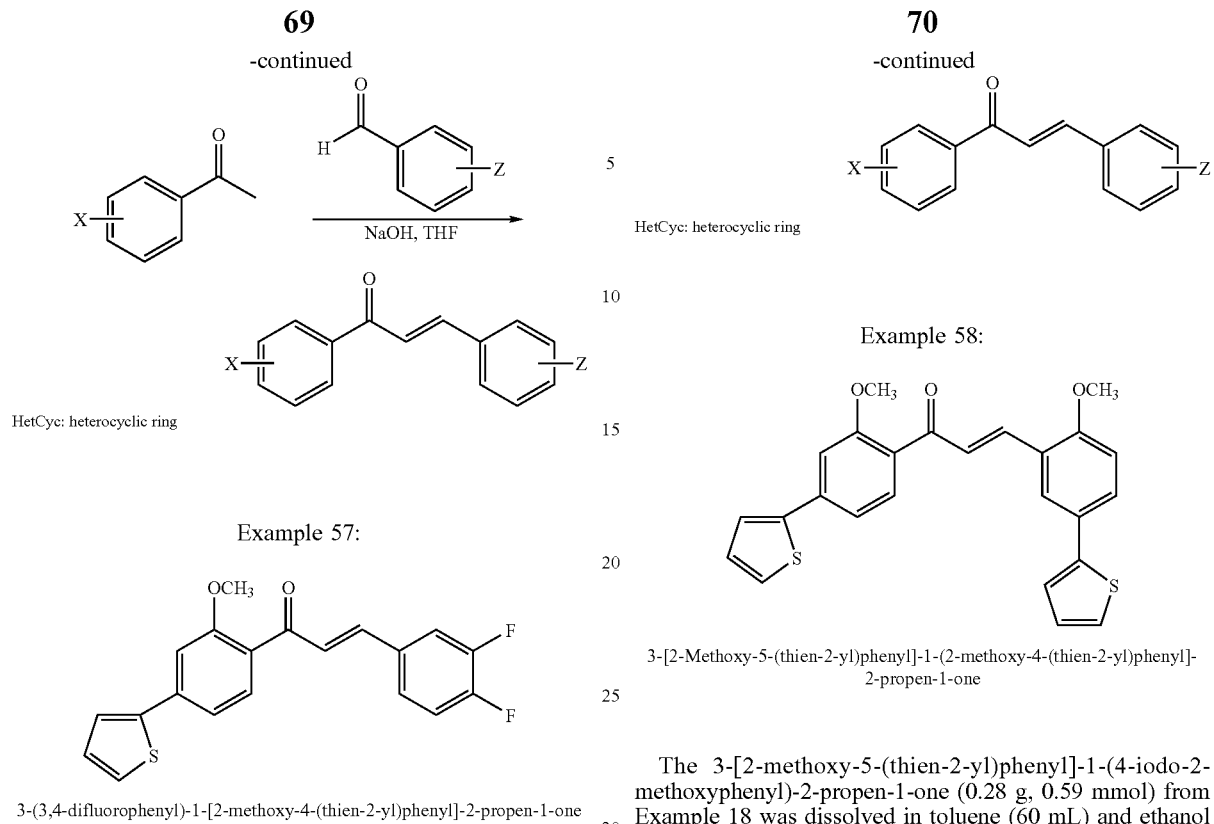

Example 57:

3-(3,4-difluorophenyl)-1-[2-methoxy-4-(thien-2-yl)phenyl]-2-propen-1-one

Ex-57a: 4'-iodo-2'-methoxyacetophenone (1.08 g, 3.9 mmol) in ethylene glycol dimethyl ether (50 ml) was degassed for 15 minutes. Tetrakis(triphenylphosphine) palladium(0) (0.456 g, 0.39 mmol), thiophene-2-boronic acid (0.75 g, 5.9 mmol), and sodium carbonate solution (2 m, 4 ml, 8 mmol) were added. The mixture was stirred at reflux under nitrogen for 24 hours. Upon cooling to room temperature, it was poured into water and extracted with dichloromethane. The organic phase was dried over sodium sulfate and evaporated. Silica gel chromatography (hexane/ ethyl acetate, 3:1) gave 0.88 g (98%) of the desired 2'-methoxy-4'-(thien-2-yl)acetophenone.

The 2'-methoxy-4'-(thien-2-yl)acetophenone (0.30 g, 1.3 mmol) from Ex-57A and 3,4-difluorobenzaldehyde 0.19 g, 1.3 mmol) were mixed in tetrahydrofuran (THF, 10 mL). Cesium carbonate (1.2 g, 3.9 mmol) was added, and the mixture was stirred at reflux overnight. Upon cooling to room temperature, the mixture was filtered, the filtrate was treated with 0.5 M HCl, and extracted with dichloromethane. The organic phase was dried and evaporated. Silica gel chromatography gave 0.32 g (69%) of the desired 3-(3,4-difluorophenyl)-1-[2-methoxy-4-(thien-2-yl) phenyl]-2-propen-1-one product, m.p. 73–79° C. 1H-NMR (300 MHz, CDCl3): 7.70 (d, 1H), 7.25–7.40 (m, 2H), 6.98–7.15 (m, 7H), 6.49 (d, 1H), 3.89 (s, 3H).

Example 58:

3-[2-Methoxy-5-(thien-2-yl)phenyl]-1-(2-methoxy-4-(thien-2-yl)phenyl]-2-propen-1-one The 3-[2-methoxy-5-(thien-2-yl)phenyl]-1-(4-iodo-2-methoxyphenyl)-2-propen-1-one (0.28 g, 0.59 mmol) from Example 18 was dissolved in toluene (60 mL) and ethanol (10 mL), and the solution was degassed for 10 minutes. Then tetrakis(triphenyl-phosphine)palladium(0) (0.07 g, 0.05 mmol) was added, and the mixture was stirred at room temperature under nitrogen for 5 min. 2-Thipheneboronic acid (0.11 g, 0.88 mmol) and sodium carbonate solution (2 M, 1.5 mL) were added. The mixture was stirred at reflux under nitrogen overnight. The solvent was evaporated. Silica gel chromatography (hexane/ethyl acetate 3:1) of the resulting residue gave 0.21 g (81%) of the desired 3-[2-methoxy-5-(thien-2-yl)phenyl]-1-[(2-methoxy-4-(thien-2-yl)phenyl]-2-propen-1-one product as a solid, m.p. 30–50° C. 1H-NMR (300 MHz, CDCl3): 7.80 (d, 1H), 7.70 (d, 1H), 7.55 (d, 1H), 7.46 (m, 2H), 7.25 (d, 1H), 7.18 (d, 1H), 6.95–7.08 (m, 6H), 6.80 (d, 1H), 6.76 (d, 1H), 3.96 (s, 3H), 3.85 (s, 3H).

Scheme 6

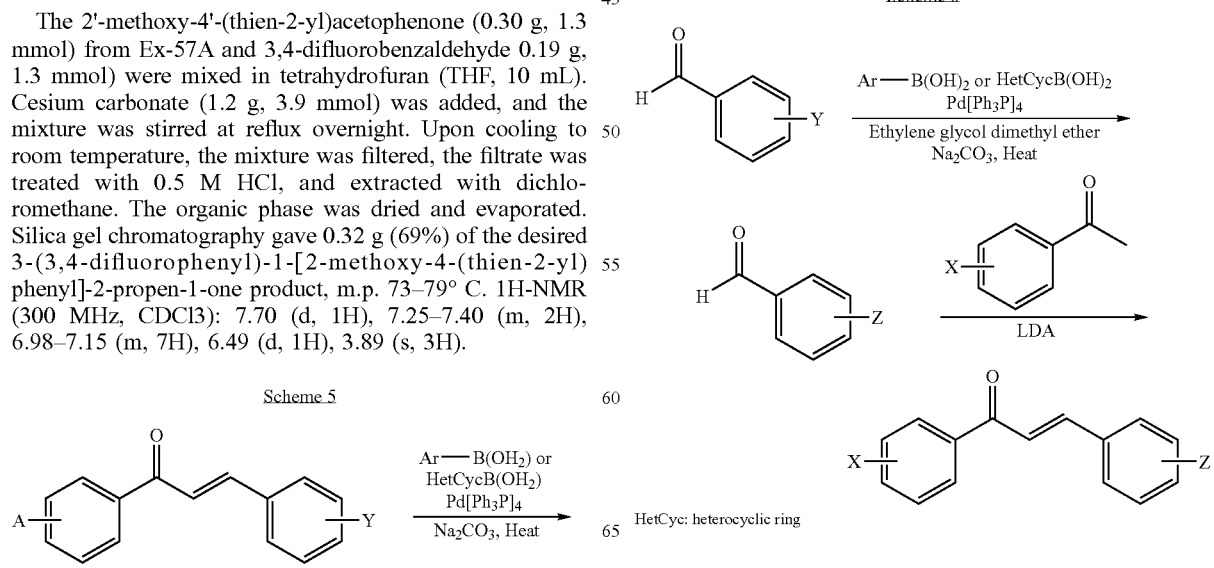

HetCyc: heterocyclic ring

Example 59:

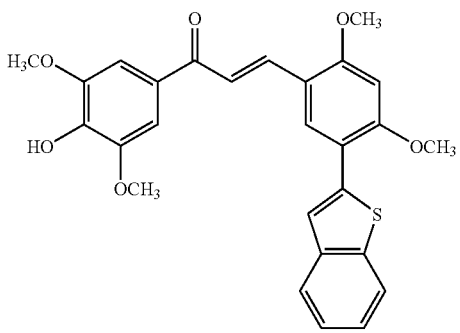

3-[5-(benzo[b]thien-2-yl)-2,4-dimethoxyphenyl]-1-(4-hydroxy-3,5-dimethoxyphenyl)-2-propen-1-one

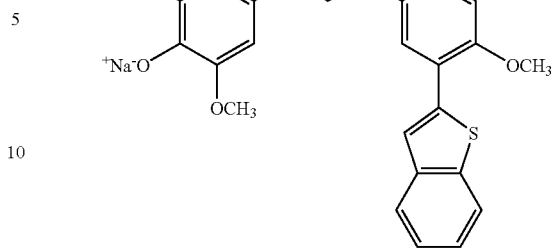

3-[5-(benzo[b]thien-2-yl)-2,4-dimethoxyphenyl]-1-(4-hydroxy-3,5-dimethoxyphenyl)-2-propen-1-one, sodium salt Ex-59A: To a solution of 4'-hydroxy-3',5'-dimethoxyacetophenone (1 g, 5.1 mmol) in N,N-dimethylformamide were added tert-butyldimethylsilyl chloride (1,15 g, 7.6 mmol) and imidazole (0.69 g, 10.2 mmol). The mixture was stirred at room temperature overnight. Upon quenching with 1 M sulfuric acid solution, the mixture was extracted with dichloromethane. The organic phase was washed with saturated sodium bicarbonate and brine. It was dried and evaporated. Water (2 mL) was added to the residue, and the precipitate was filtered out and dried over an oil pump to give 1.28 g (81%) of 3',5'-dimethoxy-4'-(tert-butyldimethylsiloxy)acetophenone as a white solid, m.p. 90–92° C.

Ex-59B: To a solution of 3',5'-dimethoxy-4'-(tert-butyldimethylsiloxy)acetophenone, from Ex-59A (0.5 g, 1.6 mmol) in tetrahydrofuran (10 mL) chilled with ice/water was added lithium diisopropylamide (2 M, 0.8 mL, 1.6 mmol). The mixture was stirred for 20 minutes while chilled. Then 5-(benzo[b]thien-2-yl)-2,4-dimethoxybenzaldehyde, from Ex-6A,(0.48 g, 1.6 mmol) in tetrahydrofuran (6 mL) was added, and the mixture was stirred at room temperature for 2 hours. Upon quenching with water, the mixture was extracted with dichloromethane. The organic phase was dried and evaporated. Crystallization from ethanol gave 0.19 g (20%) of the desired 3-[5-(benzo[b]thien-2-yl)2,4-dimethoxyphenyl]-1-(4-tert-butyldimethylsiloxy-3,5-dimethoxyphenyl)-2-propen-1-one as a yellow solid.

To a solution of 3-[5-(benzo[b]thien-2-yl)2,4-dimethoxyphenyl]-1-(4-tert-butyldimethyl-siloxy-3,5-dimethoxyphenyl)-2-propen-1-one, from Ex-59B, (0.135 g, 0.228 mmol) in tetrahydrofuran (2 mL) was added tetrabutylammonium fluoride (0.061 g. 0.228 mmol), and the mixture was stirred at room temperature for two hours. Upon quenching with water, the mixture was extracted with dichloromethane. The organic phase was dried and evaporated. Silica gel chromatography (hexane/ethyl acetate, 1:1) gave 0.05 g (46%) of the desired 3-[5-(benzo[b]thien-2-yl) 2,4-dimethoxyphenyl]-1-(4-hydroxy-3,5-dimethoxyphenyl)-2-propen-1-one product as a yellow solid, m.p. 85–105° C.

3-[5-(Benzo[b]thien-2-yl)2,4-dimethoxyphenyl]-1-(4-hydroxy-3,5-dimethoxyphenyl)-2-propen-1-one from Example 59 was treated with 5 N NaOH and the desired 3-[5-(Benzo[b]thien-2-yl)2,4-dimethoxyphenyl]-1-(4-hydroxy-3,5-dimethoxyphenyl)-2-propen-1-one sodium salt product precipitated out following the addition of dichloromethane, m.p. 209–215° C.

Example 61:

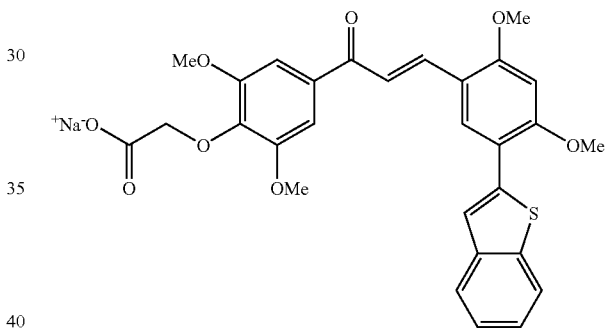

3-[5-(Benzo[b]thien-2-yl)-2,4-dimethoxyphenyl]-1-(4-carboxymethoxy-3,5-dimethoxyphenyl)-2-propen-1-one, sodium salt Ex-61A: 3',5'-Dimethoxy-4'-hydroxyacetophenone (6.03 g, 31 mmol) and triphenylphosphine (8.05 g, 31 mmol) were stirred in 124 mL of tetrahydrofuran (THF). The mixture was treated with ethyl glycolate (3.2 g, 31 mmol) and diethylazodicarboxylate (4.83 mL, 31 mmol). The reaction mixture was stirred under reflux for about 3.5 h and then evaporated. The residue was crystallized from hexane/ethyl acetate. The mother liquor was concentrated to give a crude product which was purified by recrystallization from EtOH twice to give 3.14 g of 4'-ethoxycarbonyl-methoxy-3',5'-dimethoxyacetophenone. Solvent removal from the mother liquor provided additional crude product which was purified by silica gel chromatography (hexane/ethyl acetate, 1:1) to give additional product (4.2 g). The total amount of pure material isolated was 7.34 g (90% yield). mp. 81–83° C.; Anal. Calcd. for Cl4H18O6: C, 59.57; H, 6.43; Found: C, 59.60; H, 6.34; MS (direct probe): Calcd for Cl4H18O6: m/z=282, found: m/z=282.

4'-Ethoxycarbonylmethoxy-3',5'-dimethoxyacetophenone from Ex-61A (3.15 g; 11.2 mmol) and 5-(benzo[b]thien-2-yl)-2,4-dimethoxybenzaldehyde from Ex-6A (3.33 g; 11.2 mmol) were suspended in 250 mL of absolute ethanol. The mixture was stirred and heated to give a clear solution then treated dropwise with 50% NaOH (4 mL). A yellow precipitate gradually formed after the addition of the base. The mixture was stirred under reflux for ca. 30 minutes and then cooled to room temperature and stirred for 5 hours. The yellow precipitate was isolated by filtration, washed with EtOH/H2O (1:1), acetone, and hexanes. Final solvent removal under reduced pressure gave 2.4 g (39%) of the desired 3-[5-(Benzo[b]thien-2-yl)-2,4-dimethoxyphenyl]-1-(4-carboxymethoxy-3,5-di-methoxyphenyl)-2-propen-1-one sodium salt product as a yellow solid, m.p. 191–196° C. (decomp.). 1H-NMR (300 MHz, DMSO-d6): 8.30 (s, 1H), 7.65–8.02 (m, 5 H), 7.31 (m, 4H), 6.85 (s, 1H), 4.11 (s, 2H), 4.02 (s, 3H), 4.00 (s, 6H), 3.84 (s, 6H). Anal. Calcd. for C29H25NaO8S.2.5 H2O: C, 57.90; H, 5.03; S, 5.33; Found: C, 57.53; H, 4.62; S, 5.34; MS (Neg. Ion ES): Calcd. for C29H25O8S: m/z=533, found: m/z=534.

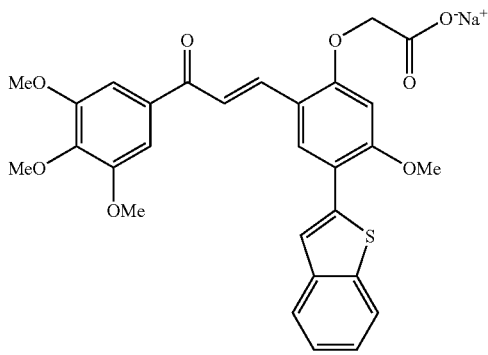

3-[5-(Benzo[b]thien-2-yl)-2-carboxymethoxy-4-methoxyphenyl]-1-(3,4,5-trimethoxyphenyl)-2-propen-1-one, sodium salt Ex-62A: A solution of 2-hydroxy-4-methoxybenzaldehyde (3.03 g, 20 mmol) in 25 mL of dichloromethane was cooled to 0° C. and treated dropwise with a solution of bromine (3.41 g, 21 mmol) in 10 mL of dichloromethane. The reaction mixture was stirred at 0° C. for 1.5 hours. The solvent was removed by rotary evaporation to give a residue. The residue was taken up in EtOAc and washed with 3 portions of water. The organic layer was dried over MgSO4. The drying agent was removed by filtration, and solvent was removed by rotary evaporation to give 3.9 g of the desired 5-bromo-2-hydroxy-4-methoxybenzaldehyde as a solid, m.p. 111–115° C.

Ex-62B: A stream of N2 was bubbled through a solution of 5-bromo-2-hydroxy-4-methoxybenzaldehyde (1 g, 4.3 mmol) from Ex-62A in 30 mL of ethylene glycol dimethyl ether for 15 min. Tetrakis-triphenylphosphine palladium (0) (0.5 g, 0.4 mmol) was added along with thiophene-2-boronic acid (1.2 g, 6.5 mmol) and 10 mL of Na2CO3 (2M aqueous solution). The resulting mixture was stirred under reflux overnight. The solvent was removed by rotary evaporation and the residue was treated with saturated NaHCO3 and extracted with dichloromethane. The organic phase was washed with brine, dried over MgSO4, and filtered to remove drying agent. Solvent was removed by rotary evaporation. Purification of the crude material by silica gel chromatography (hexanes/EtOAc, 2:1) gave 1.04 g of the desired 5-benzo[b]thien-2-yl-2-hydroxy-4-methoxybenzaldehyde.

Ex-62C: A solution of 5-benzo[b]thien-2-yl-2-hydroxy-4-methoxybenzaldehyde (1 g, 3.5 mmol) from Ex-62B and triphenylphosphine (1.0 g, 3.9 mmol) in 20 mL of THF was stirred and treated with ethyl glycolate (0.4 g, 3.9 mmol) and diethyl azodicarboxylate (0.7 mL, 3.9 mmol), The resulting mixture was stirred under reflux for 2 h. The solvent was removed by rotary evaporation and the residue was recrystallized from hexanes/EtOAc to give 0.34 g of product. The mother liquor was concentrated and purified by silica gel column chromatography (hexanes/EtOAc, 3:1)) to give an additional 0.07 g of product, providing a total of 0.4 g of the desired 5-(benzo[b]thien-2-yl)-2-ethoxycarbonylmethoxy-4-methoxybenzaldehyde.

A solution of 5-(benzo[b]thien-2-yl)-2-ethoxycarbonylmethoxy-4-methoxybenzaldehyde (0.49 g, 1.32 mmol) from Ex-62C in 100 mL of absolute EtOH was treated with 3',4',5'-trimethoxyacetophenone (0.31 g, 1.5 mmol) and 0.5 mL of NaOH (50% aqueous solution). The yellow solution was stirred overnight. The resulting yellow precipitate was filtered and washed with 50% EtOH in water, followed by acetone. Removal of residual solvent under vacuum gave 0.66 g of the desired,3-[5-(benzo[b]thien-2-yl)-2-carboxymethoxy-4-methoxyphenyl]-1-(3,4,5-trimethoxyphenyl)-2-propen-1-one sodium salt product, m.p. 255–257° C. 1H-NMR (300 MHz, DMSO-d6): 8.50 (d, 1H), 8.09 (s, 1H), 7.75–7.90 (m, 4H), 7.51 (s, 2H), 7.28 (m, 2H), 6.72 (s, 1H), 4.32 (s, 2H), 3.99 (s, 3H), 3.91 (s, 6H), 3.73 (s, 3H).

Anal. Calculated for C29H25NaO8S.2.5 H2O: C, 57.85, H, 4.97, S, 5.32; found C: 57.78, H: 4.74, S: 5.24. MS (Neg. Ion ES): Calcd. for C29H25O8S: m/z=533, found: m/z=534.

Using one or more of the preceding methods, additional substituted 1-[(heteroaryl or heterocyclic)phenyl]-3-phenyl-2-propen-1-ones and substituted 3-[(heteroaryl or heterocyclic)phenyl]-1-phenyl-2-propen-1-ones can be prepared by one skilled in the art using similar methods, as shown in Example Table 3 through 29.

Example Table 3. Substituted 3-[5-(benzo[b]thien-2-yl)-2-carboxymethoxy-4-methoxyphenyl]-1-phenyl-2-propen-1-ones.

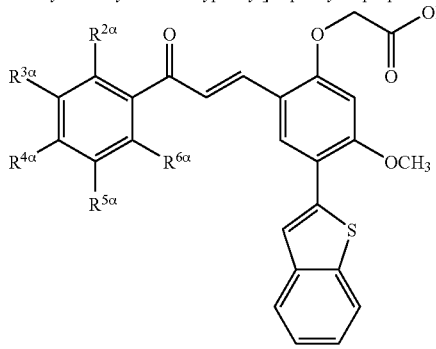

| EXAMPLE NUMBER | R2α | R3α | R4α | R5α | R6α |
|---|---|---|---|---|---|
| 63 | H | OMe | OCH2-cyclopropyl | OMe | H |
| 64 | OMe | H | H | H | H |
| 65 | H | OMe | H | H | H |
| 66 | H | H | F | H | H |
| 67 | F | H | H | H | H |
| 68 | H | F | H | H | H |
| 69 | F | F | F | F | F |
| 70 | F | H | F | H | H |
| 71 | H | F | F | H | H |
| 72 | H | F | H | F | H |
| 73 | H | OMe | OCF3 | OMe | H |
| 74 | F | H | OMe | H | H |

-continued

Example Table 3. Substituted 3-[5-(benzo[b]thien-2-yl)-2-carboxymethoxy-4-methoxyphenyl]-1-phenyl-2-propen-1-ones.

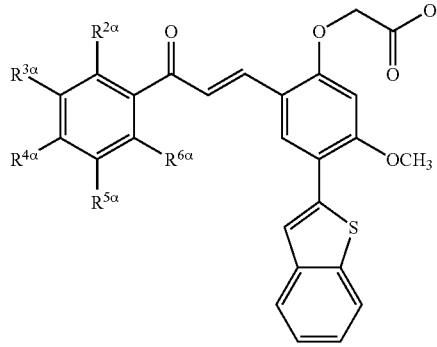

| EXAMPLE NUMBER | R2α | R3α | R4α | R5α | R6α |
|---|---|---|---|---|---|
| 75 | H | F | OMe | H | H |
| 76 | OH | H | F | H | H |
| 77 | OH | H | H | F | H |
| 78 | OMe | H | F | H | H |
| 79 | OMe | H | H | F | H |
| 80 | OMe | H | CH3 | H | H |
| 81 | OMe | H | H | CH3 | H |
| 82 | OMe | CH3 | H | H | H |
| 83 | OMe | H | H | H | CH3 |
| 84 | H | OMe | F | OMe | H |
| 85 | H | OMe | Cl | OMe | H |
| 86 | H | OMe | COOH | OMe | H |
| 87 | H | OMe | OCH2COOH | OMe | H |
| 88 | H | OMe | CH2COOH | OMe | H |
| 89 | H | OMe | SCH2COOH | OMe | H |
| 90 | H | OMe | SO3H | OMe | H |
| 91 | H | OMe | SO2NH2 | OMe | H |
| 92 | H | OMe | SO2N(Me)2 | OMe | H |
| 93 | H | OMe | OCH2CH(NH2)COOH | OMe | H |
| 94 | H | OMe | NH2 | OMe | H |
| 95 | H | OMe | N(CH3)2 | OMe | H |
| 96 | H | OMe | N(H)CH2COOH | OMe | H |
| 97 | H | OMe | pyrrolidin-1-yl | OMe | H |
| 98 | H | OMe | piperidin-1-yl | OMe | H |
| 99 | H | OMe | piperazin-1-yl | OMe | H |
| 100 | H | OMe | 4-methylpiperazin-1-yl | OMe | H |
| 101 | H | OMe | CH3 | OMe | H |
| 102 | H | OMe | CF3 | OMe | H |
| 103 | H | H | H | H | H |

Example Table 4. Substituted 3-[5-(benzo[b]thien-2-yl)-2,4-dimethoxyphenyl]-1-phenyl-2-propen-1-ones

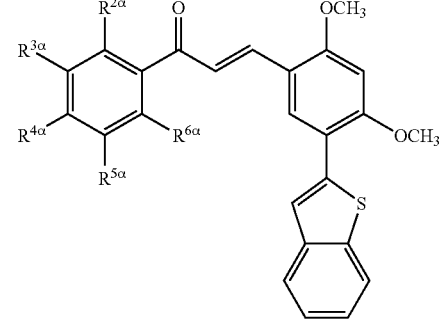

| EXAMPLE NUMBER | R2α | R3α | R4α | R5α | R6α |
|---|---|---|---|---|---|
| 104 | H | OMe | OCH2-cyclopropyl | OMe | H |
| 105 | OMe | H | H | H | H |
| 106 | H | OMe | H | H | H |
| 107 | H | H | F | H | H |
| 108 | F | H | H | H | H |
| 109 | H | F | H | H | H |
| 110 | F | F | F | F | F |
| 111 | F | H | F | H | H |
| 112 | H | F | F | H | H |
| 113 | H | F | H | F | H |
| 114 | H | OMe | OCF3 | OMe | H |
| 115 | F | H | OMe | H | H |
| 116 | H | H | OMe | H | H |
| 117 | OH | H | F | H | H |
| 118 | OH | H | H | F | H |
| 119 | OMe | H | F | H | H |
| 120 | OMe | H | H | F | H |
| 121 | OMe | H | CH3 | H | H |
| 122 | OMe | H | H | CH3 | H |
| 123 | OMe | CH3 | H | H | H |
| 124 | OMe | H | H | H | CH3 |
| 125 | H | OMe | F | OMe | H |
| 126 | H | OMe | Cl | OMe | H |
| 127 | H | OMe | COOH | OMe | H |
| 128 | H | OMe | CH2COOH | OMe | H |
| 129 | H | OMe | SCH2COOH | OMe | H |
| 130 | H | OMe | SO3H | OMe | H |
| 131 | H | OMe | SO2NH2 | OMe | H |
| 132 | H | OMe | SO2N(Me)2 | OMe | H |
| 133 | H | OMe | OCH2CH(NH2)COOH | OMe | H |
| 134 | H | OMe | NH2 | OMe | H |
| 135 | H | OMe | N(CH3)2 | OMe | H |
| 136 | H | OMe | N(H)CH2COOH | OMe | H |
| 137 | H | OMe | pyrrolidin-1-yl | OMe | H |
| 138 | H | OMe | piperidin-1-yl | OMe | H |
| 139 | H | OMe | piperazin-1-yl | OMe | H |

Example Table 4. Substituted 3-[5-(benzo[b]thien-2-yl)-2,4-dimethoxyphenyl]-1-phenyl-2-propen-1-ones

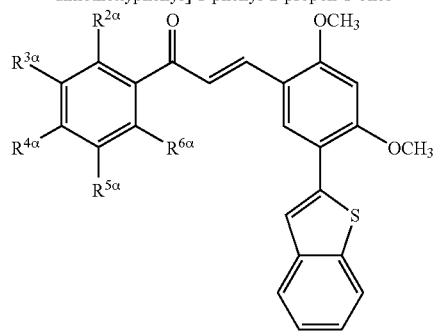

| EXAMPLE NUMBER | R2α | R3α | R4α | R5α | R6α |
|---|---|---|---|---|---|
| 140 | H | OMe | 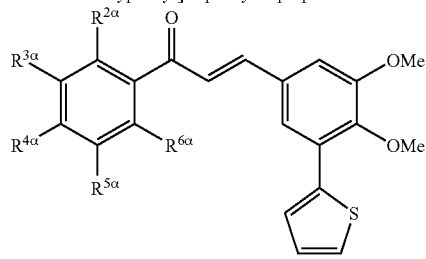 | OMe | H |
| 141 | H | OMe | CH3 | OMe | H |
| 142 | H | OMe | CF3 | OMe | H |
| 143 | H | H | H | H | H |

Example Table 5. Substituted 3-[5-(thien-2-yl)-3,4-dimethoxyphenyl]-1-phenyl-2-propen-1-ones.

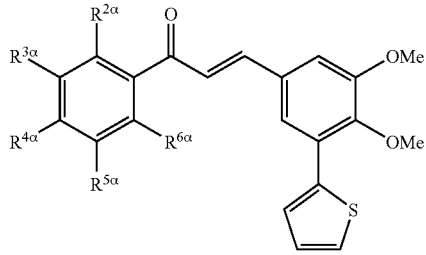

| EXAMPLE NUMBER | R2α | R3α | R4α | R5α | R6α |
|---|---|---|---|---|---|
| 144 | H | H | H | H | H |
| 145 | OMe | H | H | H | H |
| 146 | H | OMe | H | H | H |
| 147 | H | H | F | H | H |
| 148 | F | H | H | H | H |
| 149 | H | F | H | H | H |
| 150 | F | F | F | F | F |
| 151 | F | H | F | H | H |
| 152 | H | F | F | H | H |
| 153 | H | F | H | F | H |
| 154 | H | OMe | OCF3 | OMe | H |
| 155 | F | H | OMe | H | H |
| 156 | H | F | OMe | H | H |
| 157 | OH | H | F | H | H |
| 158 | OH | H | H | F | H |
| 159 | OMe | H | F | H | H |
| 160 | OMe | H | H | F | H |
| 161 | OMe | H | CH3 | H | H |
| 162 | OMe | H | H | CH3 | H |
| 163 | OMe | CH3 | H | H | H |
| 164 | OMe | H | H | H | CH3 |
| 165 | H | OMe | F | OMe | H |
| 166 | H | OMe | Cl | OMe | H |
| 167 | H | OMe | COOH | OMe | H |
| 168 | H | OMe | OCH2COOH | OMe | H |
| 169 | H | OMe | CH2COOH | OMe | H |
| 170 | H | OMe | SCH2COOH | OMe | H |
| 171 | H | OMe | SO3H | OMe | H |
| 172 | H | OMe | SO2NH2 | OMe | H |
| 173 | H | OMe | SO2N(Me)2 | OMe | H |
| 174 | H | OMe | OCH2CH(NH2)COOH | OMe | H |
| 175 | H | OMe | NH2 | OMe | H |
| 176 | H | OMe | N(CH3)2 | OMe | H |
| 177 | H | OMe | N(H)CH2COOH | OMe | H |
| 178 | H | OMe | pyrrolidinyl | OMe | H |
| 179 | H | OMe | piperidinyl | OMe | H |
| 180 | H | OMe | piperazinyl (HN) | OMe | H |
| 181 | H | OMe | 4-methylpiperazinyl | OMe | H |
| 182 | H | OMe | CH3 | OMe | H |
| 183 | H | OMe | CF3 | OMe | H |

Example Table 6. Substituted 3-[5-(heteroaryl or heterocyclic)-2,4-dimethoxyphenyl]-1-[(3,5-dimethoxy)-4-carboxymethoxyphenyl]-2-propen-1-ones.

-continued

Example Table 6. Substituted 3-[5-(heteroaryl or heterocyclic)-2,4-dimethoxyphenyl]-
1-[(3,5-dimethoxy)-4-carboxymethoxyphenyl]-2-propen-1-ones.

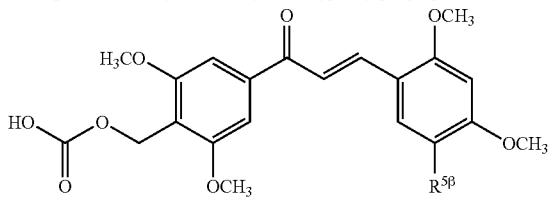

| Ex. No. | R5β | Ex. No. | R5β | Ex. No. | R5β |
|---|---|---|---|---|---|
| 203 | tetrahydrofuran-3-yl | 208 | pyridin-3-yl | 213 | piperidin-3-yl |
| 204 | tetrahydrofuran-2-yl | 209 | pyridin-2-yl | 214 | piperidin-2-yl |
| 205 | pyrimidin-5-yl | 210 | pyridin-4-yl | 215 | piperidin-4-yl |

Example Table 7. 3-[5-(Heteroaryl or Heterocyclic)-2-carboxymethoxy-4-
methoxyphenyl]-1-[3,4,5-trimethoxy)phenyl]-2-propen-1-ones.

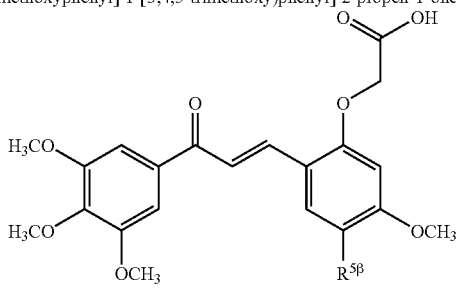

| Ex. No. | R5β | Ex. No. | R5β | Ex. No. | R5β |
|---|---|---|---|---|---|
| 216 | furan-2-yl | 227 | thiophen-2-yl | 238 | pyrrol-2-yl |
| 217 | furan-3-yl | 228 | thiophen-3-yl | 239 | pyrrol-3-yl |

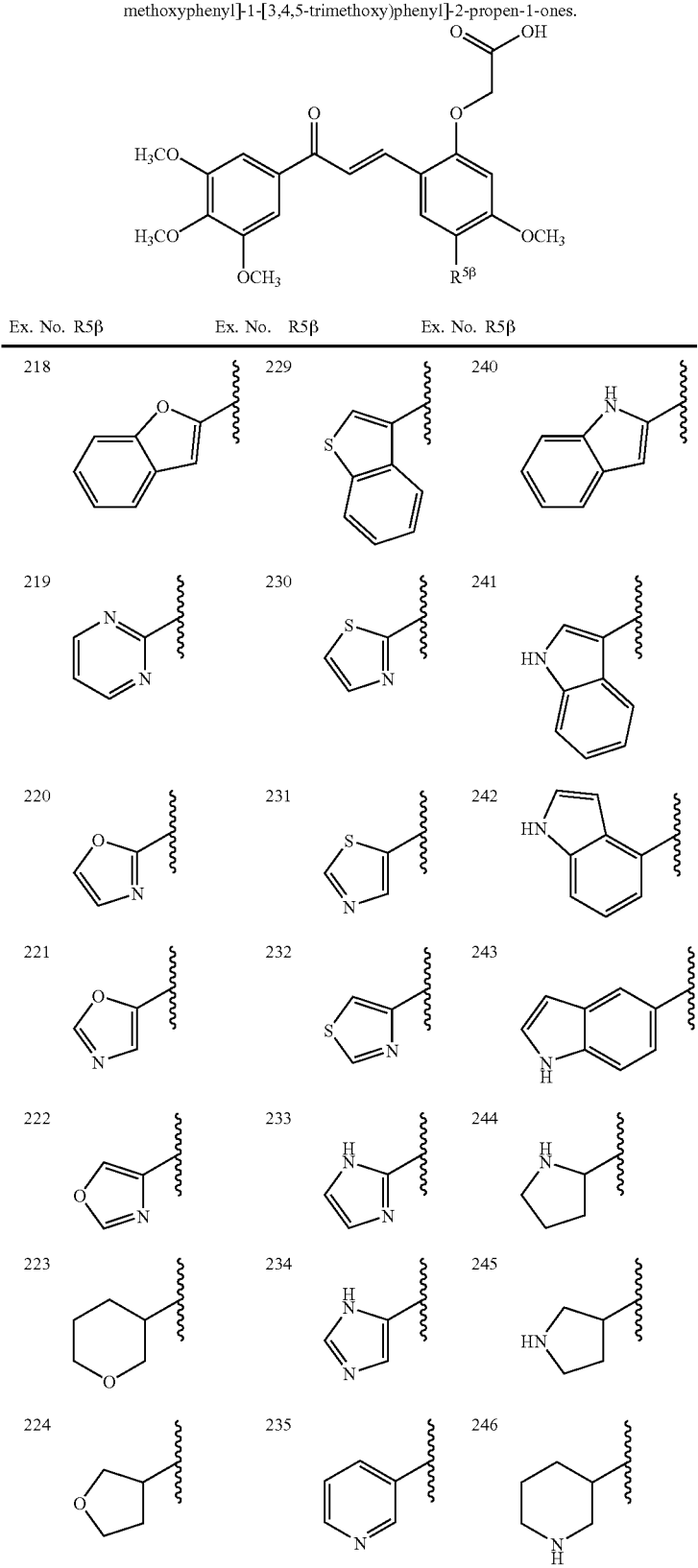

Example Table 7. 3-[5-(Heteroaryl or Heterocyclic)-2-carboxymethoxy-4-methoxyphenyl]-1-[3,4,5-trimethoxy)phenyl]-2-propen-1-ones.

| Ex. No. | R5β | Ex. No. | R5β | Ex. No. | R5β |
|---|---|---|---|---|---|
| 225 | tetrahydrofuran-2-yl | 236 | pyridin-2-yl | 247 | piperidin-2-yl |
| 226 | pyrimidin-5-yl | 237 | pyridin-4-yl | 248 | piperidin-4-yl |

Example Table 8. 3-[5-(Heteroaryl or Heterocyclic)-2,4-dimethoxyphenyl]-1-[(3,4,5-trimethoxy)phenyl]-2-propen-1-ones.

| Ex. No. | R5β | Ex. No. | R5β | Ex. No. | R5β |
|---|---|---|---|---|---|
| 249 | furan-2-yl | 252 | thiophen-2-yl | 255 | pyrrol-2-yl |
| 250 | furan-3-yl | 253 | thiophen-3-yl | 256 | pyrrol-3-yl |
| 251 | benzofuran-2-yl | 254 | benzothiophen-3-yl | 257 | indol-2-yl |

-continued

Example Table 8. 3-[5-(Heteroaryl or Heterocyclic)-2,4-dimethoxyphenyl]-1-[(3,4,5-trimethoxy)phenyl]-2-propen-1-ones.

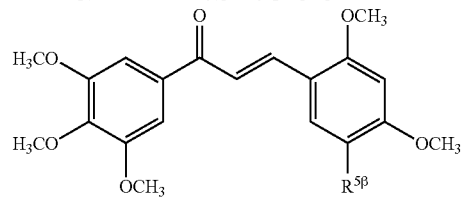

| Ex. No. | R5β | Ex. No. | R5β | Ex. No. | R5β |
|---|---|---|---|---|---|
| 258 | pyrimidin-2-yl | 266 | thiazol-2-yl | 274 | 1H-indol-3-yl |
| 259 | oxazol-2-yl | 267 | thiazol-5-yl | 275 | 1H-indol-4-yl |
| 260 | oxazol-5-yl | 268 | thiazol-4-yl | 276 | 1H-indol-5-yl |
| 261 | oxazol-4-yl | 269 | 1H-imidazol-2-yl | 277 | pyrrolidin-2-yl |
| 262 | tetrahydropyran-3-yl | 270 | 1H-imidazol-5-yl | 278 | pyrrolidin-3-yl |
| 263 | tetrahydrofuran-3-yl | 271 | pyridin-3-yl | 279 | piperidin-3-yl |
| 264 | tetrahydrofuran-2-yl | 272 | pyridin-2-yl | 280 | piperidin-2-yl |

-continued

Example Table 8. 3-[5-(Heteroaryl or Heterocyclic)-2,4-dimethoxyphenyl]-1-[(3,4,5-trimethoxy)phenyl]-2-propen-1-ones.

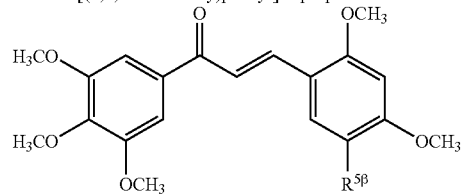

| Ex. No. | R5β | Ex. No. | R5β | Ex. No. | R5β |
|---|---|---|---|---|---|
| 265 | pyrimidin-5-yl | 273 | pyridin-4-yl | 281 | piperidin-4-yl |

Example Table 9. 3-[5-(Heteroaryl or Heterocyclic)-3,4-dimethoxyphenyl]-1-[(3,4,5-trimethoxy)phenyl]-2-propen-1-ones.

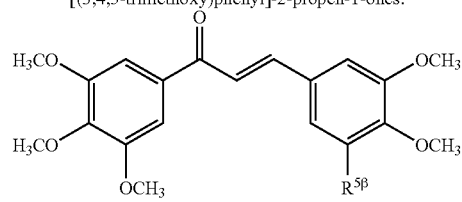

| Ex. No. | R5β | Ex. No. | R5β | Ex. No. | R5β |
|---|---|---|---|---|---|
| 675 | furan-2-yl | 301 | thiophen-2-yl | 312 | pyrrol-2-yl |
| 282 | furan-3-yl | 302 | thiophen-3-yl | 313 | pyrrol-3-yl |
| 283 | benzofuran-2-yl | 303 | benzothiophen-3-yl | 314 | indol-2-yl |
| 284 | pyrimidin-2-yl | 304 | thiazol-2-yl | 315 | indol-3-yl |

-continued

Example Table 9. 3-[5-(Heteroaryl or Heterocyclic)-3,4-dimethoxyphenyl]-1-[(3,4,5-trimethoxy)phenyl]-2-propen-1-ones.

| Ex. No. | R5β | Ex. No. | R5β | Ex. No. | R5β |
|---|---|---|---|---|---|
| 285 | oxazol-2-yl | 305 | thiazol-5-yl | 316 | 1H-indol-4-yl |
| 286 | oxazol-5-yl | 306 | thiazol-4-yl | 317 | 1H-indol-5-yl |
| 287 | oxazol-4-yl | 307 | 1H-imidazol-2-yl | 318 | pyrrolidin-2-yl |
| 288 | tetrahydropyran-3-yl | 308 | 1H-imidazol-4-yl | 319 | pyrrolidin-3-yl |
| 676 | tetrahydrofuran-3-yl | 309 | pyridin-3-yl | 320 | piperidin-3-yl |
| 289 | tetrahydrofuran-2-yl | 310 | pyridin-2-yl | 321 | piperidin-2-yl |
| 300 | pyrimidin-5-yl | 311 | pyridin-4-yl | 322 | piperidin-4-yl |

Example Table 10. Substituted 3-[5-(benzo[b]thien-2-yl)-4-methoxyphenyl]-1-[(3,5-dimethoxy)phenyl]-2-buten-1-ones.

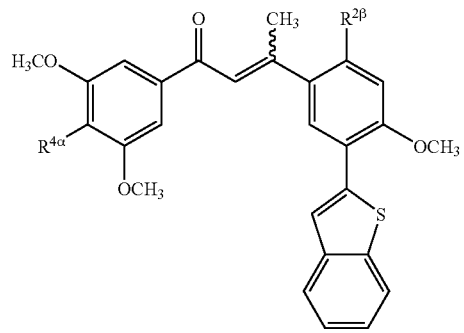

| Example No | R4α | R2β |
|---|---|---|
| 323 | OMe | OMe |
| 324 | OCH2COOH | OMe |
| 325 | OMe | OCH2COOH |

Example Table 11. 1-[4-(Heteroaryl or Heterocyclic)-phenyl]-3-[(2-carboxymethoxy-4-methoxy)phenyl]-2-propen-1-ones.

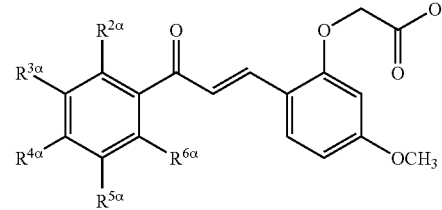

| EXAMPLE NO. | R2α | R3α | R4α | R5α | R6α |
|---|---|---|---|---|---|
| 326 | H | H | 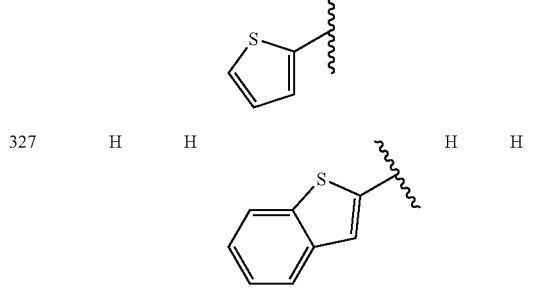 | H | H |
| 327 | H | H | 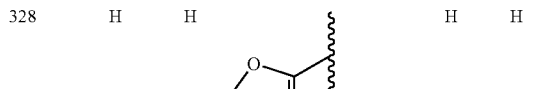 | H | H |
| 328 | H | H | 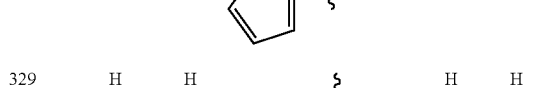 | H | H |
| 329 | H | H | 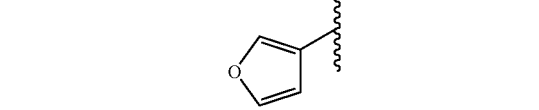 | H | H |

Example Table 11. 1-[4-(Heteroaryl or Heterocyclic)-phenyl]-3-[(2-carboxymethoxy-4-methoxy)phenyl]-2-propen-1-ones.
-continued

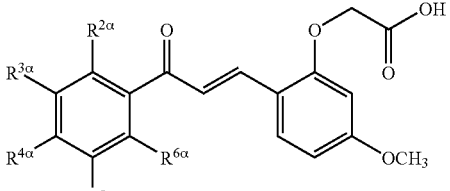

| EXAMPLE NO. | R2α | R3α | R4α | R5α | R6α |
|---|---|---|---|---|---|
| 330 | H | H | 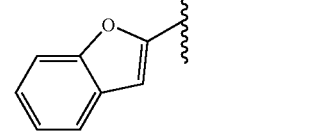 | H | H |
| 331 | H | H | 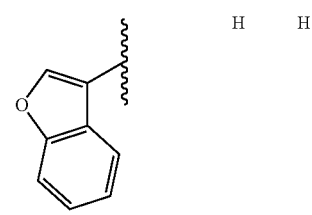 | H | H |
| 332 | H | H | 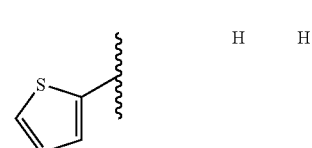 | H | H |
| 333 | H | H | 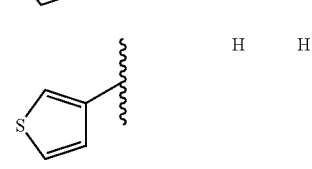 | H | H |
| 334 | H | H | 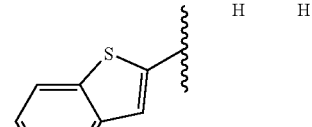 | H | H |
| 335 | H | H |  | H | H |
| 336 | H | H | 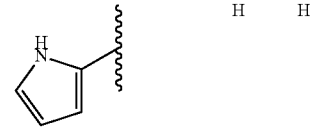 | H | H |

-continued
Example Table 11. 1-[4-(Heteroaryl or Heterocyclic)-phenyl]-3-[(2-carboxymethoxy-4-methoxy)phenyl]-2-propen-1-ones.
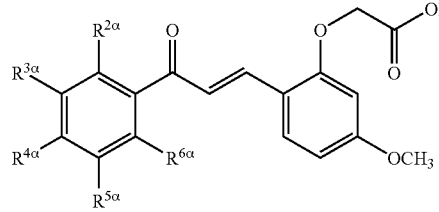
| EXAMPLE NO. | R2α | R3α | R4α | R5α | R6α |
|---|---|---|---|---|---|
| 337 | H | H | 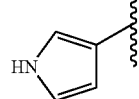 | H | H |
| 338 | H | H | 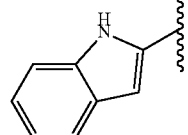 | H | H |
| 339 | H | H | 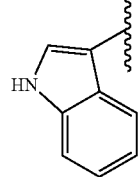 | H | H |
| 340 | H | H | 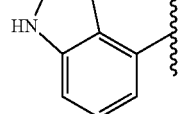 | H | H |
| 341 | H | H | 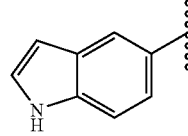 | H | H |
| 342 | H | H | 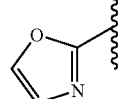 | H | H |
| 343 | H | H | 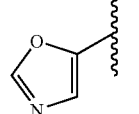 | H | H |
| 344 | H | H | 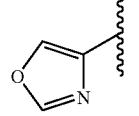 | H | H |
-continued
Example Table 11. 1-[4-(Heteroaryl or Heterocyclic)-phenyl]-3-[(2-carboxymethoxy-4-methoxy)phenyl]-2-propen-1-ones.
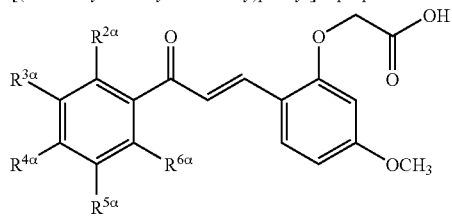
| EXAMPLE NO. | R2α | R3α | R4α | R5α | R6α |
|---|---|---|---|---|---|
| 345 | H | H | 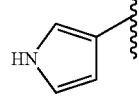 | H | H |
| 346 | H | H | 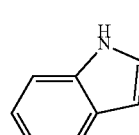 | H | H |
| 347 | H | H | 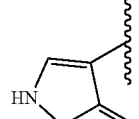 | H | H |
| 348 | H | H | 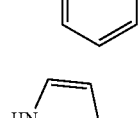 | H | H |
| 349 | H | H | 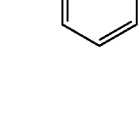 | H | H |
| 350 | H | H | 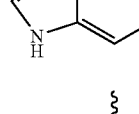 | H | H |
| 351 | H | H | 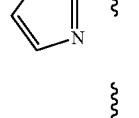 | H | H |
| 352 | H | H | 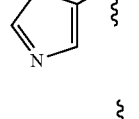 | H | H |

-continued

Example Table 11. 1-[4-(Heteroaryl or Heterocyclic)-phenyl]-3-[(2-carboxymethoxy-4-methoxy)phenyl]-2-propen-1-ones.

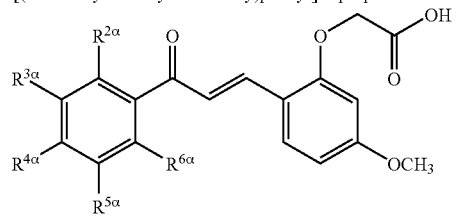

| EXAMPLE NO. | R2α | R3α | R4α | R5α | R6α |
|---|---|---|---|---|---|
| 353 | H | H | 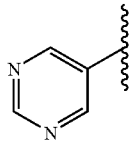 | H | H |
| 354 | H | H | 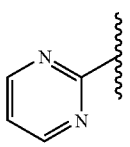 | H | H |
| 355 | H | H | 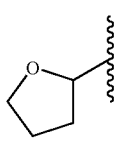 | H | H |
| 356 | H | H | 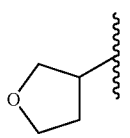 | H | H |
| 357 | H | H | 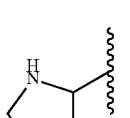 | H | H |
| 358 | H | H | 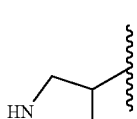 | H | H |
| 359 | H | H | 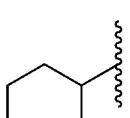 | H | H |
| 360 | H | H | 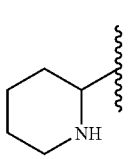 | H | H |

-continued

Example Table 11. 1-[4-(Heteroaryl or Heterocyclic)-phenyl]-3-[(2-carboxymethoxy-4-methoxy)phenyl]-2-propen-1-ones.

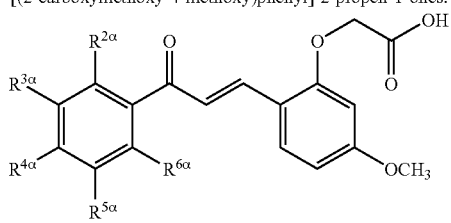

| EXAMPLE NO. | R2α | R3α | R4α | R5α | R6α |
|---|---|---|---|---|---|
| 361 | H | H | 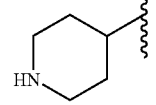 | H | H |
| 362 | H | H | 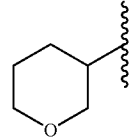 | H | H |
| 363 | H | H | 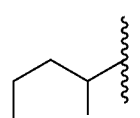 | H | H |
| 364 | H | H | 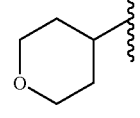 | H | H |

Example Table 12. 3-[3 or 6-(Heteroaryl)-2-carboxymethoxy-4-methoxy)phenyl]-1-[(3,4,5-trimethoxy)phenyl]-2-propen-1-ones.

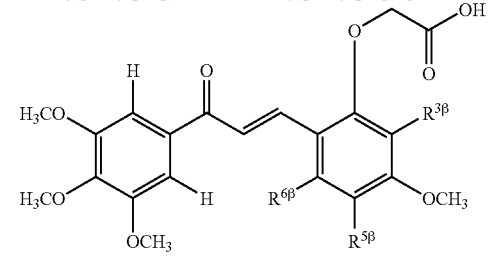

| Example Number | R3β | R5β | R6β |
|---|---|---|---|
| 365 | H | H | 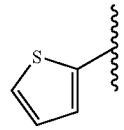 |

-continued

Example Table 12. 3-[3 or 6-(Heteroaryl)-2-carboxymethoxy-4-methoxy)phenyl]-1-[(3,4,5-trimethoxy)phenyl]-2-propen-1-ones.

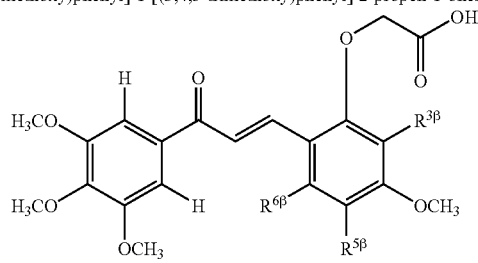

| Example Number | R3β | R5β | R6β |
|---|---|---|---|
| 366 | H | H | 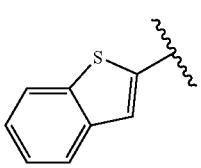 |
| 367 | 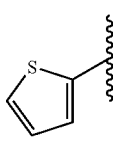 | H | H |
| 368 | 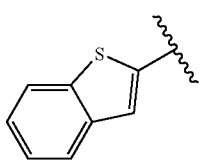 | H | H |

Example Table 13. 3-[3 or 6-(Heteroaryl)-2,4-dimethoxy)phenyl]-1-[(3,4,5-trimethoxy)phenyl]-2-propen-1-ones.

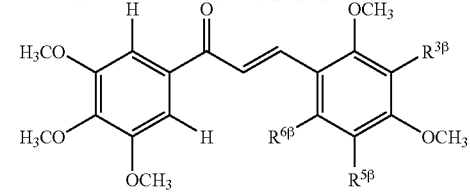

| Example Number | R3β | R5β | R6β |
|---|---|---|---|
| 369 | H | H | 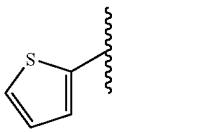 |
| 370 | H | H | 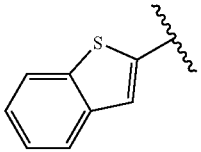 |

Example Table 13. 3-[3 or 6-(Heteroaryl)-2,4-dimethoxy)phenyl]-1-[(3,4,5-trimethoxy)phenyl]-2-propen-1-ones.

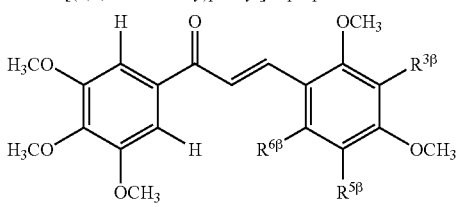

| Example Number | R3β | R5β | R6β |
|---|---|---|---|
| 371 | 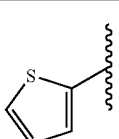 | H | H |
| 372 | 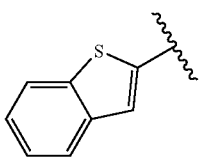 | H | H |

Example Table 14. 3-[2 or 6-(Heteroaryl)-3,4-dimethoxy)phenyl]-1-[(3,4,5-trimethoxy)phenyl]-2-propen-1-ones.

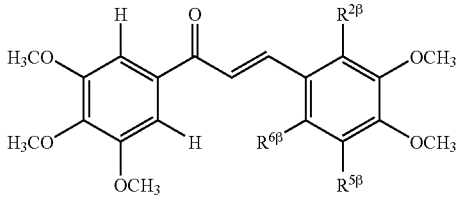

| Example Number | R3β | R5β | R6β |
|---|---|---|---|
| 373 | H | H |  |
| 374 | H | H |  |
| 375 |  | H | H |

-continued
Example Table 14. 3-[2 or 6-(Heteroaryl)-3,4-dimethoxy)phenyl]-1-[(3,4,5-trimethoxy)phenyl]-2-propen-1-ones.
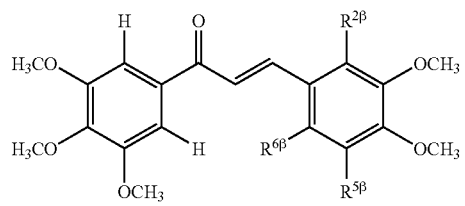
| Example Number | R3β | R5β | R6β |
|---|---|---|---|
| 376 | 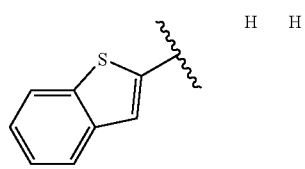 | H | H |
Example Table 15. Substituted 1-[2- or 3-(Heteroaryl)-phenyl]-3-[(2-carboxymethoxy)-4-methoxyphenyl]-2-propen-1-ones.
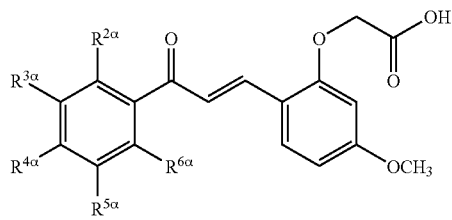
| EXAMPLE NUMBER | R2α | R3α | R4α | R5α | R6α |
|---|---|---|---|---|---|
| 377 | 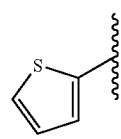 | H | F | H | H |
| 378 | 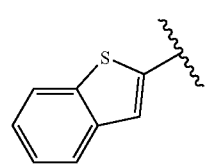 | H | F | H | H |
| 379 | H | 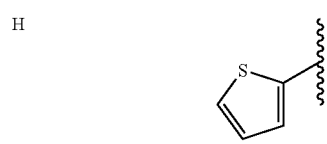 | F | H | H |

Example Table 15. Substituted 1-[2- or 3-(Heteroaryl)-phenyl]-3-[(2-carboxymethoxy)-4-methoxyphenyl]-2-propen-1-ones.
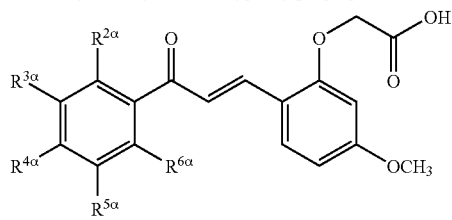
| EXAMPLE NUMBER | R2α | R3α | R4α | R5α | R6α |
|---|---|---|---|---|---|
| 380 | H | 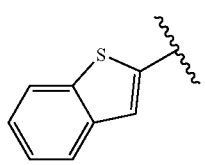 | F | H | H |
Example Table 16. Substituted 1-[2- or 3-(Heteroaryl)-phenyl]-3-[(2,4-dimethoxy)phenyl]-2-propen-1-ones.
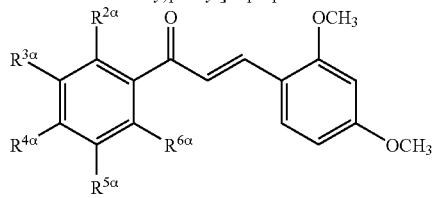
| EXAMPLE NUMBER | R2α | R3α | R4α | R5α | R6α |
|---|---|---|---|---|---|
| 381 | 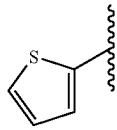 | H | F | H | H |
| 382 | 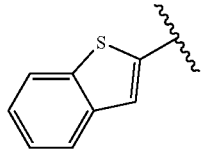 | H | F | H | H |
| 383 | H | 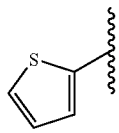 | F | H | H |
| 384 | H | 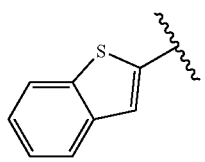 | F | H | H |

Example Table 17. Substituted 1-[2- or 3-(Heteroaryl)-phenyl]-3-[(3,4-dimethoxy)phenyl]-2-propen-1-ones.
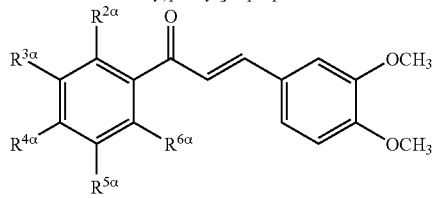
| EXAMPLE NUMBER | R2α | R3α | R4α | R5α | R6α |
|---|---|---|---|---|---|
| 385 | 2-thienyl | H | F | H | H |
| 386 | 2-benzothienyl | H | F | H | H |
| 387 | H | 2-thienyl | F | H | H |
| 388 | H | 2-benzothienyl | F | H | H |
Example Table 18. Substituted 3-[3-, 5- or 6-(Heteroaryl)-2-(carboxymethoxy)-4-methoxyphenyl]-1-phenyl-2-propen-1-ones.
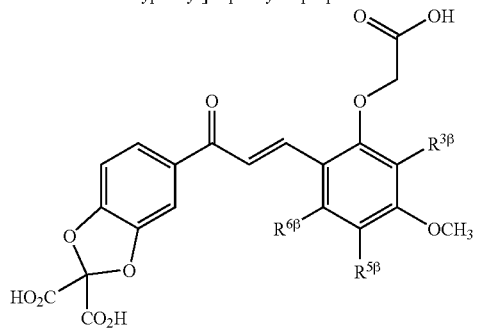
| Example Number | R3β | R5β | R6β |
|---|---|---|---|
| 389 | H | 2-thienyl | H |

Example Table 18. Substituted 3-[3-, 5- or 6-(Heteroaryl)-2-(carboxymethoxy)-4-methoxyphenyl]-1-phenyl-2-propen-1-ones.
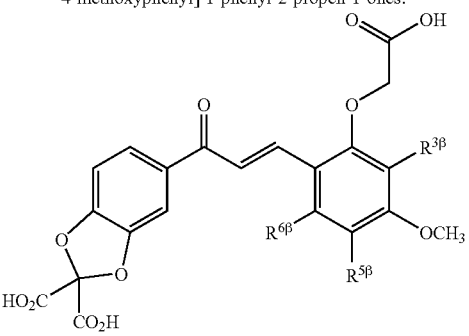
| Example Number | R3β | R5β | R6β |
|---|---|---|---|
| 390 | H | benzothiophen-2-yl | H |
| 391 | H | H | thiophen-2-yl |
| 392 | H | H | benzothiophen-2-yl |
| 393 | thiophen-2-yl | H | H |
| 394 | benzothiophen-2-yl | H | H |

Example Table 19. Substituted 3-[3-, 5- or 6-(Heteroaryl)-2,4-dimethoxyphenyl]-1-phenyl-2-propen-1-ones.
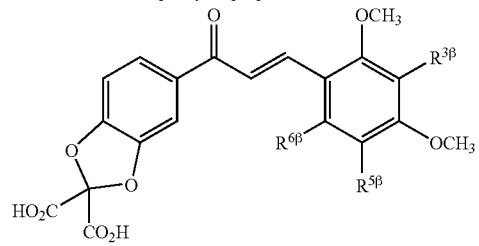
| Example Number | R3β | R5β | R6β |
|---|---|---|---|
| 395 | H | 2-thienyl | H |
| 396 | H | benzothiophen-2-yl | H |
| 397 | H | H | 2-thienyl |
| 398 | H | H | benzothiophen-2-yl |
| 399 | 2-thienyl | H | H |
| 400 | benzothiophen-2-yl | H | H |

Example Table 20. Substituted 3-[2-, 5- or 6-(Heteroaryl)-3,4-dimethoxyphenyl]-1-phenyl-2-propen-1-ones.
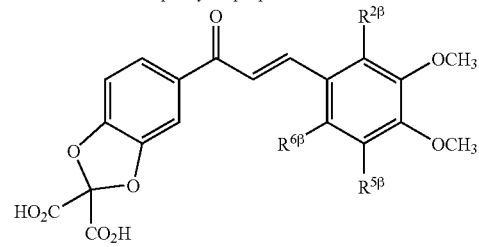
| Example Number | R2β | R5β | R6β |
|---|---|---|---|
| 401 | H | 2-thienyl | H |
| 402 | H | benzothiophen-2-yl | H |
| 403 | H | H | 2-thienyl |
| 404 | H | H | benzothiophen-2-yl |
| 405 | 2-thienyl | H | H |
| 406 | benzothiophen-2-yl | H | H |

Example Table 21. Substituted 3-[5-(benzo[b]thien-2-yl)-4-carboxymethoxy-2-methoxyphenyl]-1-phenyl-2-propen-1-ones.

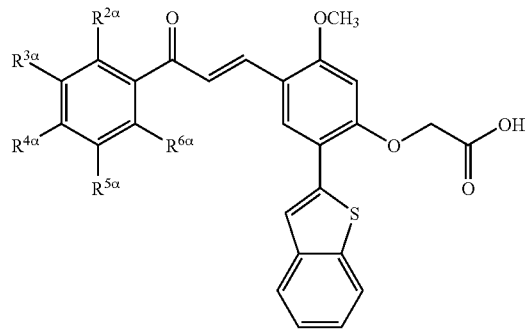

| EXAMPLE NUMBER | R2α | R3α | R4α | R5α | R6α |
|---|---|---|---|---|---|
| 407 | H | OMe | OCH2-cyclopropyl | OMe | H |
| 408 | OMe | H | H | H | H |
| 409 | H | OMe | H | H | H |
| 410 | H | H | F | H | H |
| 411 | F | H | H | H | H |
| 412 | H | F | H | H | H |
| 413 | F | F | F | F | F |
| 414 | F | H | F | H | H |
| 415 | H | F | F | H | H |
| 416 | H | F | H | F | H |
| 417 | H | OMe | OCF3 | OMe | H |
| 418 | F | H | OMe | H | H |
| 419 | H | F | OMe | H | H |
| 420 | OH | H | F | H | H |
| 421 | OH | H | H | F | H |
| 422 | OMe | H | F | H | H |
| 423 | OMe | H | H | F | H |
| 424 | OMe | H | CH3 | H | H |
| 425 | OMe | H | H | CH3 | H |
| 426 | OMe | CH3 | H | H | H |
| 427 | OMe | H | H | H | CH3 |
| 428 | H | OMe | F | OMe | H |
| 429 | H | OMe | Cl | OMe | H |
| 430 | H | OMe | COOH | OMe | H |
| 431 | H | OMe | OCH2COOH | OMe | H |
| 432 | H | OMe | CH2COOH | OMe | H |
| 433 | H | OMe | SCH2COOH | OMe | H |
| 434 | H | OMe | SO3H | OMe | H |
| 435 | H | OMe | SO2NH2 | OMe | H |
| 436 | H | OMe | SO2N(Me)2 | OMe | H |
| 437 | H | OMe | OCH2CH(NH2)COOH | OMe | H |
| 438 | H | OMe | NH2 | OMe | H |
| 439 | H | OMe | N(CH3)2 | OMe | H |
| 440 | H | OMe | N(H)CH2COOH | OMe | H |
| 441 | H | OMe | pyrrolidin-1-yl | OMe | H |
| 442 | H | OMe | piperidin-1-yl | OMe | H |
| 443 | H | OMe | piperazin-1-yl | OMe | H |
| 444 | H | OMe | 4-methylpiperazin-1-yl | OMe | H |
| 445 | H | OMe | CH3 | OMe | H |
| 446 | H | OMe | CF3 | OMe | H |
| 447 | H | OMe | OMe | OMe | H |
| 448 | OMe | OMe | OMe | H | H |
| 449 | H | OMe | OMe | H | H |

Example Table 22. Substituted 3-[5-(benzo[b]thien-2-yl)-2-carboxymethoxy-4-methoxyphenyl]-1-phenyl-2-propen-1-ones.

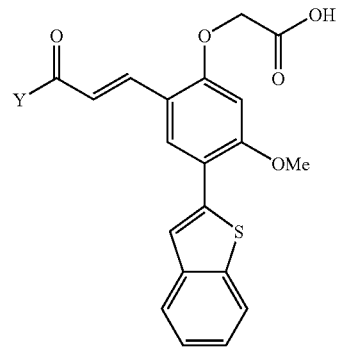

| Ex. No. | Y |
|---|---|
| 450 | benzofuran-5-yl |

Example Table 22. Substituted 3-[5-(benzo[b]thien-2-yl)-2-carboxymethoxy-4-methoxyphenyl]-1-phenyl-2-propen-1-ones.
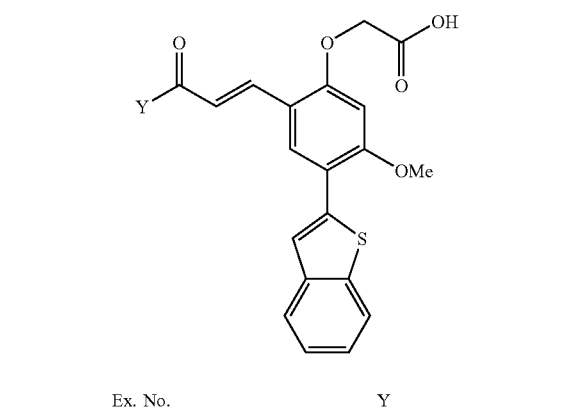
| Ex. No. | Y |
|---|---|
| 451 | 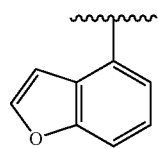 |
| 452 | 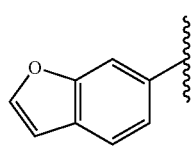 |
| 453 | 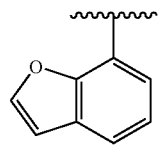 |
| 454 | 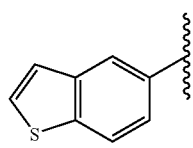 |
| 455 | 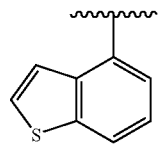 |
| 456 | 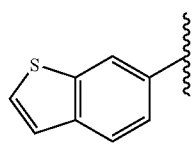 |
Example Table 22. Substituted 3-[5-(benzo[b]thien-2-yl)-2-carboxymethoxy-4-methoxyphenyl]-1-phenyl-2-propen-1-ones.
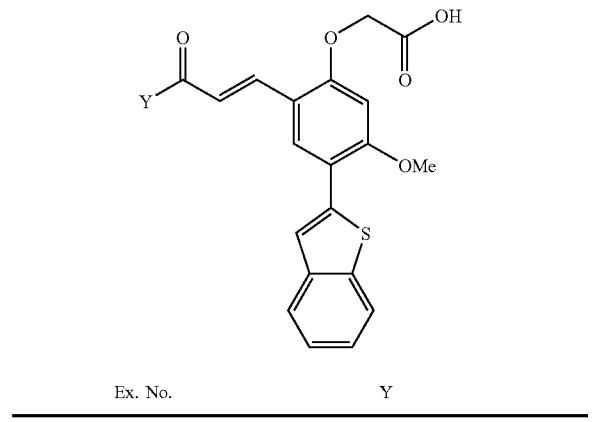
| Ex. No. | Y |
|---|---|
| 457 | 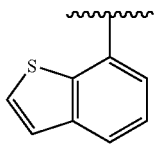 |
| 458 | 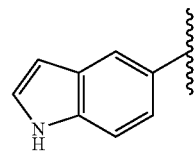 |
| 459 | 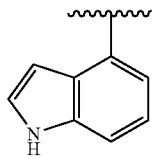 |
| 460 | 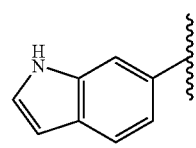 |
| 461 | 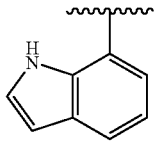 |
| 462 | 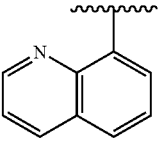 |

-continued

Example Table 22. Substituted 3-[5-(benzo[b]thien-2-yl)-2-carboxymethoxy-4-methoxyphenyl]-1-phenyl-2-propen-1-ones.

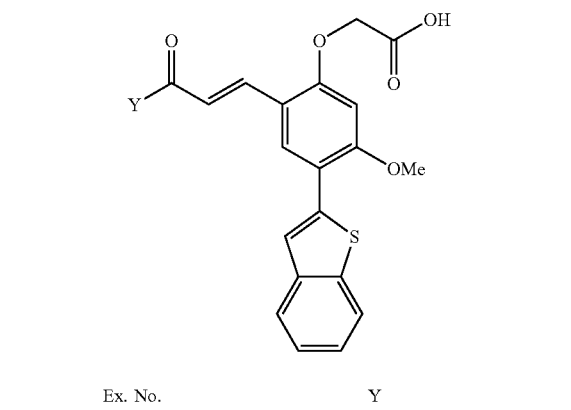

| Ex. No. | Y |
|---|---|
| 463 | 1H-benzimidazol-5-yl |
| 464 | 1H-benzimidazol-4-yl |
| 465 | 1H-benzimidazol-6-yl |
| 466 | 1H-benzimidazol-7-yl |
| 467 | benzoxazol-5-yl |
| 468 | benzoxazol-4-yl |

-continued

Example Table 22. Substituted 3-[5-(benzo[b]thien-2-yl)-2-carboxymethoxy-4-methoxyphenyl]-1-phenyl-2-propen-1-ones.

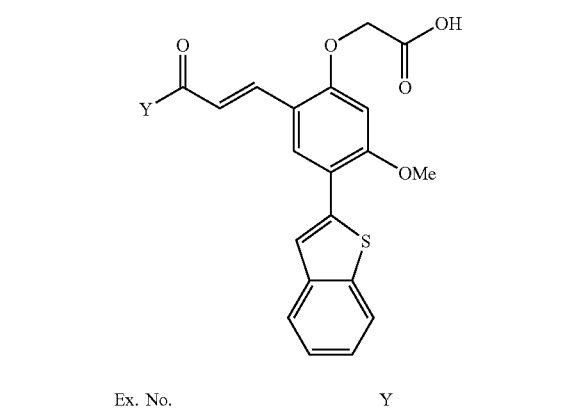

| Ex. No. | Y |
|---|---|
| 469 | benzoxazol-6-yl |
| 470 | benzoxazol-7-yl |
| 471 | benzothiazol-5-yl |
| 472 | benzothiazol-4-yl |
| 473 | benzothiazol-6-yl |
| 474 | quinolin-6-yl |
| 475 | quinolin-5-yl |

-continued

Example Table 22. Substituted 3-[5-(benzo[b]thien-2-yl)-2-carboxymethoxy-4-methoxyphenyl]-1-phenyl-2-propen-1-ones.

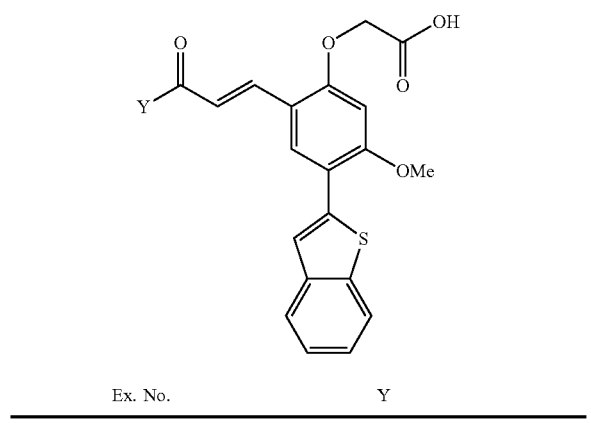

| Ex. No. | Y |
|---|---|
| 476 | 1,2,3,4-tetrahydroquinolin-7-yl |
| 477 | 1,2,3,4-tetrahydroquinolin-8-yl |
| 478 | quinazolin-6-yl |
| 479 | quinazolin-5-yl |
| 480 | quinazolin-7-yl |
| 481 | quinazolin-8-yl |
| 482 | quinoxalin-6-yl |
| 483 | quinoxalin-5-yl |
| 484 | isoquinolin-6-yl |
| 485 | 1,2,3,4-tetrahydroisoquinolin-6-yl |
| 486 | benzothiazol-7-yl |
| 487 | quinolin-6-yl |
| 488 | 1,2,3,4-tetrahydroquinolin-5-yl |
| 489 | 1,2,3,4-tetrahydroquinolin-6-yl |

Example Table 23. Substituted 3-[4-(heteroaryl or heterocyclic)-2,4-dimethoxyphenyl]-1-[(3,5-dimethoxy)-4-carboxymethoxyphenyl]-2-propen-1-ones.
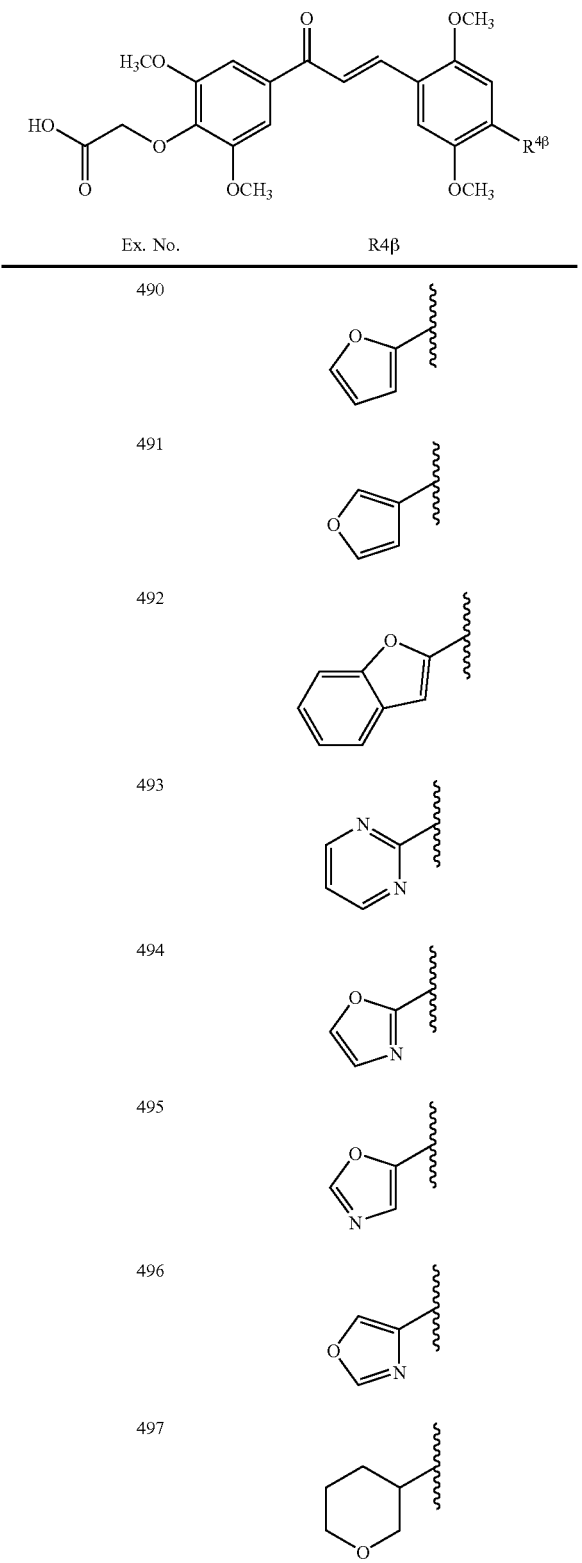
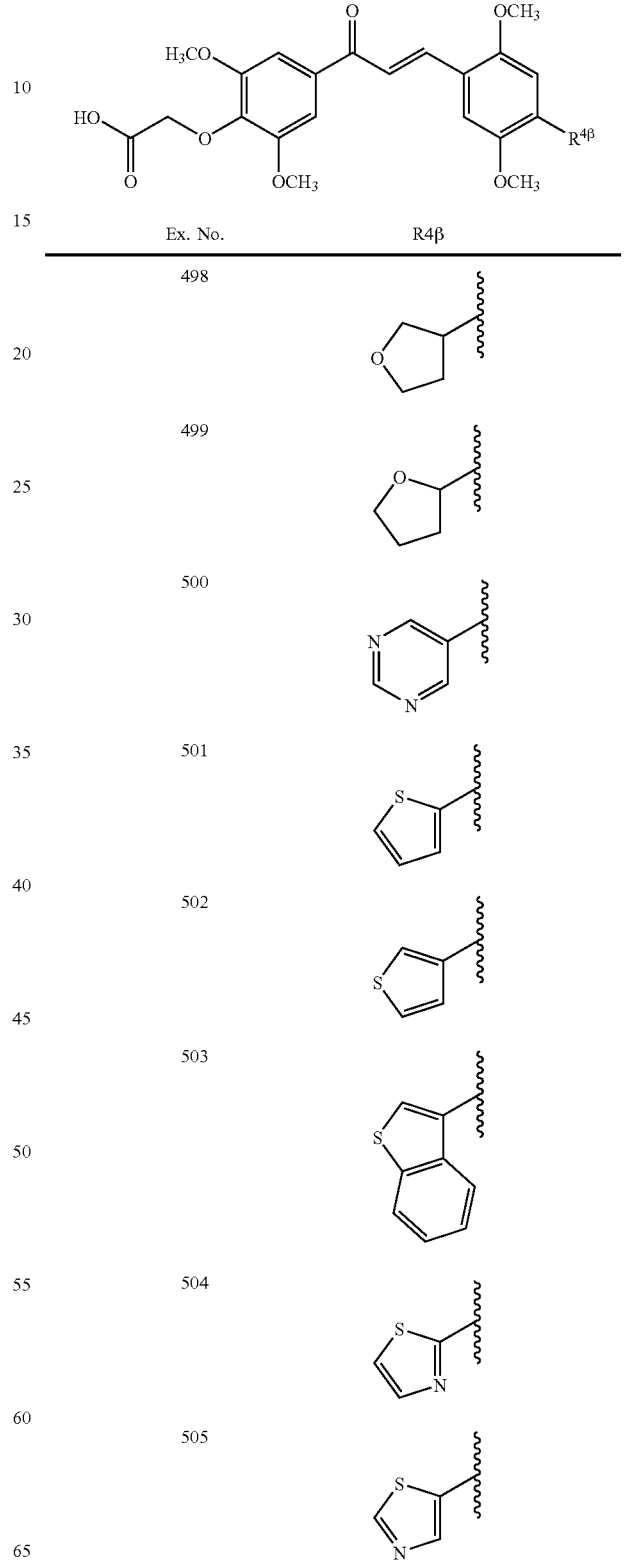

Example Table 23. Substituted 3-[4-(heteroaryl or heterocyclic)-2,4-dimethoxyphenyl]-1-[(3,5-dimethoxy)-4-carboxymethoxyphenyl]-2-propen-1-ones.
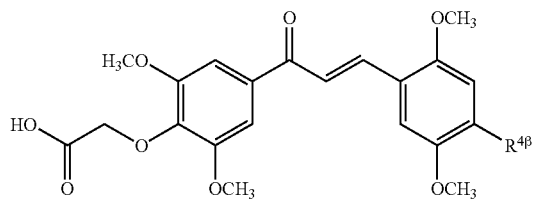
| Ex. No. | R4β |
|---|---|
| 506 | 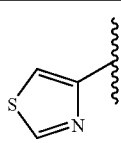 |
| 507 | 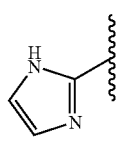 |
| 508 | 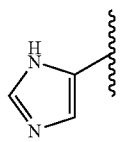 |
| 509 | 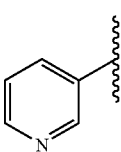 |
| 510 | 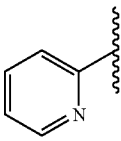 |
| 511 | 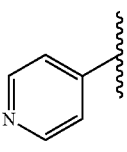 |
| 512 | 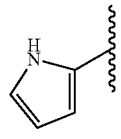 |
| 513 | 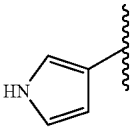 |
Example Table 23. Substituted 3-[4-(heteroaryl or heterocyclic)-2,4-dimethoxyphenyl]-1-[(3,5-dimethoxy)-4-carboxymethoxyphenyl]-2-propen-1-ones.
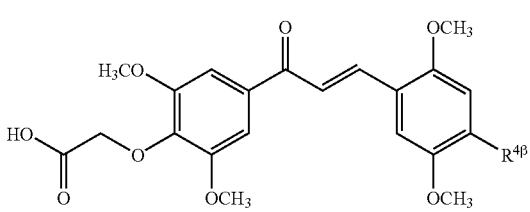
| Ex. No. | R4β |
|---|---|
| 514 | 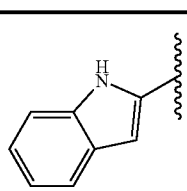 |
| 515 | 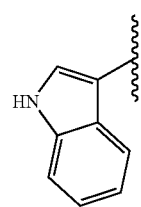 |
| 516 | 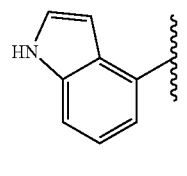 |
| 517 | 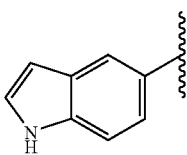 |
| 518 | 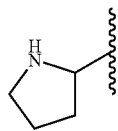 |
| 519 | 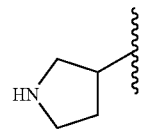 |
| 520 | 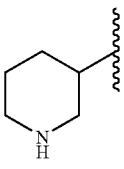 |

-continued

Example Table 23. Substituted 3-[4-(heteroaryl or heterocyclic)-2,4-dimethoxyphenyl]-1-[(3,5-dimethoxy)-4-carboxymethoxyphenyl]-2-propen-1-ones.

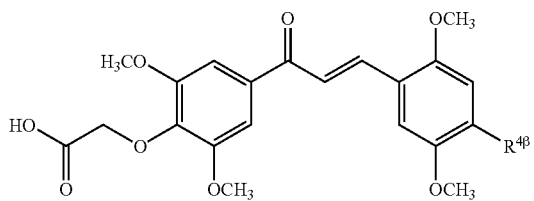

| Ex. No. | R4β |
|---|---|
| 521 | 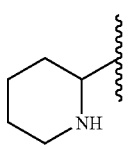 |
| 522 | 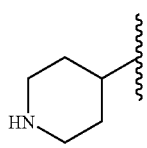 |

Example Table 24. 3-[4-(Heteroaryl or Heterocyclic)-2-carboxymethoxy-4-methoxyphenyl]-1-[(3,4,5-trimethoxy)phenyl]-2-propen-1-ones.

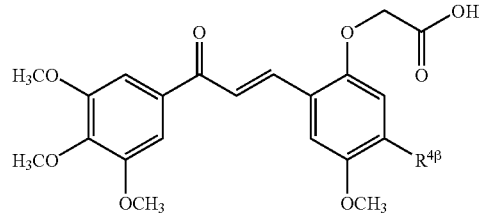

| Ex. No. | R4β |
|---|---|
| 523 | 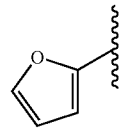 |
| 524 | 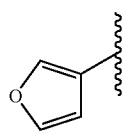 |
| 525 | 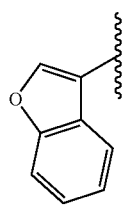 |

-continued

Example Table 24. 3-[4-(Heteroaryl or Heterocyclic)-2-carboxymethoxy-4-methoxyphenyl]-1-[(3,4,5-trimethoxy)phenyl]-2-propen-1-ones.

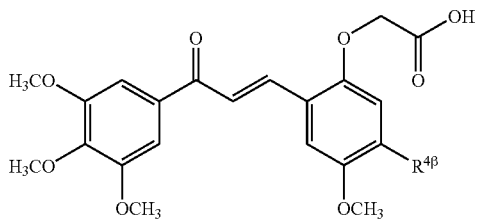

| Ex. No. | R4β |
|---|---|
| 526 | 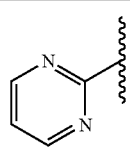 |
| 527 | 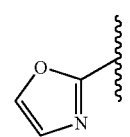 |
| 528 | 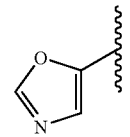 |
| 529 | 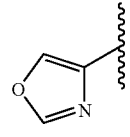 |
| 530 | 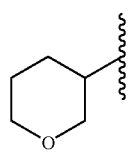 |
| 531 | 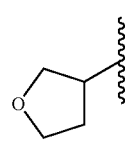 |
| 532 | 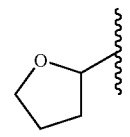 |
| 533 | 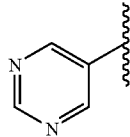 |

Example Table 24. 3-[4-(Heteroaryl or Heterocyclic)-2-carboxymethoxy-4-methoxyphenyl]-1-[(3,4,5-trimethoxy)phenyl]-2-propen-1-ones.
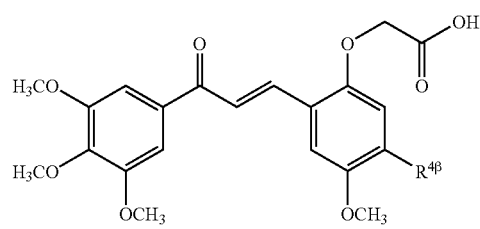
| Ex. No. | R4β |
|---|---|
| 534 | 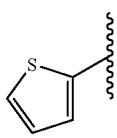 |
| 535 | 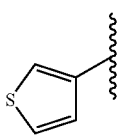 |
| 536 | 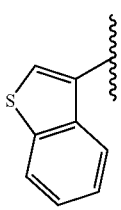 |
| 537 | 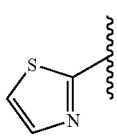 |
| 538 | 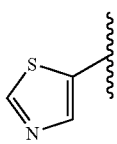 |
| 539 | 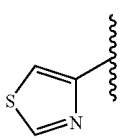 |
| 540 | 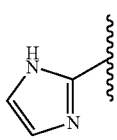 |
Example Table 24. 3-[4-(Heteroaryl or Heterocyclic)-2-carboxymethoxy-4-methoxyphenyl]-1-[(3,4,5-trimethoxy)phenyl]-2-propen-1-ones.
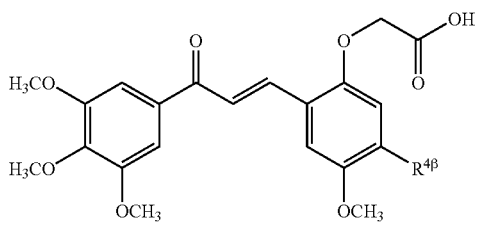
| Ex. No. | R4β |
|---|---|
| 541 | 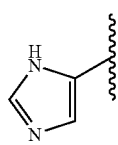 |
| 542 | 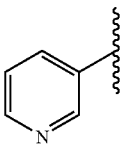 |
| 543 | 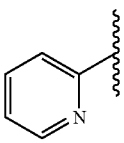 |
| 544 | 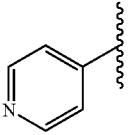 |
| 545 | 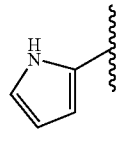 |
| 546 | 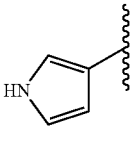 |
| 547 | 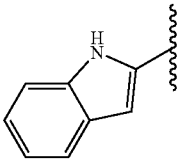 |

Example Table 24. 3-[4-(Heteroaryl or Heterocyclic)-2-carboxymethoxy-4-methoxyphenyl]-1-[(3,4,5-trimethoxy)phenyl]-2-propen-1-ones.
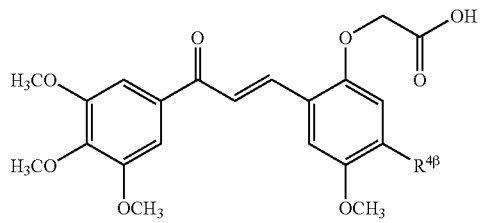
| Ex. No. | R4β |
|---|---|
| 548 | 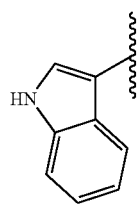 |
| 549 | 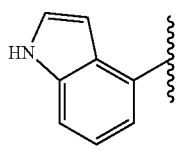 |
| 550 | 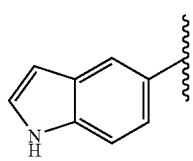 |
| 551 | 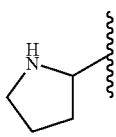 |
| 552 | 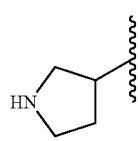 |
| 553 | 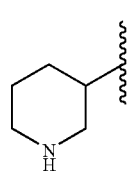 |
| 554 | 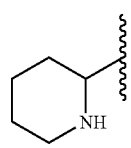 |
Example Table 24. 3-[4-(Heteroaryl or Heterocyclic)-2-carboxymethoxy-4-methoxyphenyl]-1-[(3,4,5-trimethoxy)phenyl]-2-propen-1-ones.
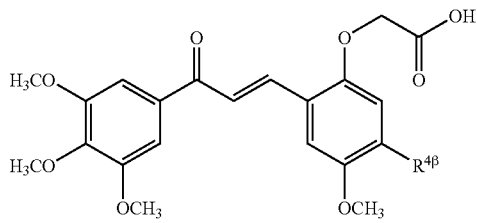
| Ex. No. | R4β |
|---|---|
| 555 | 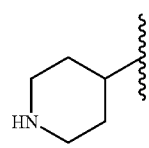 |
Example Table 25. 3-[4-(Heteroaryl or Heterocyclic)-2,4-dimethoxyphenyl]-1-[(3,4,5-trimethoxy)phenyl]-2-propen-1-ones.
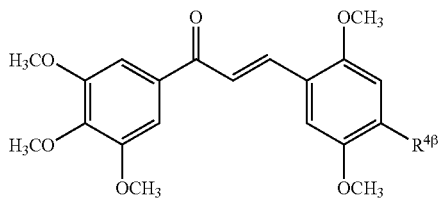
| Ex. No. | R4β |
|---|---|
| 556 | 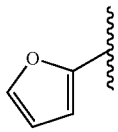 |
| 557 | 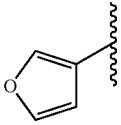 |
| 558 | 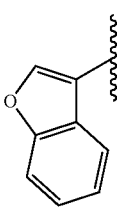 |
| 559 | 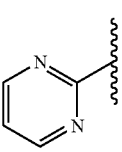 |

-continued
Example Table 25. 3-[4-(Heteroaryl or Heterocyclic)-2,4-dimethoxyphenyl]-1-[(3,4,5-trimethoxy)phenyl]-2-propen-1-ones.
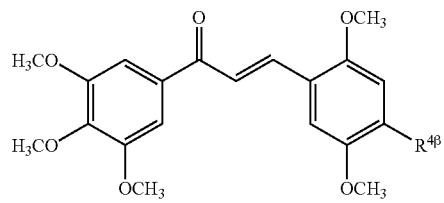
| Ex. No. | R4β |
|---|---|
| 560 | 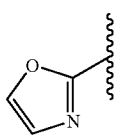 |
| 561 | 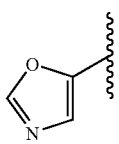 |
| 562 | 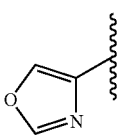 |
| 563 | 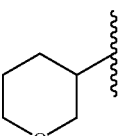 |
| 564 | 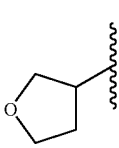 |
| 565 | 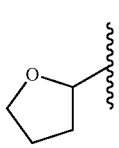 |
| 566 | 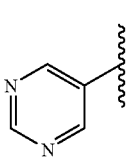 |
-continued
Example Table 25. 3-[4-(Heteroaryl or Heterocyclic)-2,4-dimethoxyphenyl]-1-[(3,4,5-trimethoxy)phenyl]-2-propen-1-ones.
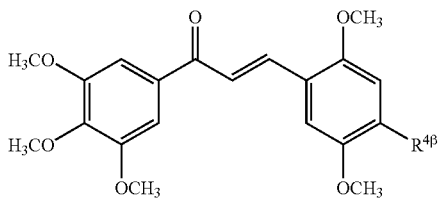
| Ex. No. | R4β |
|---|---|
| 567 | 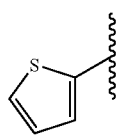 |
| 568 | 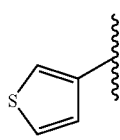 |
| 569 | 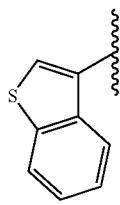 |
| 570 | 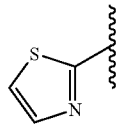 |
| 571 | 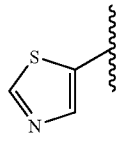 |
| 572 | 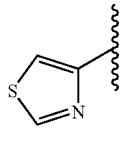 |
| 573 | 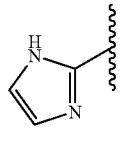 |

-continued
Example Table 25. 3-[4-(Heteroaryl or Heterocyclic)-2,4-dimethoxyphenyl]-1-[(3,4,5-trimethoxy)phenyl]-2-propen-1-ones.
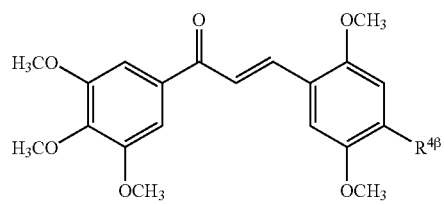
| Ex. No. | R4β |
|---|---|
| 574 | 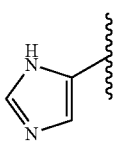 |
| 575 | 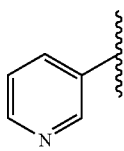 |
| 576 | 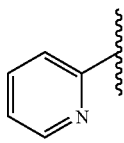 |
| 577 | 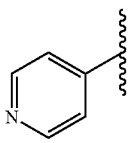 |
| 578 | 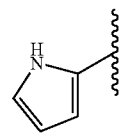 |
| 579 | 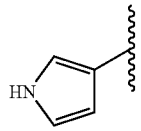 |
| 580 | 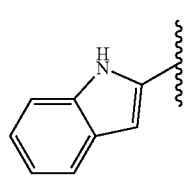 |
-continued
Example Table 25. 3-[4-(Heteroaryl or Heterocyclic)-2,4-dimethoxyphenyl]-1-[(3,4,5-trimethoxy)phenyl]-2-propen-1-ones.
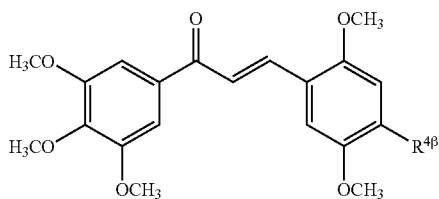
| Ex. No. | R4β |
|---|---|
| 581 | 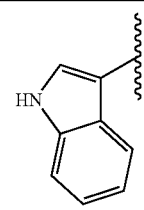 |
| 582 | 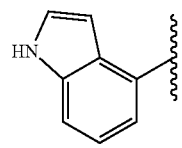 |
| 583 | 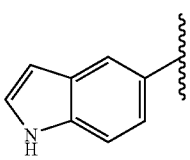 |
| 584 | 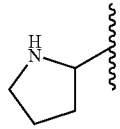 |
| 585 | 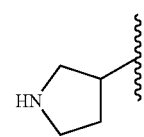 |
| 586 | 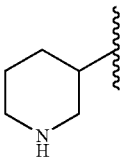 |
| 587 | 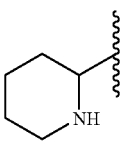 |
| 588 | 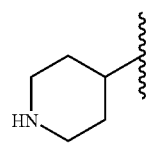 |

Example Table 26. 3-[4-(Heteroaryl or Heterocyclic)-3,5-dimethoxyphenyl]-1-[(3,4,5-trimethoxy)phenyl]-2-propen-1-ones.
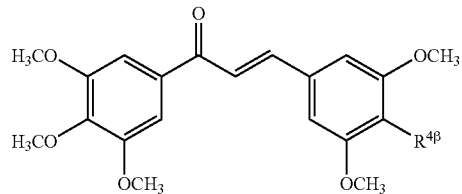
| Ex. No. | R4β |
|---|---|
| 589 | 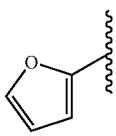 |
| 590 | 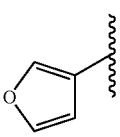 |
| 591 | 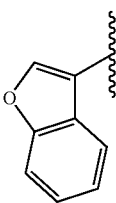 |
| 592 | 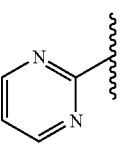 |
| 593 | 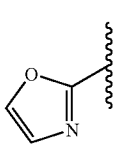 |
| 594 | 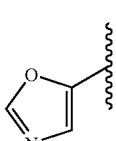 |
| 595 | 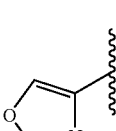 |
| 596 | 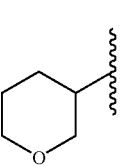 |
-continued
Example Table 26. 3-[4-(Heteroaryl or Heterocyclic)-3,5-dimethoxyphenyl]-1-[(3,4,5-trimethoxy)phenyl]-2-propen-1-ones.
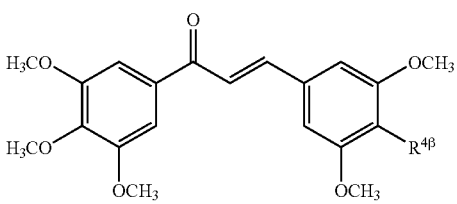
| Ex. No. | R4β |
|---|---|
| 597 | 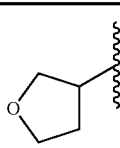 |
| 598 | 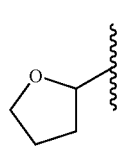 |
| 599 | 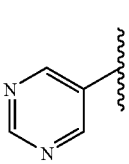 |
| 600 | 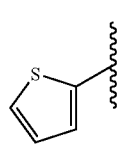 |
| 601 | 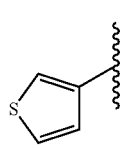 |
| 602 | 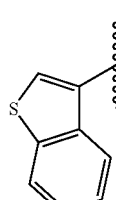 |
| 603 | 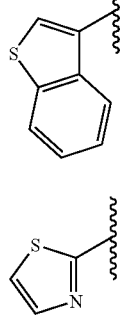 |
| 604 | 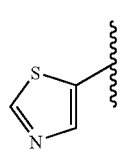 |

-continued
Example Table 26. 3-[4-(Heteroaryl or Heterocyclic)-3,5-dimethoxyphenyl]-1-[(3,4,5-trimethoxy)phenyl]-2-propen-1-ones.
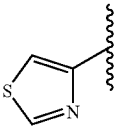
| Ex. No. | R4β |
|---|---|
| 605 | 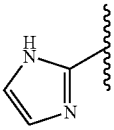 |
| 606 | 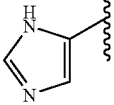 |
| 607 | 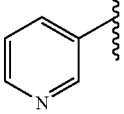 |
| 608 | 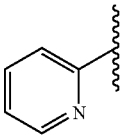 |
| 609 | 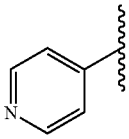 |
| 610 | 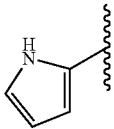 |
| 611 | 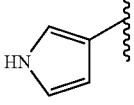 |
| 612 | 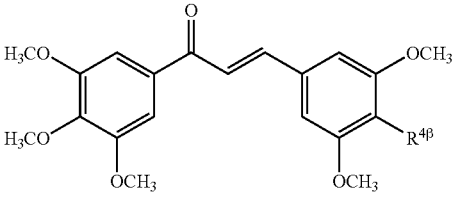 |
-continued
Example Table 26. 3-[4-(Heteroaryl or Heterocyclic)-3,5-dimethoxyphenyl]-1-[(3,4,5-trimethoxy)phenyl]-2-propen-1-ones.
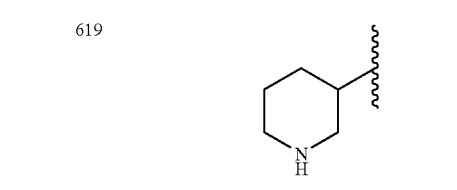
| Ex. No. | R4β |
|---|---|
| 613 | 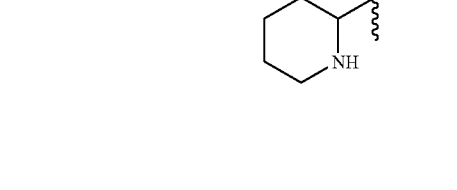 |
| 614 | 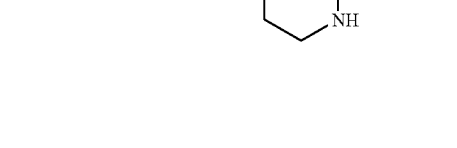 |
| 615 |  |
| 616 |  |
| 617 |  |
| 618 | 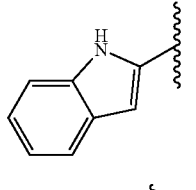 |
| 619 | 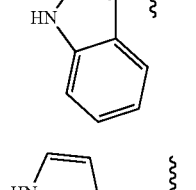 |
| 620 | 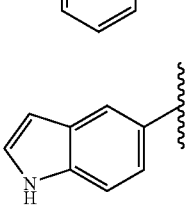 |

-continued

Example Table 26. 3-[4-(Heteroaryl or Heterocyclic)-3,5-dimethoxyphenyl]-1-[(3,4,5-trimethoxy)phenyl]-2-propen-1-ones.

| Ex. No. | R4β |
|---|---|
| 621 | (4-piperidinyl) |

Example Table 27. Substituted 3-[4-(pyran-2-yl)phenyl]-1-[(3,5-dimethoxy)phenyl]-2-propen-1-ones.

| Example Number | R4α | R2β | R3β | R5β |
|---|---|---|---|---|
| 622 | F | OMe | H | OMe |
| 623 | OCH2COOH | OMe | OMe | H |
| 624 | F | OCH2COOH | H | OMe |

Example Table 28. Substituted 3-[4-(pyran-4-yl)phenyl]-1-[(3,5-dimethoxy)phenyl]-2-propen-1-ones.

| Example Number | R4α | R2β | R3β | R5β |
|---|---|---|---|---|
| 625 | F | OMe | H | OMe |
| 626 | OCH2COOH | OMe | OMe | H |
| 627 | F | OCH2COOH | H | OMe |

Example Table 29. Substituted 3-[5-(benzo[b]thien-2-yl)-2-(2-carboxy-2-propoxy)-4-methoxyphenyl]-1-phenyl-2-propen-1-ones.

| Ex. No. | Y |
|---|---|
| 629 | benzofuran-5-yl |
| 630 | benzofuran-4-yl |
| 631 | benzofuran-6-yl |
| 632 | benzofuran-7-yl |
| 633 | benzo[b]thien-5-yl |
| 634 | benzo[b]thien-4-yl |
| 635 | benzo[b]thien-6-yl |

-continued
Example Table 29. Substituted 3-[5-(benzo[b]thien-2-yl)-2-(2-carboxy-2-propoxy)-4-methoxyphenyl]-1-phenyl-2-propen-1-ones.
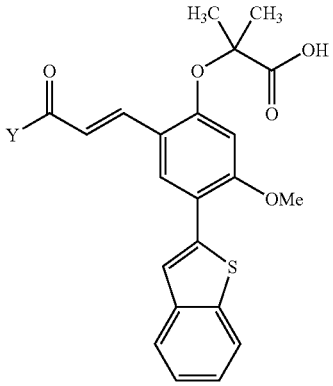
| Ex. No. | Y |
|---|---|
| 636 | 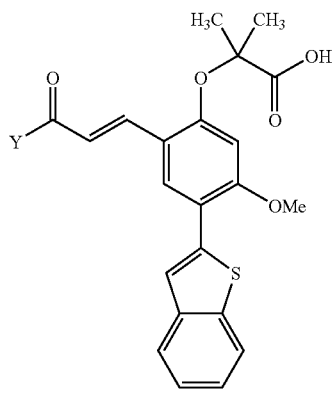 |
| 637 | 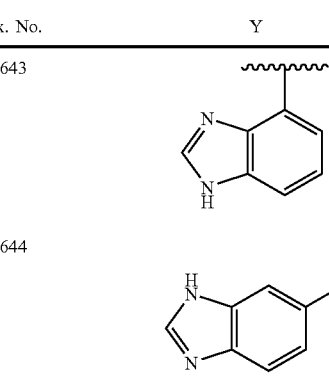 |
| 638 | 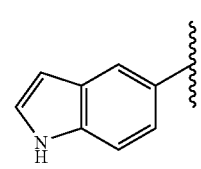 |
| 639 | 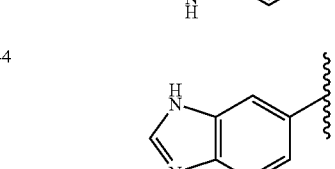 |
| 640 | 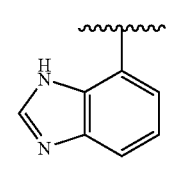 |
| 641 | 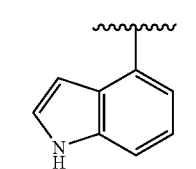 |
| 642 | 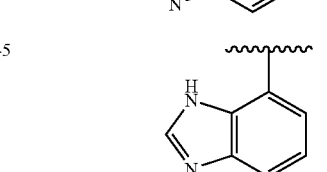 |
-continued
Example Table 29. Substituted 3-[5-(benzo[b]thien-2-yl)-2-(2-carboxy-2-propoxy)-4-methoxyphenyl]-1-phenyl-2-propen-1-ones.
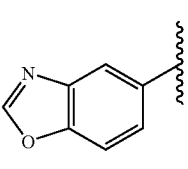
| Ex. No. | Y |
|---|---|
| 643 | 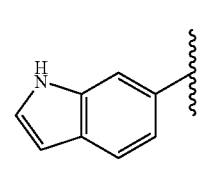 |
| 644 | 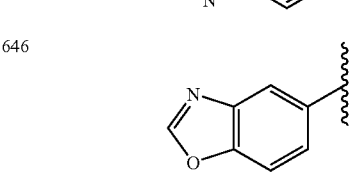 |
| 645 | 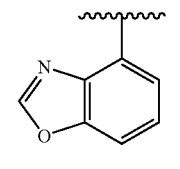 |
| 646 | 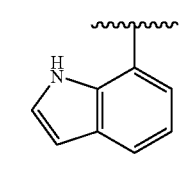 |
| 647 | 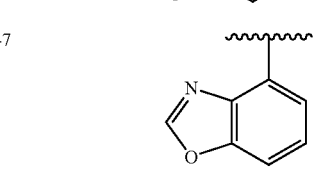 |
| 648 | 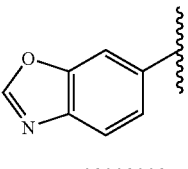 |
| 649 | 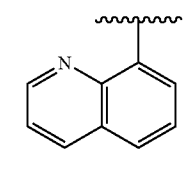 |

US 7,078,431 B2
Example Table 29. Substituted 3-[5-(benzo[b]thien-2-yl)-2-(2-carboxy-2-propoxy)-4-methoxyphenyl]-1-phenyl-2-propen-1-ones.
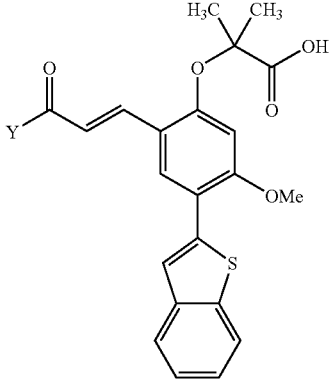
| Ex. No. | Y |
|---|---|
| 650 | 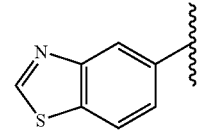 |
| 651 | 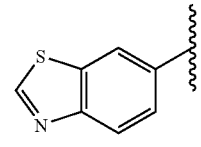 |
| 652 | 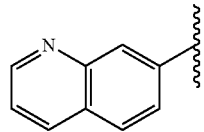 |
| 653 | 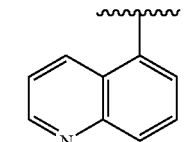 |
| 654 | 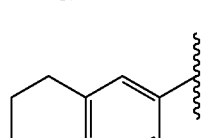 |
| 655 | 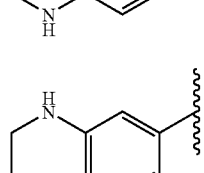 |
| 656 | 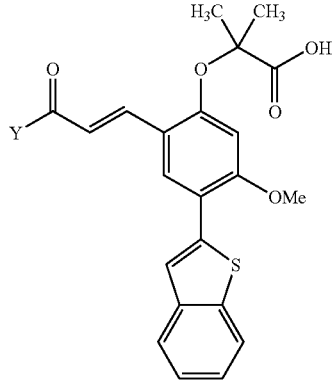 |
| 657 | 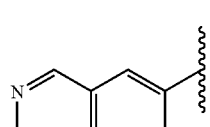 |
| 658 | 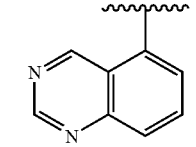 |
| 659 | 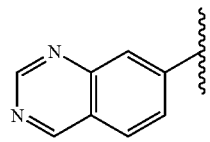 |
| 660 | 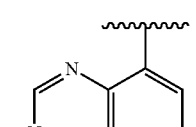 |
| 661 | 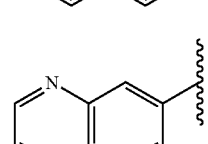 |
| 662 | 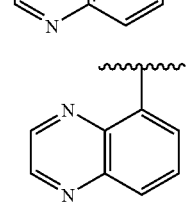 |
| 663 | |

Example Table 29. Substituted 3-[5-(benzo[b]thien-2-yl)-2-(2-carboxy-2-propoxy)-4-methoxyphenyl]-1-phenyl-2-propen-1-ones.

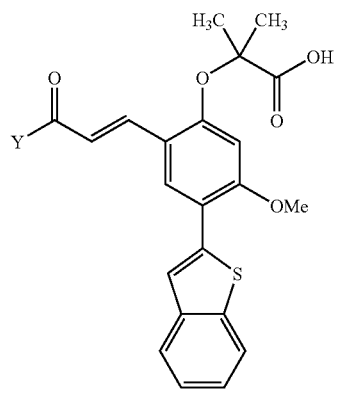

| Ex. No. | Y |
|---|---|
| 664 | 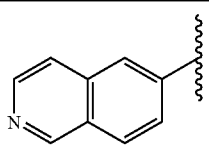 |
| 665 | 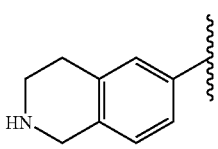 |
| 666 | 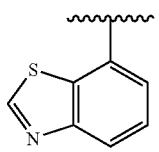 |
| 667 | 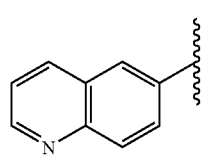 |
| 668 | 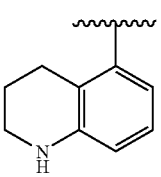 |

VIII. Biological Activity of Active Compounds

The ability of a compound described herein to inhibit the expression of VCAM-1 in a host can be assessed using any known method, including that described in detail below.

Preparing Vascular Endothelial Cells:

Two to four confluent P150 plates were trypsinized and the cells transferred to a 50 mL conical centrifuge tube. The cells were pelleted, resuspended and counted using the trypan blue exclusion method.

Cells were resuspended at a concentration of 36,000 cells/mL and 1 mL was aliquoted per well.

Cells were split into 24 well tissue culture plates. The cells in each well should be approximately 90–95% confluent by the following day. Cells should not be older than passage 8.

Water Soluble Compounds

Compounds were initially screened at 50 µM and 10 µM. A 50 mM stock solution for each compound was prepared in culture medium. The stock solution was diluted to 5 mM and 1 mM. When 10 µL of the 5 mM solution was added to the well (1 mL medium/well), the final concentration was 50 µM. Adding 10 µL of the 1 mM solution to the well provides a final concentration of 10 µM.

Water Insoluble Compounds

Compounds which will not go into solution in culture medium were resuspended in DMSO at a concentration of 25 mM. The stock solution was then diluted to the final concentration in culture medium. The old medium was aspirated and 1 mL of the new medium with the compound was added. For example, if the final concentration was 50 µM, the 2 µL of the 25 mM stock was added per mL of culture medium. The 50 mM solution was diluted for lower concentrations.

Example 669

In Vitro MCP-1 Activity Assay

Cultured human endothelial cells were seeded in 96-well plates. On the following day cells were stimulated with TNF-α (1 ng/ml) in the presence or absence of compounds dissolved in DMSO. To establish a dose curve and IC50 for each compound, multiple concentrations in 2-fold increments were used. Cells were exposed to TNF-α and compounds for approximately 16 hours. The next day the cells were visually examined via light microscopy to score for visual signs of toxicity. Cell culture media, diluted 1:10, was analyzed by an MCP-1 immunoassay kit (R & D Systems). This assay is a sandwich immunoassay using immobilized anti-MCP-1 antibody in 96-well plate to capture secreted MCP-1 in cell culture media. Captured MCP-1 is subsequently detected with a horse radish peroxidase-conjugated anti-MCP-1 antibody for color development. Results are expressed as IC50 values (the amount of compound (□M) required to achieve a 50% reduction compared to control (cells stimulated with TNF-α only)).

Example 670

In Vitro Smooth Muscle Cell Activity Assay

Cultured human aortic smooth muscle cells were seeded in 24-well plates. When cells reached 80% confluency, they were made quiescent by changing media to 0.2% serum (as compared to 5% serum in normal culture media) for 48 hours. The cells were then stimulated by addition of 5% serum in the presence or absence of compounds dissolved in DMSO. To establish a dose curve and IC50 for each compound, multiple concentrations in 5-fold increments were used. After 20 hr incubation, 3H-thymidine (0,5 µCi/per well) was added to the cells for 4 hours of labeling. Washed cells were then lysed in NaOH and, the amount of 3H-thymidine incorporation was determined. Results are expressed as IC50 values (the amount of compound (□M) required to achieve a 50% reduction compared to control (cells stimulated with 5% serum only)).

TABLE 3

| EXAMPLE NUMBER | MCP-1 Activity IC50 (μM) | Smooth Muscle Cell Activity IC50 (μM) |
|---|---|---|
| 61 | ND | 0.45 |
| 5 | ND | 0.45 |
| 50 | >50 | 0.94 |
| 51 | 20 | 1.25 |
| 41 | ND | 1.25 |
| 2 | 5 | 0.4 |
| 11 | 10 | 4.53 |
| 9 | 10 | 1.15 |
| 7 | 8 | 1.53 |
| 23 | ND | 2.33 |
| 62 | ND | 1.25 |
| 6 | >50 | 0.33 |

ND = Not determined

Example 671

In Vitro VCAM-1 Assay

The compounds were added to the plate (each compound is done in duplicate). One plate was prepared for VCAM expression and one plate was prepared for ICAM expression.

Immediately after the compounds were added, TNF was added to each well 100 units/mL TNF was usually added to each well. Since each lot of TNF varies in the number of units, each new lot was titrated to determine the optimum concentration. Therefore this concentration changed. If 100 units/mL was being used, TNF was dilted to 10 units/μL and 10 μL added to each well.

The plates were incubated at 37° C., 5% CO2 overnight (approximately 16 hours). The next day the plates were checked under the microscope to see if there were any visual signs of toxicity. Records were made of any cell death, debris, or morphology changes, as well as insoluble compounds (particulate or turbity).

The degree of inhibition of the compounds of formula (I) was determined by the assays. The results are provided in Table 4.

TABLE 4

| X | Z | VCAM-1 IC50 (μM) |
|---|---|---|
| 4-carboxymethoxy-3,5-dimethoxy, sodium salt | 2,4-dimethoxy-5-(benzo[b]thien-2-yl) | 0.7 |
| 2,4,6-trimethoxy | 2,4-difluoro | 0.7 |
| 2,3-dichloro-4-methoxy | 5-bromo-2-methoxy | 1 |
| 2,4,6-trimethoxy | 4-hydroxy-3,5-dimethoxy | 1 |
| 3,5-dimethoxy-4-(4-methoxybenzyloxy) | 3,4,5-trimethoxy | 1 |
| 3,4,5-trimethoxy | 5-bromo-2-methoxy | 1 |
| 2,3,4-trimethoxy | 3-bromo-4,5-dimethoxy | 1 |
| 3,4,5-trimethoxy | 3,4-dimethoxy-5-phenyl | 1 |
| 4-hydroxy-3,5-dimethoxy | 2,4-dimethoxy-5-(benzo[b]thien-2-yl) | 1.2 |
| 4-carboxymethoxy-3,5-dimethoxy | 2,4-dimethoxy-5-(benzo[b]thien-2-yl) | 1.3 |
| 2,3,4-trimethoxy | 5-(benzo[b]thien-2-yl)-3,4-dimethoxy | 1.4 |
| 3,4,5-trimethoxy | 2-methoxy-5-(4-methylthien-2-yl) | 1.5 |
| 3,4-dimethoxy | 2-methoxy-5-(5-methylthien-2-yl) | 1.5 |
| 3,4,5-trimethoxy | 2-methoxy-5-(5-methylthien-2-yl) | 1.5 |
| 3,5-dimethoxy-4-(1,4-benzodioxan-3-methoxy) | 3,4,5-trimethoxy | 1.5 |
| 2,5-dimethoxy | 2-methoxy-5-(thien-2-yl) | 1.5 |
| 3,4,5-trimethoxy | 3,4-dimethoxy-5-(thien-2-yl) | 1.5 |
| 3,4-dichloro-2-hydroxy, sodium salt | 2-methoxy-5-(thien-2-yl) | 1.6 |
| 3,4-dimethoxy | 2-methoxy-5-(4-methylthien-2-yl) | 2 |
| 3,4,5-trimethoxy | 3,4-dimethoxy-5-(3-pyridyl) | 2 |
| 3,4,5-trimethoxy | 2,4-dimethoxy-5-(thien-2-yl) | 2 |
| 3,4,5-trimethoxy | 5-bromo-2,4-dimethoxy | 2 |
| 3,5-dimethoxy | 2-methoxy-5-(thien-2-yl) | 2 |
| 4-iodo-2-methoxy | 2-methoxy-5-(thien-2-yl) | 2 |

TABLE 4-continued

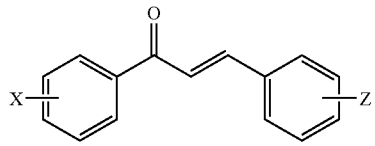

| X | Z | VCAM-1 IC50 (μM) |
|---|---|---|
| 4-(3,4-dimethoxybenzyloxy)-3-methoxy | 3,4,5-trimethoxy | 2 |
| 4-(3,4-dimethoxybenzyloxy)-3,5-dimethoxy | 3,4,5-trimethoxy | 2 |
| 2,4,5-trimethoxy | 3,4,5-trimethoxy | 2 |
| 3,4,5-trimethoxy | 2-bromo-4,5-dimethoxy | 2 |
| 3,4-dichloro-2-hydroxy | 5-bromo-2-methoxy | 2 |
| 3-methoxy-4-(3,4,5-trimethoxybenzyloxy) | 3,4,5-trimethoxy | 2 |
| 3-methoxy-4-(4-pyridylmethoxy), hydrogen chloride | 2-methoxy-5-(thien-2-yl) | 2 |
| 3-methoxy-4-(2-pyridylmethoxy), hydrogen chloride | 2-methoxy-5-(thien-2-yl) | 2 |
| 2-methoxy-4-(thien-2-yl) | 3,4-difluoro | 2.1 |
| 3,4,5-trimethoxy | 5-(benzo[b]thien-2-yl)-2-methoxy | 2.1 |
| 3,4-dichloro-2-hydroxy | 2-methoxy-5-(thien-2-yl) | 2.3 |
| 3,4-dimethoxy | 5-(benzo[b]thien-2-yl)-2-methoxy | 2.4 |
| 2,3,4-trimethoxy | 2,4-dimethoxy-5-(thien-2-yl) | 2.4 |
| 3-methoxy-4-(2-pyridylmethoxy) | 2-methoxy-5-(thien-2-yl) | 2.5 |
| 4-(fur-2-ylmethloxy)-3,5-dimethoxy | 3,4,5-trimethoxy | 2.5 |
| 4-iodo-2-methoxy | 3,4,5-trimethoxy | 2.5 |
| 2,4,6-trimethoxy | 3-bromo-4,5-dimethoxy | 2.5 |
| 3,4-methylenedioxy | 2-methoxy-5-(5-methylthien-2-yl) | 2.5 |
| 4-hydroxy-3,5-dimethoxy, sodium salt | 2,4-dimethoxy-5-(benzo[b]thien-2-yl) | 2.5 |
| 3-methoxy-4-(3-pyridylmethoxy) | 2-methoxy-5-(thien-2-yl) | 2.6 |
| 4-methoxy | 5-(benzo[b]thien-2-yl)-2-methoxy | 2.9 |
| 3,5-dimethoxy-4-(3,4-methylenedioxybenzyloxy) | 3,4,5-trimethoxy | 3 |
| 3,5-dimethoxy-4-(thien-2-ylmethoxy) | 3,4,5-trimethoxy | 3 |
| 3,4,5-trimethoxy | 3-fluoro-4-methoxy | 3 |
| 3,4-dimethoxy | 3-bromo-4,5-dimethoxy | 3 |
| 2,3,4-trimethoxy | 3,4-dimethoxy-5-(thien-2-yl) | 3 |
| 3,5-dimethoxy-4-(3,4,5-trimethoxybenzyloxy) | 3,4,5-trimethoxy | 3 |
| 3,4,5-trimethoxy | 5-(5-acetylthien-2-yl)-3,4-dimethoxy | 3 |
| 4-methoxy | 2-methoxy-5-(thien-2-yl) | 3 |
| 2,6-dimethoxy | 2-methoxy-5-(thien-2-yl) | 3 |
| 3,4-dimethoxy | 2-methoxy-5-(thien-2-yl) | 3 |
| 2,4,6-trimethoxy | 2-methoxy-5-(thien-2-yl) | 3 |
| 3,4,5-trimethoxy | 2-methoxy-5-(thien-2-yl) | 3 |
| 5-(2,4-dimethoxyphenyl) | 3,4,5-trimethoxy | 3 |
| 2-bromo-4,5-dimethoxy | 2-bromo-4,5-dimethoxy | 3 |
| 3,4,5-trimethoxy | 4-hydroxy | 3.5 |
| 3-methoxy-4-(4-methoxybenzyloxy) | 3,4,5-trimethoxy | 3.7 |
| 4-(4-ethoxycarbonyl-benzyloxy)-3-methoxy | 2-methoxy-5-(thien-2-yl) | 3.7 |
| 4-(2,3-isopropylidenedioxy-1-propoxy)-3,5-dimethoxy | 5-(benzo[b]thien-2-yl)-2,4-dimethoxy | 3.8 |
| 3-methoxy-4-(4-pyridylmethoxy) | 2-methoxy-5-(thien-2-yl) | 4 |
| 4-(3-acetylphenyl)-2-methoxy | 3,4,5-trimethoxy | 4 |
| 3,4,5-trimethoxy | 3-bromo-4,5-dimethoxy | 4 |
| 3,4-methylenedioxy | 5-bromo-2-methoxy | 4 |
| 3,4-methylenedioxy | 2-methoxy-5-(thien-2-yl) | 4 |

TABLE 4-continued

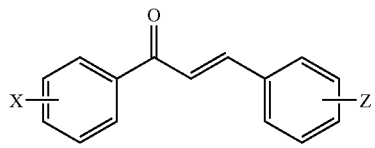

| X | Z | VCAM-1 IC50 ($\mu$M) |
|---|---|---|
| 3,4-methylenedioxy | 2-methoxy-5-(4-methylthien-2-yl) | 4 |
| 2-methoxy-5-(thien-2-yl) | 4-ethoxy-3-fluoro | 4.3 |
| 3,4,5-trimethoxy | 5-(benzo[b]thien-2-yl)-2-carboxymethoxy-4-methoxy, sodium salt | 4.3 |
| 3,4,5-trimethoxy | 5-(benzo[b]thien-2-yl)-3,4-dimethoxy | 5 |
| 3,4,5-trimethoxy | 5-(benzo[b]thien-2-yl)-2,4-dimethoxy | 5 |
| 4-(4-carboxybenzyloxy)-3-methoxy | 2-methoxy-5-(thien-2-yl) | 5 |
| 3,5-dimethoxy-4-(2-methoxyethoxy) | 3,4,5-trimethoxy | 5 |
| 2,3,4-trimethoxy | 5-(4-formylphenyl)-3,4-dimethoxy | 5 |
| 2,4-dimethoxy | 4-trifluoromethyl | 5.3 |
| 3,4-difluoro | 2-methoxy-5-(thien-2-yl) | 6 |
| 3,4,5-trimethoxy | hydrogen | 6 |
| 4-(3-chlorophenyl) | 3,4,5-trimethoxy | 6 |
| 3,4,5-trimethoxy | 4-(thien-2-yl) | 6 |
| 5-(3-chlorophenyl)-2,4-dimethoxy | 3,4,5-trimethoxy | 6 |
| 4-(4-aminobenzyloxy)-3-methoxy | 2-methoxy-5-(thien-2-yl) | 7 |
| 3-methoxy-4-(3,4-methylenedioxybenzyloxy) | 3,4,5-trimethoxy | 7 |
| 4-hydroxy-3-methoxy | 2-methoxy-5-(thien-2-yl) | 7 |
| 2,3,4-trimethoxy | 5-(benzo[b]thien-2-yl)-2,4-dimethoxy | 8.1 |
| 3,4,5-trimethoxy | 5-(benzo[b]thien-2-yl)-2-carboxymethoxy-4-methoxy | 8.3 |
| 3,5-di-tert-butyl-4-methoxy | hydrogen | 9 |
| 3,5-dimethoxy-4-(2-morpholinoethoxy) | 5-(benzo[b]thien-2-yl)-2,4-dimethoxy | 10 |
| 2-methoxy-4-(3-methoxyphenyl) | 2-methoxy-5-(thien-2-yl) | 11 |
| 3,4-dimethoxy | 5-(benzo[b]thien-2-yl)-2,4-dimethoxy | 11 |
| 3,4,5-trimethoxy | 4-bromo | 11 |
| 2,5-dimethoxy-4-(thien-2-yl-methoxy) | 2-methoxy-5-(thien-2-yl) | 12 |
| 3,4-dimethoxy | 4-(thien-2-yl) | 12 |
| 2,4-dihydroxy | 4-hydroxy | 12 |
| 5-bromo-2,4-dimethoxy | 3,4,5-trimethoxy | 12.5 |
| 2,4,5-triethoxy | 3-bromo-4,5-dimethoxy | 15 |
| 4-methoxy | 3,4-dimethoxy | 15 |
| 2-methoxy-4-(thien-2-yl) | 2-methoxy-4-(thien-2-yl) | 16 |
| 2,4-di-tert-butyl-3-methoxy | 4-methoxy | 17 |
| hydrogen | hydrogen | 23 |
| 4-fluoro | 4-fluoro | 25 |
| hydrogen | 4-nitro | 30 |
| 4-methoxy | hydrogen | 32 |
| 3,4-dichloro-2-hydroxy | 5-(benzo[b]thien-2-yl)-2-methoxy | 50 |
| 3-chloro | hydrogen | 57 |
| 3,5-di-tert-butyl-4-hydroxy | 4-methoxy | >50 |
| 4-methyl | 3,5-di-tert-butyl-4-hydroxy | >50 |
| hydrogen | 3,5-di-tert-butyl-4-hydroxy | >50 |
| 3-methoxy-4-(4-tert-butyloxy-carbonylaminobenzyloxy) | 2-methoxy-5-(thien-2-yl) | >50 |
| hydrogen | 2,4,6-triisopropyl | >50 |
| 4-bromo | 3,4,5-trimethoxy | >50 |
| 4-benzyloxy-3,5-dimethoxy | 3-bromo-4,5-dimethoxy | >50 |

TABLE 4-continued
![chalcone structure with X and Z substituents]
| X | Z | VCAM-1 IC50 (μM) |
|---|---|---|
| 3,5-dimethoxy-4-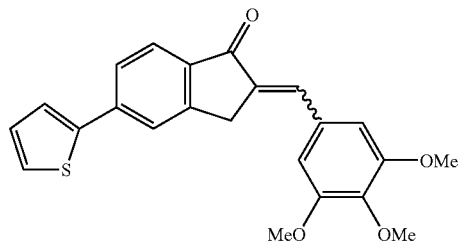 | 5-(benzo[b]thien-2-yl)-2,4-dimethoxy | >50 |
Alternatively, the degree of inhibition of the compounds of formula (I) was determined and tabulated in Table 5.
TABLE 5
| Ex. No. | Structure | VCAM-1 (μM) |
|---|---|---|
| 53 | 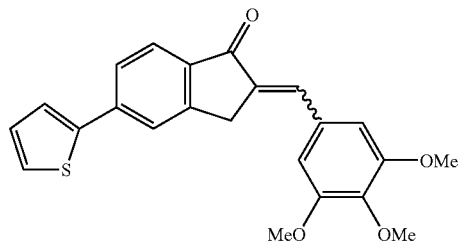 | >50 |
| 54 | 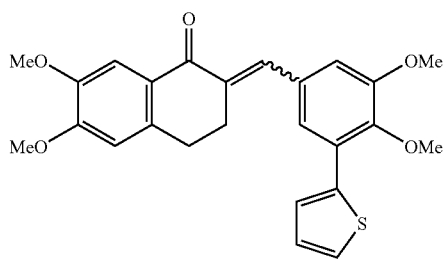 | 2 |

TABLE 5-continued

| Ex. No. | Structure | VCAM-1 (□M) |
|---|---|---|
| 55 | 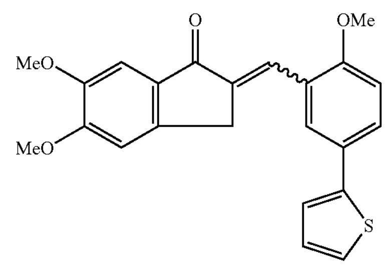 | >50 |

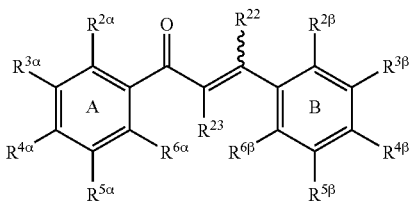

Example 672

Mouse Peritonitis Model

FIG. 2 is a bar chart graph of the inhibition of eosinophil recruitment (percent eosinophils in the peritoneal fluid) by 50 mg/kg/dose of 3-[5-(benzo[b]thien-2-yl)-2,4-dimethoxyphenyl]-1-(3,4,5-trimethoxyphenyl)-2-propen-1-one. Balb/C mice (n=10) were sensitized to ovalbumin on days 0 and 7 with a subcutaneous injection of ovalbumin absorbed in aluminum hydroxide. They were then challenged with an intraperitoneal injection of ovalbumin and sacrificed 48 hrs post-challenge. Peritoneal fluid was then collected and spun down onto slides. Slides were stained with DiffQuik and a differential performed. The test compound was administered by subcutaneously injection −24, −2, +2 and +6 hrs around the time of ovalbumin challenge. This is a model of allergic inflammation as eosinophils are the major leukocyte recruited into the peritoneum.

Example 673

Paw Edema Model

FIG. 3 is a bar chart graph of the inhibition of paw edema in a mouse model of delayed type hypersensitivity by 50 mg/1 kg/dose of 3-[5-(benzo[b]thien-2-yl)-2,4-dimethoxyphenyl]-1-(3,4,5-trimethoxyphenyl)-2-propen-1-one. Balb/C mice (n=5) were sensitized intradermally on day 0 with methylated BSA (metBSA). They were then challenged with metBSA on day 7 in the right hind paw. The animals were sacrificed 24 hours later and the left and right hind paws weighed. The left hindpaw weight is subtracted from the right hind paw to give the paw weight increase. The test compound was administered by intraperitoneal injection −24, −2 and +6 hrs around the time of metBSA challenge.

Modifications and variations of the present invention relating to compounds that inhibit the suppression of VCAM-1 and methods of treating diseases mediated by the expression of VCAM-1 will be obvious to those skilled in the art from the foregoing detailed description of the invention. Such modifications and variations are intended to come with the scope of the appended claims.

What is claimed is:

1. A compound of the formula (I)

(I)

or its pharmaceutically acceptable salt, wherein:
i) the wavy line indicates that the compound can be in the form of the E or Z isomer;
ii) $R^{22}$ and $R^{23}$ are independently hydrogen or $(C_1-C_4)$ alkyl;
iii) $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently hydrogen, alkyl, carbocycle, aryl, heteroaryl, heterocycle, cycloalkyl, alkoxy, aryloxy, arylalkoxy, heteroaryloxy, heteroarylalkoxy, alkylthio, alkylamino, aminoalkyl, haloalkylthio, acyl, haloalkyl, aryloxy, amido, acylamino, amino, dialkylamino, aminodialkyl, trifluoroalkoxy, alkylsulfonyl, haloalkylsulfonyl, aminocarbonyl, alkenyl, alkynyl, halogen, hydroxyl, thiol, cyano, nitro, sulfonic acid, sulfonate, sulfate, sulfinic acid, sulfenic acid, sulfamide, sulfonamide, sulfoxide, metal sulfinate, phosphate, phosphonate, metal phosphonate, phosphinate, alditol, carbohydrate, amino acid, OC$(R^1)_2CO_2H$, $SC(R^1)_2CO_2H$, $NHCHR^1CO_2H$, CO—$R^2$, $CO_2R^1$, polyoxyalkylene, polyol alkyl, oxyalkylamino, alkylcarbonylalkyl, lower alkyl S(O)-lower alkyl, lower alkyl-$S(O)_2$-lower alkyl; hydroxyalkyl, aralkoxy, heteroaryl lower alkoxy, heterocyclo lower alkoxy, heteroaryloxy, heterocycleoxy, aralkyl lower thioalkyl, heteroaralkyl lower thioalkyl, heterocycloalkyl lower thioalkyl, heteroaryl lower alkyl, heterocyclo lower alkyl, heteroarylthio lower alkyl, arylthio lower alkyl, heterocyclothio lower alkyl, heteroarylamino lower alkyl, heterocycloamino lower alkyl, arylsulfinyl lower alkyl, arylsulfonyl lower alkyl, any of which can be optionally substituted with a moiety that does not adversely affect the biological properties of the molecule; —C(O)(CH$_2$)$_2$CO$_2^-$M$^+$, —SO$_3$M$^+$, or -lower alkyl-O—R, wherein R is PO$_2$(OH)$^-$M$^+$, PO$_3$(OH)$^-$M$^+$ or —SO₃M⁺, wherein M⁺ is a pharmaceutically acceptable cation; -lower alkylcarbonyl-lower alkyl; carboxy lower alkyl; -lower alkylamino-lower alkyl; N,N-di-substituted amino lower alkyl-, wherein the substituents each independently represent lower alkyl;

iv) $R^1$ is H, lower alkyl, an optionally substituted carbocycle, aryl, heteroaryl, heterocycle, alkylaryl, alkylheteroaryl, alkylheteroaryl or alkylheterocycle;

v) $R^2$ is an optionally substituted alkyl, alkenyl, alkynyl, aryl, carbocycle, heteroaryl, heterocycle, alkylaryl, alkylheteroaryl, alkylheteroaryl or alkylheterocycle;

vi) alternatively, $R^{22}$ and $R^{6\alpha}$ or $R^{23}$ and $R^{6\alpha}$ can join together to form a bridged carbocycle, aryl, heterocycle or heteroaromatic;

vii) $R^{2\alpha}$ and $R^{3\alpha}$, $R^{3\alpha}$ and $R^{4\alpha}$, $R^{4\alpha}$ and $R^{5\alpha}$, $R^{5\alpha}$ and $R^{6\alpha}$, $R^{2\beta}$ and $R^{3\beta}$, $R^{3\beta}$ and $R^{4\beta}$, $R^{4\beta}$ and $R^{5\beta}$ or $R^{5\beta}$ and $R^{6\beta}$ can independently join to form a bridged compound selected from the group consisting of an optionally substituted carbocycle, an optionally substituted cycloalkenyl, an optionally substituted cycloalkylcarbonyl, an optionally substituted cycloalkenylcarbonyl; an optionally substituted aryl, an optionally substituted heterocylic or an optionally substituted heteroaromatic, or alkylenedioxy or wherein the ring can include a carbonyl, cyclic ester, amide, amine, sulfonate, or phosphonate;

viii) at least one of $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ or $R^{6\beta}$ is, or $R^{2\alpha}$ and $R^{3\alpha}$, $R^{3\alpha}$ and $R^{4\alpha}$, $R^{4\alpha}$ and $R^{5\alpha}$, $R^{5\alpha}$ and $R^{6\alpha}$, $R^{2\beta}$ and $R^{3\beta}$, $R^{3\beta}$ and $R^{4\beta}$, $R^{4\beta}$ and $R^{5\beta}$ or $R^{5\beta}$ and $R^{6\beta}$ come together to be, an optionally substituted heterocycle or heteroaromatic selected from the group consisting of pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, 1,4-dioxanyl, aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, isothiazolyl, imidazolyl, pyrazinyl, benzofuranyl, quinolyl, isoquinolyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4- thiadizolul, isooxazolyl, pyrrolyl, quinazolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, and pteridinyl; and ix) at least one of $R^{2\alpha}$, $R^{3\alpha}$, $R^{4\alpha}$, $R^{5\alpha}$, or $R^{6\alpha}$, and at least one of $R^{2\beta}$, $R^{3\beta}$, $R^{4\beta}$, $R^{5\beta}$ or $R^{6\beta}$ is a substituent other than hydrogen.

2. The compound of claim 1 of formula (II):

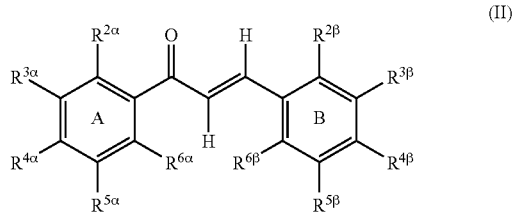

(II)

or its pharmaceutically acceptable salt.

3. The compound of claim 1, wherein $R^1$ is independently H or lower alkyl, $R^2$ is an optionally substituted alkyl; and at least one of $R^{2\alpha}$, $R^{3\alpha}$, $R^{4\alpha}$, $R^{5\alpha}$, or $R^{6\alpha}$, and at least one of $R^{2\beta}$, $R^{3\beta}$, $R^{4\beta}$, $R^{5\beta}$ or $R^{6\beta}$ is a substituent other than hydrogen.

4. The compound of claim 1, wherein $R^{4\beta}$ or $R^{5\beta}$ is optionally substituted heteroaryl or heterocycle; and at least one of $R^{2\alpha}$, $R^{3\alpha}$, $R^{4\alpha}$, $R^{5\alpha}$, or $R^{6\alpha}$ is a substituent other than hydrogen.

5. The compound of claim 1, wherein $R^{4\alpha}$, or $R^{5\alpha}$ is optionally substituted heteroaryl or heterocycle; and at least one of $R^{2\alpha}$, $R^{3\alpha}$, $R^{4\alpha}$, $R^{5\alpha}$, or $R^{6\alpha}$ is a substituent other than hydrogen.

6. The compound of claim 1, wherein $R^{5\beta}$; $R^{2\alpha}$, $R^{3\alpha}$, $R^{4\alpha}$, $R^{5\alpha}$, $R^{6\alpha}$, or $R^{2\beta}$, $R^{3\beta}$, $R^{4\beta}$, and $R^{6\beta}$ are independently hydrogen, methoxy, ethoxy, propoxy, benzyloxy, 4-carboxybenzyloxy, 4-ethoxycarbonylbenzyloxy, 4-aminobenzyloxy, fluoro, chloro, bromo, iodo, hydroxy, OCH₂CO₂H, SCH₂CO₂H, NHCH₂CO₂H, CO₂H, pyrid-2-ylmethoxy, pyrid-3-ylmethoxy, pyrid4-ylmethoxy; fur-2-ylmethoxy, fur-3-ylmethoxy, and at least one of $R^{2\alpha}$, $R^{3\alpha}$, $R^{4\alpha}$, $R^{5\alpha}$, or $R^{6\alpha}$ is a substituent other than hydrogen.

7. The compound of claim 1 wherein at least one of $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ or $R^{6\beta}$, is or $R^{2\alpha}$ and $R^{3\alpha}$, $R^{3\alpha}$ and $R^{4\alpha}$, $R^{4\alpha}$ and $R^{5\alpha}$, $R^{5\alpha}$ and $R^{6\alpha}$, $R^{2\beta}$ and $R^{3\beta}$, $R^{3\beta}$ and $R^{4\beta}$, $R^{4\beta}$ and $R^{5\beta}$ or $R^{5\beta}$ and $R^{6\beta}$ join to form a carbocycle, aryl, heterocycle or heteroaromatic in which the carbocycle, aryl, heteroaryl or heterocycle is a 5, 6 or 7 membered ring, optionally conjugated to another carbocycle, aryl, heteroaryl or heterocycle.

8. The compound of claim 1, wherein $R^{3\alpha}$ and $R^{4\alpha}$ or $R^{5\alpha}$ and $R^{4\alpha}$ join to form a 5-membered methylendioxyphenyl group.

9. The compound of claim 1, wherein a heteroaryl or heteroaryl is on the A ring.

10. The compound of claim 1, wherein a heteroaryl or heteroaromatic is on the B ring.

11. The compound of claim 1, wherein the compound has a substituent that increases the water solubility of the compound.

12. The compound of claim 11, wherein the water solubilizing moiety is selected from the group consisting of alkoxy, alditol, carbohydrate, amino acid, OC(R¹)₂CO₂H, SC(R¹)₂CO₂H, NHCHR¹CO₂H, CO—R² and CO₂R¹.

13. The compound of claim 11, wherein the solubilizing substituent is a residue of glycolic acid.

14. The compound of claim 11, wherein the optionally substituted heteroaryl or heterocyclic attached to the A or B phenyl ring is selected from the group consisting of pyrrolidinyl, tetrahydrofuryl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl, aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl and 1,3,5-triazinyl.

15. The compound of claim 11, wherein the optionally substituted heteroaryl or heterocyclic attached to the A or B phenyl ring is selected from the group consisting of, isothiazolyl, imidazolyl, pyrazinyl, benzofuranyl, quinolyl, isoquinolyl, isobenzofuryl, pyrazolyl, indolyl, isoindolyl, benzimidazolyl, purinyl, carbazolyl, oxazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, and imidazole.

16. The compound of claim 11, wherein the optionally substituted heteroaryl or heterocyclic attached to the A or B phenyl ring is selected from the group consisting of 1,2,3-triazole, 1,2,4-triazole, 1,2,3-oxadiazole, thiazine, pyridazine and pteridinyl.

17. The compound of claim 1 the formula:

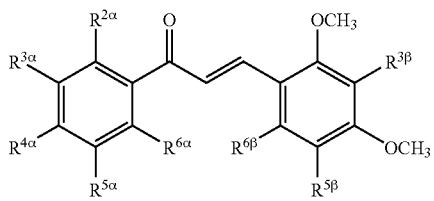

or its pharmaceutically acceptable salt thereof.

18. The compound of claim 1 of the formula:

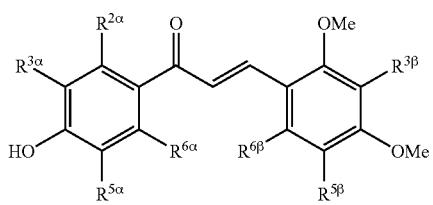

or its pharmaceutically acceptable salt.

19. The compound of claim 1 of the formula:

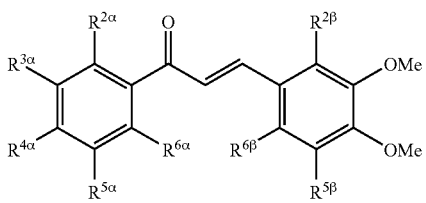

or its pharmaceutically acceptable salt.

20. The compound of claim 1 of the formula:

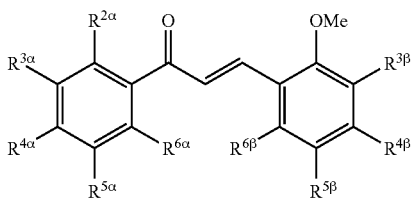

or its pharmaceutically acceptable salt.

21. The compound of claim 1, wherein the compound is of the formula:

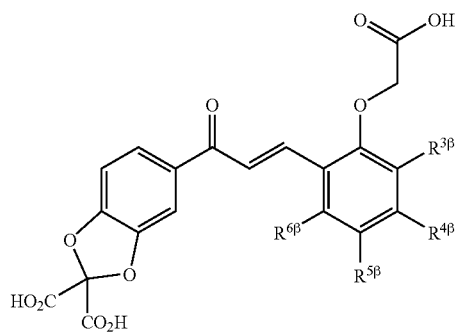

or its pharmaceutically acceptable salt.

22. The compound of claim 1 of the formula:

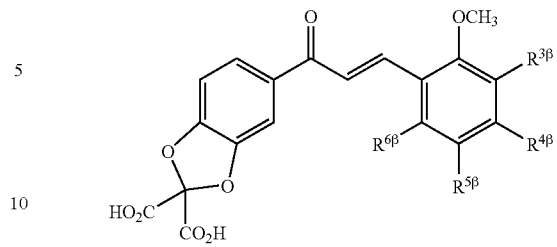

or its pharmaceutically acceptable salt.

23. The compound of claim 1 of the formula:

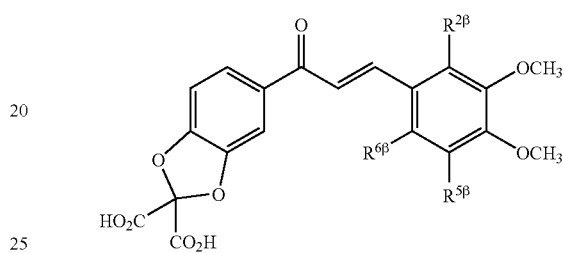

or its pharmaceutically acceptable salt thereof.

24. The compound of claim 1 of the formula:

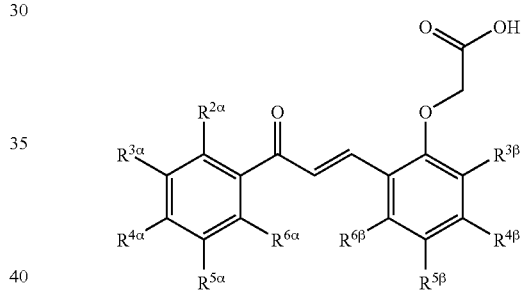

or its pharmaceutically acceptable salt thereof.

25. The compound of claim 1 of the formula:

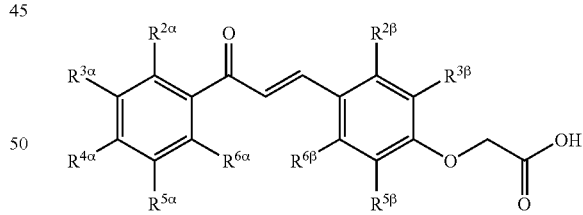

or its pharmaceutically acceptable salt.

26. The compound of claim 1, the formula:

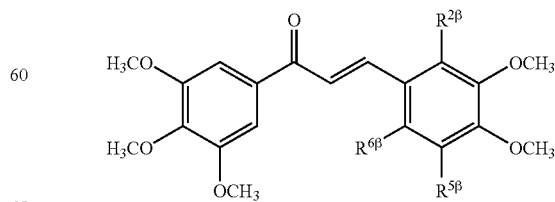

or its pharmaceutically acceptable salt.

27. The compound of claim 1 of the formula:

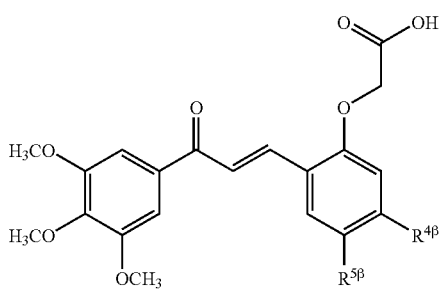

or its pharmaceutically acceptable salt.

28. The compound of claim 1 of the formula:

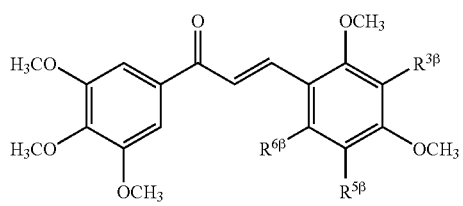

or its pharmaceutically acceptable salt.

29. The compound of claim 1 of the formula:

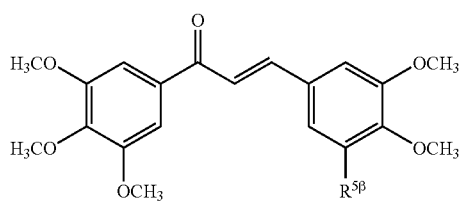

wherein Y is a phenyl ring fused to another heteroaromatic or heterocycle.

30. The compound of claim 1 of the formula:

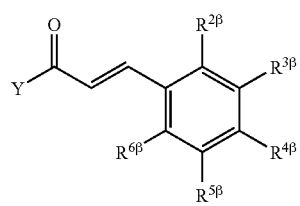

wherein Y is a phenyl ring fused to another heteroaromatic or heterocycle.

31. The compound of claim 1 of the formula:

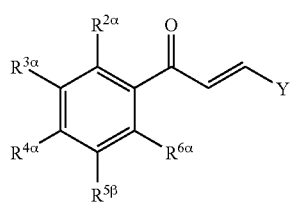

or its pharmaceutically acceptable salt thereof, wherein Y is a phenyl ring fused to another heteroaromatic or heterocycle.

32. The compound of claim 1, wherein the compound is of the formula:

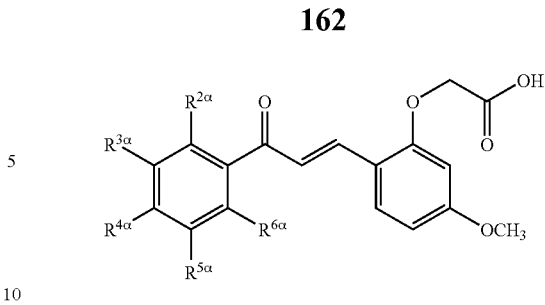

or its pharmaceutically acceptable salt.

33. The compound of claim 1, wherein the compound is of the formula:

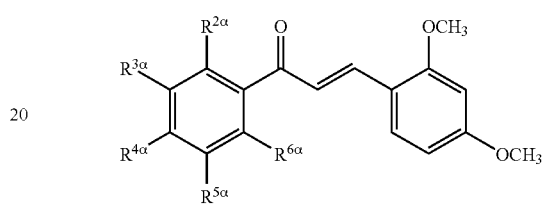

or its pharmaceutically acceptable salt.

34. The compound of claim 1, wherein the compound is of the formula:

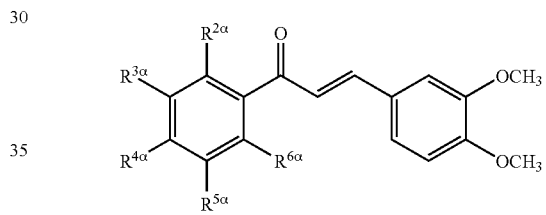

or its pharmaceutically acceptable salt.

35. The compound of claim 1 of the formula:

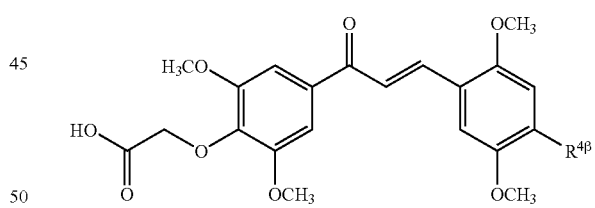

wherein $R^4$[[¤]]$^\beta$ is a heteroaryl or heterocycle.

36. The compound of claim 1 of the formula:

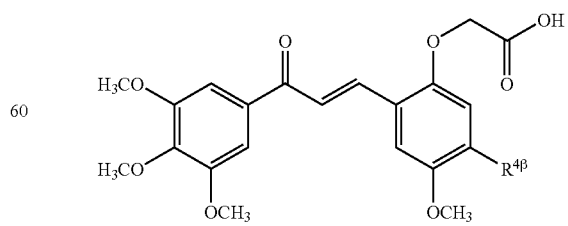

wherein $R^4$[[¤]]$^\beta$ is a heteroaryl or heterocycle.

37. The compound of claim 1 of the formula:

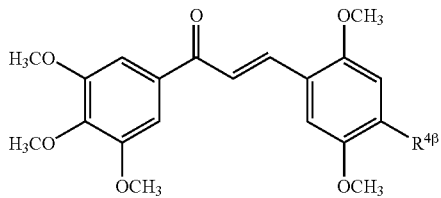

or its pharmaceutically acceptable salt, wherein $R^{4\beta}$ is a heteroarayl or heterocyclic.

38. The compound of claim 1 of the formula:

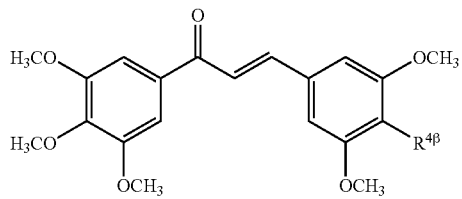

or its pharmaceutically acceptable salt, wherein $R^{4\beta}$ is a heteroaryl or heterocycle.

39. The compound of claim 1 of the formula:

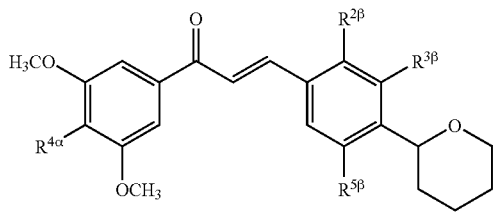

or its pharmaceutically acceptable salt.

40. The compound of claim 1 of the formula:

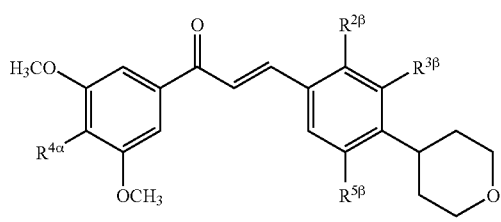

or its pharmaceutically acceptable salt.

41. A pharmaceutical composition comprising an effective amount of compound any one of claims 1–20, 21–31, 32–34, or 35–40 in a pharmaceutically acceptable carrier.

42. The pharmaceutical composition of claim 41 further comprising a second biologically active agent selected from the group consisting of heparin, frusemide, ranitidine, DNAase, an immunosuppressive agent, IV gamma globulin, troleandomycin, cyclosporin (Neoral), methotrexate, FK-506, Myochrysine (gold sodium thiomalate), platelet activating factor (PAF) antagonist, thromboxane inhibitor, leukotriene-$D_4$-receptor antagonist, Accolate (zafirlukast), Ziflo (zileuton), leukotriene $C_1$ or $C_2$ antagonist, inhibitor of leukotriene synthesis, zileuton or an inducible nitric oxide synthase inhibitor, prophylactic agent, sodium cromoglycate, Intal (cromolyn sodium, Nasalcrom, Opticrom, Crolom, Ophthalmic Crolom), Tilade (nedocromil, nedocromil sodium), ketotifen, $\beta_2$-adrenergic agonist, corticosteriod, antihistimine ($H_1$ receptor antagonist), xanthines and methylxanthines, Theo-24 (theophylline, Slo-Phylline, Uniphyllin, Slobid, Theo-Dur), Choledyl (oxitriphylline), aminophylline; anticholinergic agent (antimuscarinic agent), belladonna alkaloids, Atrovent (ipratropium bromide), atropine, oxitropium bromide; phosphodiesterase inhibitors, zardaverine; calcium antagonists, nifedipine; potassium activators, cromakalim, P38 kinase inhibitors, tricyclic antidepressents, cJun kinase inhibitors and cylcooxygenase-2 (COX-2) inhibitors.

43. The pharmaceutical composition of claim 42, wherein the second biologically active agent is a $\beta_2$-adrenergic agonist which is selected from the group consisting of albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tomalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmnoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

44. The pharmaceutical composition of claim 42, wherein the second biologically active agent is a corticosteriod which is selected from the group consisting of glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

45. The pharmaceutical composition of claim 42, wherein the second biologically active agent is a antihistimine ($H_1$ receptor antagonist) which is selected from the group consisting of Chlortrimeton (Teldrin, chlorpheniramine), Atrohist (brompheniramine, Bromarest, Bromfed, Dimetane), Actidil (triprolidine), Dexchlor (Poladex, Polaramine, dexchlorpheniramine), Benadryl (diphen-hydramine), Tavist (clemastine), Dimetabs (dimenhydrinate, Dramamine, Marmine), PBZ (tripelennamine), pyrilamine, Marezine (cyclizine), Zyrtec (cetirizine), hydroxyzine, Antivert (meclizine, Bonine), Allegra (fexofenadine), Hismanal (astemizole), Claritin (loratadine), Seldane (terfenadine), Periactin (cyproheptadine), Nolamine (phenindamine, Nolahist), Phenameth (promethazine, Phenergan), Tacaryl (methdilazine) and Temaril (trimeprazine).

46. A method for the treatment of an inflammatory or cardiovascular disorder in a host, comprising administering an effective amount of compound of claims 1–20, 21–31, 32–34, 35–40.

47. The method of claim 46, wherein the disorder is arthritis.

48. The method of claim 46, wherein the disorder is asthma.

49. The method of claim 46, wherein the disorder is dermatitis.

50. The method of claim 46, wherein the disorder is psoriasis.

51. The method of claim 46, wherein the disorder is cystic fibrosis.

52. The method of claim 46, wherein the disorder is post transplantation late or chronic solid organ rejection.

53. The method of claim 46, wherein the disorder is multiple sclerosis.

54. The method of claim 46, wherein the disorder is atherosclerosis.

55. The method of claim 46, wherein the disorder is post-angioplasty restenosis.

56. The method of claim 46, wherein the disorder is coronary artery disease.

57. The method of claim 46, wherein the disorder is angina or small artery disease.

58. The method of claim 46, wherein the arthritis is systemic lupus erythematosus.

59. The method of claim 46, wherein the disorder is Crohn's disease.

60. The method of claim 46, wherein the disorder is rheumatoid arthritis.

61. The method of claim 46, wherein the disorder is inflammatory bowel diseases.

62. The method of claim 46, wherein the disorder is autoimmune diabetes.

63. The method of claim 46, wherein the disorder is diabetic retinopathy.

64. The method of claim 46, wherein the disorder is rhinitis.

65. The method of claim 46, wherein the disorder is ischemia-reperfusion injury.

66. The method of claim 46, wherein the disorder is chronic obstructive pulmonary disease (COPD).

67. The method of claim 46, wherein the disorder is glomerulonephritis.

68. The method of claim 46, wherein the disorder is Graves disease.

69. The method of claim 46, wherein the disorder is gastrointestinal allergies.

70. The method of claim 46, wherein the disorder is conjunctivitis.

71. The method of claim 46, further comprising administering the compound in alternation or combination with an effective amount of a second biologically active agent.

72. The method of claim 46 wherein the disorder is an inflammatory disorder.

73. The method of claim 46 wherein the disorder is a cardiovascular disorder.

* * * * *